US010864261B2

(12) United States Patent
Seeberger et al.

(10) Patent No.: US 10,864,261 B2
(45) Date of Patent: Dec. 15, 2020

(54) **SYNTHETIC VACCINES AGAINST *STREPTOCOCCUS PNEUMONIAE* SEROTYPE 2**

(71) Applicant: Max-Planck-Gesellschaft zur Förderung der Wissenschaften e.V., Munich (DE)

(72) Inventors: Peter H. Seeberger, Kleinmachnow (DE); Claney Lebev Pereira, Berlin (DE); Chakkumkal Anish, The Hague (NL); Naeem Khan, Berlin (DE); Madhu Emmadi, Berlin (DE)

(73) Assignee: Max-Planck-Gesellschaft zur Förderung der Wissenschaften e.V., Munich (DE)

( * ) Notice: Subject to any disclaimer, the term of this patent is extended or adjusted under 35 U.S.C. 154(b) by 194 days.

(21) Appl. No.: 16/061,478

(22) PCT Filed: Dec. 16, 2016

(86) PCT No.: PCT/EP2016/081586
§ 371 (c)(1),
(2) Date: Jun. 12, 2018

(87) PCT Pub. No.: WO2017/103211
PCT Pub. Date: Jun. 22, 2017

(65) Prior Publication Data
US 2020/0016257 A1 Jan. 16, 2020

(30) Foreign Application Priority Data

Dec. 17, 2015 (EP) .................................... 15200729
Apr. 28, 2016 (EP) .................................... 16167505

(51) Int. Cl.
| | |
|---|---|
| *A61K 39/09* | (2006.01) |
| *C07H 15/04* | (2006.01) |
| *A61K 31/7028* | (2006.01) |
| *C07H 15/00* | (2006.01) |
| *A61K 39/00* | (2006.01) |
| *A61K 47/36* | (2006.01) |
| *C07H 1/00* | (2006.01) |
| *A61K 31/715* | (2006.01) |

(52) U.S. Cl.
CPC ........ *A61K 39/092* (2013.01); *A61K 31/7028* (2013.01); *A61K 31/715* (2013.01); *A61K 47/36* (2013.01); *C07H 1/00* (2013.01); *C07H 15/00* (2013.01); *C07H 15/04* (2013.01); *A61K 2039/55505* (2013.01); *A61K 2039/6037* (2013.01); *A61K 2039/627* (2013.01)

(58) Field of Classification Search
None
See application file for complete search history.

(56) References Cited

U.S. PATENT DOCUMENTS

2019/0240309 A1* 8/2019 Seeberger ............ A61K 39/092

FOREIGN PATENT DOCUMENTS

| EP | 2932979 | * 10/2015 | ............ A61K 47/48 |
|---|---|---|---|
| EP | 3 331 556 B1 | 10/2018 | |
| WO | WO 2007/116028 | 10/2007 | |
| WO | WO 2014/097099 | 6/2014 | |

OTHER PUBLICATIONS

Emmadi et al., "A *Streptococcus pneumoniae* Type 2 Oligosaccharide Glycoconjugate Elicits Opsonic Antibodies and Is Protective in an Animal Model of Invasive Pneumococcal Disease" J Am Chem Soc vol. 139 pp. 14783-14791 (Year: 2017).*
Perciani et al., "Conjugation of Polysaccharide 6B from *Streptococcus pneumoniae* with Pneumococcal Surface Protein A: PspA Conformation and Its Effect on the Immune Response" Clinical and Vaccine Immunology vol. 20 No. 6 pp. 858-866 (Year: 2013).*
Bourke J., et al., "The synthesis and biological evaluation of mycobacterial p-hydroxybenzoic acid derivatives (p-HBADs)†," Org. Biomol. Chem. (2014) 12:1114-1123.
Bundle D. R., et al., "Design of a Candida albicans Disaccharide Conjugate Vaccine by Reverse Engineering a Protective Monoclonal Antibody," ACS Chem. Biol. (2012) 7:1754-1763 and Supplemental Materials.
Dhénin S. G. Y., et al., "Sensitive and specific enzyme immunoassays for antigenic trisaccharide from *Bacillus anthracis* spores," Org. Biomol. Chem. (2009) 7:5184-5199.
Guan et al., "Study on Metal-Induced Reactions of α-Diazocarbonyl Glucosides," J. Org. Chem. (2012) 77:8888-8895.
Kawano, T., et al., "Natural killer-like nonspecific tumor cell lysis mediated by specific ligand-activated Va14 NKT cells," Proc. Natl Acad. Sci. USA (1998) 95:5690-5693.
Jaiswal, N., et al., "Distribution of Serotypes, Vaccine Coverage, and Antimicrobial Susceptibility Pattern of *Streptococcus pneumoniae* in Children Living in SAARC Countries: A Systematic Review," PLOS One (2014) 9(9):1-9.
Joosten et al., "Chemo-enzymatic synthesis of tetra-, penta-, and hexasaccharide fragments of the capsular polysaccharide of *Streptococcus pneumoniae* type 14" Carbohydrate Research (2003) 338(23):2629-2651.
Le et al., "Current Trend in Pneumococcal Serotype Distribution in Asia," J Vaccines Vaccin. (2011) S:2:001-016.
Pozsgay, V., "Recent Developments in Synthetic Oligosaccharide-Based Bacterial Vaccines" Current Topics in Medicinal Chemistry (2008) 8(2):126-140.

(Continued)

*Primary Examiner* — Eric Olson
(74) *Attorney, Agent, or Firm* — Knobbe Martens Olson & Bear, LLP

(57) ABSTRACT

The present invention relates to a synthetic saccharide of general formula (I) that is related to *Streptococcus pneumoniae* serotype 2 capsular polysaccharide, a conjugate thereof and the use of said saccharide and conjugate for raising a protective immune response in a human and/or animal host. Furthermore, the synthetic saccharide of general formula (I) is useful as marker in immunological assays for detection of antibodies against *Streptococcus pneumoniae* type 2 bacteria.

17 Claims, 7 Drawing Sheets

(56) References Cited

OTHER PUBLICATIONS

Rajput, V. K., et al., "Concise Synthesis of a Pentasaccharide Related to the Anti-Leishmanial Triterpenoid Saponin Isolated from Maesa balansae†," J. Org. Chem. (2008) 73:6924-6927.
International Search Report and Written Opinion dated Jan. 30 2017 for PCT Application No. PCT/EP2016/081586, filed Dec. 16, 2016.
Communication under Rule 71(3) EPC (Intention to Grant) dated Jul. 9, 2018 for EP Application No. 16809888.7, filed Dec. 16, 2016.
International Preliminary Report on Patentability dated Jun. 19, 2018 for PCT Application No. PCT/EP2016/081586, filed Dec. 16, 2016.

* cited by examiner

| | | |
|---|---|---|
| C2+C3 | 290 | Glc(β1-3)Rha(α1-3)Rha(β1-4)Rha(α1-1)aminopentanol |
| C4+C5 | 296 | GlcA(α1-6)Glc(α1-2)Rha(β1-4)Glc(α1-3)]Rha(α1-3)Rha(α1-1)aminopentanol |
| C6+C7 | 291 | GlcA(α1-6)Glc(α1-2)Rha(α1-3)Rha(α1-1)aminopentanol |
| C8+C9 | 293 | Rha(β1-4)Glc(β1-3)Rha(α1-3)Rha(α1-1)aminopentanol |
| C10+C11 | 294 | Rha(β1-4)Glc(β1-1)aminopentanol |
| D2+D3 | 295 | GlcA(α1-6)Glc(α1-1)aminopentanol |
| D4+D5 | 292 | Rha(α1-3)Rha(α1-1)aminopentanol |
| D6+D7 | 167 | Rha(α1-1)aminopentanol |
| D8+D9 | 168 | Rha(α1-3)Glc(β1-1)aminopentanol |
| D10+D11 | 241 | GlcA(α1-3)Gal(α1-1)aminopentanol |
| D12+D13 | 252 | Rha(α1-2)Rha(α1-2)Rha(α1-1)aminopentanol |
| E2+E3 | | SP2 native polysaccharide |
| E4+E5 | | SP19F native polysaccharide |
| E6+E7 | | Cell wall polysaccharide |

SYNTHETIC VACCINES AGAINST *STREPTOCOCCUS PNEUMONIAE* SEROTYPE 2

The present application is the national phase entry of PCT Application No. PCT/EP2016/081586, filed Dec. 16, 2016, which claims priority to EP Application No. 15200729.0, filed Dec. 17, 2015 and EP Application No. 16167505.3, filed Apr. 28, 2016, all of which are incorporated by reference in their entireties.

FIELD OF THE INVENTION

The present invention relates to a synthetic saccharide of general formula (I) that is related to *Streptococcus pneumoniae* serotype 2 capsular polysaccharide, a conjugate thereof and the use of said saccharide and conjugate for raising a protective immune response in a human and/or animal host. Furthermore, the synthetic saccharide of general formula (I) is useful as marker in immunological assays for detection of antibodies against *Streptococcus pneumoniae* type 2 bacteria.

BACKGROUND OF THE INVENTION

*Streptococcus pneumoniae* commonly known as pneumococci or diplococci is a human pathogenic Gram positive bacterium encapsulated with capsular polysaccharide. Based on the chemical nature of the polysaccharide capsule, pneumococci have been classified into more than 90 serotypes. Pneumococcus is a commensal bacterium that asymptomatically colonizes in the upper respiratory tract of human and is responsible for causing pneumonia, septicemia, meningitis and otitis media. Pneumococci is the most common cause of vaccine-preventable deaths in children aged<5 years and elderly peoples worldwide. Global estimates suggest that 18% of all deaths in children less than 5 years of age occur due to pneumonia.

Capsular polysaccharide is one of the major virulence factors responsible for pneumococcal pathogenesis. The spectrum of prevailing capsular types varies with age, time and geographical region, although common serotypes are consistently identified throughout the world. Globally, about 20 serotypes are associated with >80% of invasive pneumococcal disease occurring in all age groups; the 13 most common serotypes cause at least 70-75% of invasive disease in children. Pneumococcal vaccines that are currently available are capsular polysaccharide based and designed to cover the serotypes most frequently associated with invasive pneumococcal disease.

The available 23-valent polysaccharide vaccine (23-PPV) is not effective in children less than 2 years of age, while the 7-valent conjugate vaccines (7-PCV) is effective in children, but has limited serotype coverage.

To increase the serotype coverage, 10-valent conjugate vaccine containing the conjugates of the capsular polysaccharides from *S. pneumoniae* type 1, 4, 5, 6B, 7F, 9V, 14, 18C, 19F and 23F and protein D (a non-typeable *Haemophilus influenzae* protein), tetanus toxoid and diphtheria toxoid protein, and 13-valent conjugate vaccine containing the conjugates of capsular polysaccharides from *S. pneumoniae* type 1, 3, 4, 5, 6A, 6B, 7F, 9V, 14, 18C, 19A, 19F, and 23F and diphtheria $CRM_{197}$ protein have been licensed for use.

The currently available conjugate vaccines are highly effective in the children less than 2 years of age and use of these vaccines have led to a significant reduction in serious pneumococcal disease. However, emerging antibiotic resistant and serotype replacement with non-vaccine capsular types demonstrates the future problem and needs to address the necessitating changes in the vaccine spectrum and their high cost reduces both their acquisition and availability in many developing countries.

The international patent application WO2007116028A2 discloses a 9 or more valent *S. pneumoniae* immunogenic composition of capsular sacccharides from different *S. pneumoniae* serotypes which are conjugated to a carrier protein, wherein the composition comprises conjugated capsular saccharide 18C, which is less than 80, 70, 60, 50, 40, 30, 20, 15 or 10% O-acetylated. The application teaches that he de-O-acetylation of the capsular saccharide of serotype 18C may be beneficial in focusing the immune response on backbone epitopes which may be beneficial in raising an immune response protective against both 18C strains that are highly O-acetylated and those that are poorly O-acetylated.

The international patent application WO2014097099A2 discloses a method of making a glycoconjugate comprising a saccharide conjugated to a carrier protein by oxidizing the saccharide with a stable nitroxyl radical such as tetramethylpiperidine-N-oxide and subsequent coupling to an amino group of the carrier protein. The saccharide can be a bacterial capsular polysaccharide derived from *S. pneumoniae*.

Pozsgay describes protein conjugates of several oligosaccharide antigens (Current Topics in Medicinal Chemistry 2008, 8, p. 126-140). Among them are glycoconjugates of *S. pneumoniae* serotypes 3, 6B and 14.

Joosten et al. report a chemo-enzymatic synthesis of tetra-, penta-, and hexasaccharide fragments of the capsular polysaccharide of serotype 14 (Carbohydrate Research 2003, 338, p. 2629-2651). Linear intermediates were synthesized via chemical synthesis, followed by enzymatic galatosylation.

Recent studies show that *S. pneumoniae* type 2, a serotype not covered by the currently commercially available vaccines, has emerged in the SAARC (The South Asian Association for Regional Cooperation) countries. *S. pneumoniae* type 2 is responsible for 4.54% of invasive pneumococcal disease in children in Nepal and 8.9% of invasive pneumococcal disease in children in Banglagesh (hospital based study) (Distribution of Serotypes, Vaccine Coverage, and Antimicrobial Susceptibility Pattern of *Streptococcus Pneumoniae* in Children Living in SAARC Countries: A Systematic Review Jaiswal, N. et al. *PLOS ONE* 2014, 9). Further population based studies on pneumococcal serotype distribution attest that *S. pneumoniae* type 2 is the most prevalent serotype in Bangladesh causing 12.2% of invasive pneumococcal diseases (Current Trend in Pneumococcal Serotype Distribution in Asia, Le C. et al. *J Vaccines Vaccin* 2011). Hence, there is a high need to provide a vaccine protecting against *S. pneumoniae* type 2, a serotype not covered by the currently commercialized vaccines.

It is the objective of the present invention to provide a saccharide of general formula (I) that is related to the *Streptococcus pneumoniae* serotype 2 capsular polysaccharide, as well as a conjugate of the saccharide of general formula (I) with an immunogenic carrier, such as a carrier protein. The saccharide of general formula (I), and particularly the conjugate of said saccharide with an immunogenic carrier is able to raise a protective immune response against *S. pneumoniae* serotype 2 in a human and/or animal host. Thus, a vaccine composition for immunization against *S. pneumoniae* type 2 comprising the saccharide of general formula (I), and/or a conjugate thereof is provided. Furthermore, the synthetic saccharide of general formula (I) is useful as marker in immunological assays for detection of antibodies against *Streptococcus pneumoniae* serotype 2 bacteria.

The objective of the present invention is solved by the teaching of the independent claims. Further advantageous features, aspects and details of the invention are evident from the dependent claims, the description, the figures, and the examples of the present application.

DESCRIPTION OF THE INVENTION

Definitions

The term "linker" as used herein encompasses molecular fragments capable of connecting the reducing-end monosaccharide of a saccharide with an immunogenic carrier or a solid support, optionally by binding to at least one interconnecting molecule. Thus, the function of the linker per se or together with the interconnecting molecule is to establish, keep and/or bridge a special distance between the reducing-end monosaccharide and an immunogenic carrier or a solid support. More specifically, one extremity of the linker is connected to the exocyclic oxygen atom at the anomeric center of the reducing-end monosaccharide and the other extremity is connected via the nitrogen atom with the interconnecting molecule, or directly with the immunogenic carrier or the solid support.

As used herein, the term "interconnecting molecule" refers to a bifunctional molecule containing functional group X and functional group Y, wherein functional group X is capable of reacting with the terminal amino group on the linker L and the functional group Y is capable of reacting with a functionality present on an immunogenic carrier or on a solid support. FIG. 1 displays examples of commercially available interconnecting molecules, but does not restrict the interconnecting molecules that can be used according to the present invention to the examples displayed herein.

The term "adjuvant" as used herein refers to an immunological adjuvant i.e. a material used in a vaccine composition that modifies or augments the effects of said vaccine by enhancing the immune response to a given antigen contained in the vaccine without being antigenically related to it. For the person skilled in the art, classically recognized examples of adjuvants include:

mineral-containing compositions, including calcium salts and aluminium salts (or mixtures thereof). Calcium salts include calcium phosphate. Aluminium salts include hydroxides, phosphates, sulfates, etc., with the salts taking any suitable form (e.g. gel, crystalline, amorphous, etc.). Adsorption to these salts is preferred. The mineral containing compositions may also be formulated as a particle of metal salt. The adjuvants known as aluminium hydroxide and aluminium phosphate may be also used. The invention can use any of the "hydroxide" or "phosphate" adjuvants that are in general used as adjuvants. The adjuvants known as "aluminium hydroxide" are typically aluminium oxyhydroxide salts, which are usually at least partially crystalline. The adjuvants known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt. Mixtures of both an aluminium hydroxide and an aluminium phosphate can be employed in the formulation according to the present invention;

saponins, which are a heterologous group of sterol glycosides and triterpenoid glycosides that are found in the bark, leaves, stems, roots and even flowers of a wide range of plant species. Saponins from the bark of the *Quillaia saponaria*, Molina tree have been widely studied as adjuvants. Saponins can also be commercially obtained from *Smilax ornata* (sarsaprilla), *Gypsophilla paniculata* (brides veil), and *Saponaria oficianalis* (soap root). Saponin adjuvant formulations include purified formulations, such as QS21, as well as lipid formulations, such as ISCOMs. Saponin compositions have been purified using HPLC and RP-HPLC. Specific purified fractions using these techniques have been identified, including QS7, QS 17, QS 18, QS2 1, QH-A, QH-B and QH-C. Saponin formulations may also comprise a sterol, such as cholesterol. Combinations of saponins and cholesterols can be used to form unique particles called immunostimulating complexes (ISCOMs). ISCOMs generally include a phospholipid such as phosphatidylethanolamine or phosphatidylcholine. Any known saponin can be used in ISCOMs. Preferably, the ISCOM includes one or more of QuilA, QHA & QHC;

microparticles (i.e. a particle of 100 nm to 150 pm in diameter, more preferably 200 nm to 30 pm in diameter, or 500 nm to 10 pm in diameter) formed from materials that are biodegradable and non-toxic. Such non-toxic and biodegradable materials include, but are not restricted to poly(α-hydroxy acid), polyhydroxybutyric acid, polyorthoester, polyanhydride, polycaprolactone;

CD1d ligands, such as an α-glycosylceramide, phytosphingosine-containing α-glycosylceramides, OCH, KRN7000 [(2S,3S,4R)-1-O-(α-D-galactopyranosyl)-2-(N-hexacosanoylamino)-1,3,4-octadecanetriol], CRONY-101, 3"-sulfo-galactosyl-ceramide;

immunostimulatory oligonucleotides, such CpG motif containing ones (a dinucleotide sequence containing an unmethylated cytosine residue linked by a phosphate bond to a guanosine residue), or CpI motif containing ones (a dinucleotide sequence containing cytosine linked to inosine), or a double-stranded RNA, or an oligonucleotide containing a palindromic sequence, or an oligonucleotide containing a poly(dG) sequence. Immunostimulatory oligonucleotides can include nucleotide modifications/analogs such as phosphorothioate modifications and can be double-stranded or (except for RNA) single-stranded;

compounds containing lipids linked to a phosphate-containing acyclic backbone, such as the TLR4 antagonist E5564;

oil emulsions (e.g. Freund's adjuvant).

Theoretically, each molecule or substance that is able to favor or amplify a particular situation in the cascade of immunological events, ultimately leading to a more pronounced immunological response, can be defined as an adjuvant.

In principle, through the use of adjuvants in vaccine formulations, one can direct and optimize immune responses that are appropriate or desirable for the vaccine;

enable mucosal delivery of vaccines, i.e. administration that results in contact of the vaccine with a mucosal surface such as buccal or gastric or lung epithelium and the associated lymphoid tissue;

promote cell-mediated immune responses;

enhance the immunogenicity of weaker immunogens, such as highly purified or recombinant antigens;

reduce the amount of antigen or the frequency of immunization required to provide protective immunity; and improve the efficacy of vaccines in individuals with reduced or weakened immune responses, such as newborns, the aged, and immunocompromised vaccine recipients.

Although little is known about their mode of action, it is currently believed that adjuvants augment immune responses by one of the following mechanisms:

increasing the biological or immunologic half-life of antigens;

improving antigen delivery to antigen-presenting cells (APCs), as well as antigen processing and presentation by the APCs e.g., by enabling antigen to cross endosomal membranes into the cytosol after ingestion of antigen-adjuvant complexes by APC;

mimicking danger inducing signals from stressed or damaged cells, which serve to initiate an immune response;

inducing the production of immunomodulatory cytokines;

biasing the immune response towards a specific subset of the immune system; and blocking the rapid dispersal of the antigen challenge.

Saccharides are known by the person skilled in the art as TI-2 (T cell independent-2) antigens and poor immunogens. Therefore, to produce a saccharide-based vaccine, said saccharide is conjugated to an immunogenic carrier to provide a conjugate, which presents an increased immunogenicity in comparison with the saccharide. In this context the term "immunogenic carrier" is defined as a structure, which is conjugated to the saccharide to form a conjugate that presents an increased immunogenicity in comparison with the saccharide per se. Thus, the conjugation of the saccharides to the immunogenic carrier has as effect the stimulation of the immune response against said saccharide, without inducing an immune response against the said immunogenic carrier.

Surprisingly, it was found that a pure saccharide of general formula (I) according to the present invention contains a protective immunogenic glycan epitope and is able to induce a protective immune response against $S.\ pneumoniae$ serotype 2 bacteria in a human and/or animal host. The saccharide of general formula (I) elicits antibodies that are cross-reacting with the $S.\ pneumoniae$ serotype 2 capsular polysaccharide (see for e.g. FIG. 5), recognize specifically $S.\ pneumoniae$ serotype 2 bacteria and opsonize them for killing by phagocytes.

Thus, the present invention relates to a saccharide of general formula (I)

$$V^*-U_{x+3}-U_{x+2}-U_{x+1}-U_x-O\text{-L-}NH_2 \quad (I)$$

wherein x is an integer selected from 1, 2, 3 and 4;

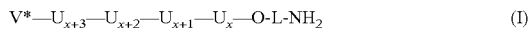

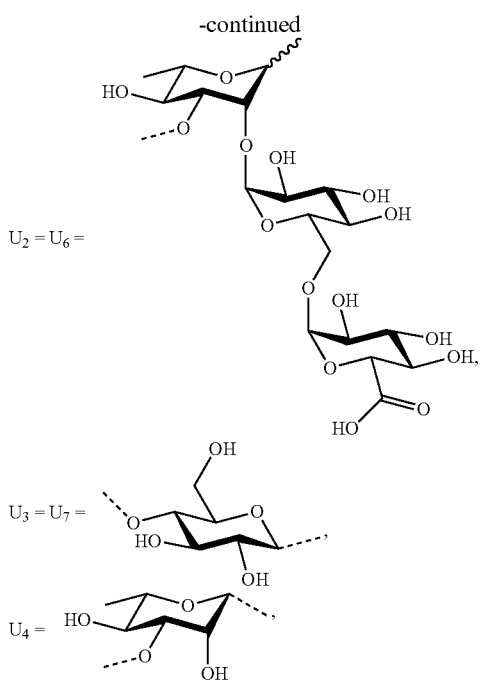

$V^*$— represents H—, H—$U_x$—, H—$U_{x+1}$—$U_x$—, H—$U_{x+2}$—$U_{x+1}$—$U_x$— or H—$U_{x+3}$—$U_{x+2}$—$U_{x+1}$—$U_x$—;

L represents a linker; or a pharmaceutically acceptable salt thereof.

-L- is defined as a linker and is part of the fragment —O-L-$NH_2$. Thus, the linker -L- is bound to an oxygen atom and to the nitrogen atom of the $NH_2$-group. It is preferred that at least two carbon atoms of the linker are between the oxygen atom and the $NH_2$-group, like —O—C—C—$NH_2$. The linker -L- can be an aliphatic chain, wherein the aliphatic chain can optionally include an aromatic chain inserted in it, or a number of heteroatoms oscillating from 0 to 10.

The linker L preferably contains between 2 and 40 carbon atoms (including the carbon atoms of optional side chains), more preferably between 2 and 30, more preferably between 2 and 20, more preferably between 2 and 14, more preferably between 2 and 12, and still more preferably between 2 and 10 carbon atoms.

The shortest atom chain between the oxygen atom (i.e. the oxygen of —O-L-$NH_2$) and the $NH_2$-group consists preferably of 2 to 14 atoms, more preferably of 2 to 12 atoms, more preferably of 2 to 10 atoms, more preferably of 2 to 8 atoms. In case the shortest chain (which is the shortest possible connection between the oxygen at the anomeric center and the $NH_2$-group) consists of 2 to 6 atoms, these are preferably carbon atoms. In case the shortest chain consists of 4 to 8 atoms, the chain may contain 1, 2 or 3 heteroatoms selected from O, N and S. In case the shortest chain consists of 9 to 14 atoms, the chain may contain 1, 2, 3, 4, 5, or 6 heteroatoms selected from O, N and S.

It is also preferred that the linker -L-, or the shortest chain is fully or partially fluorinated. The linker -L- may contain a 3-membered or a 4-membered or a 5-membered or a 6-membered saturated carbocycle or a 5-membered partly unsaturated (and not aromatic) carbocycle or a 4-membered or a 5-membered or a 6-membered saturated oxygen heterocycle or a 4-membered or a 5-membered or a 6-membered saturated nitrogen heterocycle or a 6-membered aromatic carbocycle.

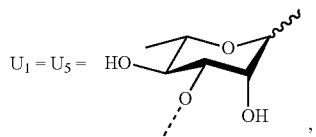

The linker -L- may also contain amide (—NH—CO—, —CO—NH—) and/or urea (—NH—CO—NH—) residues and preferably only one amide or urea residue. The linker may also contain substituents and preferably two substituents, such as $R^{10}$ and $R^{11}$, or four substituents such as $R^{10}$, $R^{11}$, $R^{15}$ and $R^{14}$, which have the meanings as defined herein and which are preferably selected from: —F, —Cl, —$CH_3$, —$C_2H_5$, —$C_3H_7$, —$C_5H_9$, —$C_6H_{13}$, —$OCH_3$, —$OC_2H_5$, —$CH_2F$, —$CHF_2$, —$CF_3$, —C(O)—$NH_2$, —$SCH_3$, —$SC_2H_5$, —NHC(O)$CH_3$, —N($CH_3$)$_2$, and —N($C_2H_5$)$_2$;

In case the linker -L- is fluorinated, more than two substituents —F are preferred.

Preferably the linker -L- is selected from: —$CH_2$—, —($CH_2$)$_2$—, —($CH_2$)$_3$—, —($CH_2$)$_4$—, —($CH_2$)$_5$—, —($CH_2$)$_6$—, —($CH_2$)$_7$—, —($CH_2$)$_8$—, —($CH_2$)$_9$—, —($CH_2$)$_{10}$—, —$CF_2$—, —($CF_2$)$_2$—, —($CF_2$)$_3$—, —($CF_2$)$_4$—, —($CF_2$)$_5$—, —($CF_2$)$_6$—, —($CF_2$)$_7$—, —($CF_2$)$_8$—, —($CF_2$)$_9$—, —($CF_2$)$_{10}$—, —($CH_2$)$_2$—O—($CH_2$)$_2$—, —$CH_2$—O—($CH_2$)$_3$—, —($CH_2$)$_3$—O—$CH_2$—, —$CH_2$—O—($CH_2$)$_2$—, —($CH_2$)$_2$—O—$CH_2$—, —($CH_2$)$_3$—O—($CH_2$)$_2$—, —($CH_2$)$_2$—O—($CH_2$)$_3$—, —($CH_2$)$_4$—O—$CH_2$—, —$CH_2$—O—($CH_2$)$_4$—, -$L^a$-, -$L^a$-$L^e$-, -$L^a$-$L^b$-$L^e$-, -$L^a$-$L^b$-$L^d$-$L^c$-$L^e$-, -$L^a$-$L^d$-$L^e$- wherein -$L^a$- is selected from: —($CH_2$)$_o$—, —($CF_2$)$_o$—, —$CH_2$—$CH_2$—O)$_o$—$C_2H_4$—, —($CH_2$—$CH_2$—O)$_o$—$CH_2$—, —($CR^{10}R^{11}$)$_o$—,

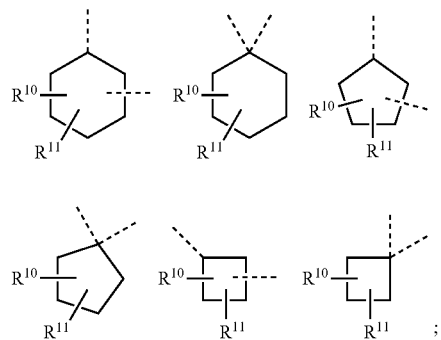

-$L^b$- and -$L^c$- are independently of each other selected from: —O—, —NH—C(O)—NH—, —NH—C(S)—NH—, —NH—C(O)—, —C(O)—NH—, —NH—C(O)—O—, —$NR^9$—, —$NR^{18}$—, —$SO_2$—,

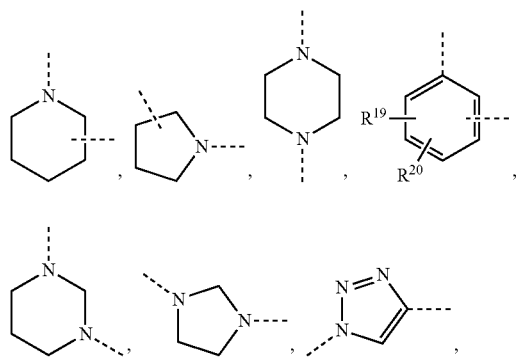

-continued

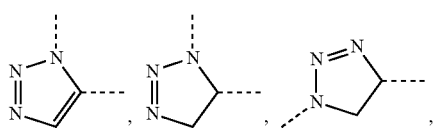

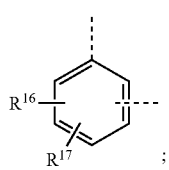

-$L^d$- represents —($CH_2$)$_q$—, —($CF_2$)$_q$—, —($CR^{12}R^{13}$)$_q$—, —($CH_2$—$CH_2$—O)$_q$—$C_2H_4$—, —($CH_2$—$CH_2$—O)$_q$—$CH_2$—,

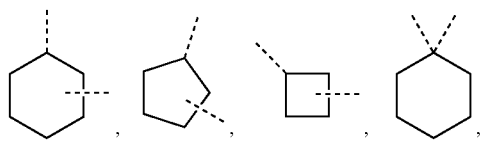

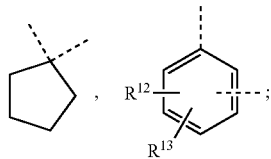

-$L^e$- is selected from: —($CH_2$)$_{p1}$—, —($CF_2$)$_{p1}$—, —$C_2H_4$—(O—$CH_2$—$CH_2$)$_{p1}$—, —$CH_2$—(O—$CH_2$—$CH_2$)$_{p1}$—, —($CH_2$)$_{p1}$—O—($CH_2$)$_{p2}$—, —($CR^{14}R^{15}$)$_{p1}$—, —($CR^{14}R^{15}$)$_{p1}$—O—($CR^{21}R^{22}$)$_{p2}$—,

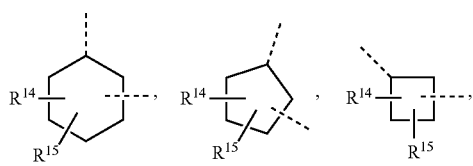

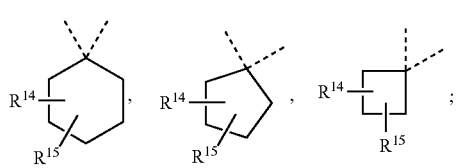

$R^9$ and $R^{18}$ are independently of each other selected from: —$CH_3$, —$C_2H_5$, —$C_3H_7$, and —$C(O)CH_3$;

$R^{10}$, $R^{11}$, $R^{12}$, $R^{13}$, $R^{14}$, $R^{15}$, $R^{16}$, $R^{17}$, $R^{19}$, $R^{20}$, $R^{21}$ and $R^{22}$ are independently of each other selected from: —H, —F, —Cl, —$CH_3$, —$C_2H_5$, —$C_3H_7$, —$C_5H_9$, —$C_6H_{13}$, —$OCH_3$, —$OC_2H_5$, —$CH_2F$, —$CHF_2$, —$CF_3$, —$C(O)$—$NH_2$, —$SCH_3$, —$SC_2H_5$, —$NHC(O)CH_3$, —$N(CH_3)_2$ and —$N(C_2H_5)_2$;

o, q, p1 and p2 are independently of each other an integer selected from 1, 2, 3, 4, 5, 6, 7, 8, 9, and 10.

The saccharides of the present invention bear basic and/or acidic substituents and they may form salts with organic or inorganic acids or bases.

Examples of suitable acids for such acid addition salt formation are hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphorsulfonic acid, china acid, mandelic acid, o-methylmandelic acid, hydrogen-benzenesulfonic acid, picric acid, adipic acid, d-o-tolyltartaric acid, tartronic acid, (o, m, p)-toluic acid, naphthylamine sulfonic acid, and other mineral or carboxylic acids well known to those skilled in the art. The salts are prepared by contacting the free base form with a sufficient amount of the desired acid to produce a salt in the conventional manner.

Examples of suitable inorganic or organic bases are, for example, NaOH, KOH, $NH_4OH$, tetraalkylammonium hydroxide, lysine or arginine and the like. Salts may be prepared in a conventional manner using methods well known in the art, for example by treatment of a solution of the compound of the general formula (I) with a solution of a base, selected out of the group mentioned above.

It is clear for the skilled person in the art of carbohydrate chemistry that the saccharides of general (I) are not containing —O—O— bonds and or sugar fragments ($U_x$, $U_{x+1}$, $U_{x+2}$, $U_{x+3}$) connected or bound to each other via their anomeric or C-1 carbons. It is also clear for the person skilled in the art that the stereochemistry of the glycosidic bond is the stereochemistry indicated for the anomeric center of the sugar fragment in the general formula. Hence, the stereochemistry of the anomeric center for sugar fragment $U_1$ and $U_5$ is α or β, for rhamnose residue in sugar fragment $U_2$ and $U_6$ is α or β, for sugar fragment $U_3$ and $U_7$ is β and for sugar fragment $U_4$ is β.

The saccharide of general formula (I) contains a protective immunogenic epitope and is able to induce a protective immune response against S. pneumoniae serotype 2 bacteria in a human and/or animal host. The saccharide of general formula (I) elicits antibodies that are cross-reacting with the S. pneumoniae serotype 8 capsular polysaccharide (see for e.g. FIG. 5), recognize specifically S. pneumoniae serotype 2 bacteria and opsonize them for killing by phagocytes. Additionally, the inventive saccharides have the advantage that these are pure synthesized compounds, which can be easily manufactured in accordance with GMP regulations.

Thus, the vaccine composition of the present invention contains most preferably only one single compound of the general formula (I) bound to an immunogenic carrier, preferably a carrier protein and more preferably $CRM_{197}$. Thus, the compound of the general formula (I) is useful for the preparation of well defined, well characterized and pure vaccines containing only one synthetically prepared and well characterized hexa-, hepta-, octa-, nona-. deca-, undeca- or dodecasaccharide preferably linked to an immunogenic carrier, preferably a carrier protein and more preferably $CRM_{197}$. Consequently, the vaccines of the present invention contain only one synthetically synthesized compound of general formulae (I) preferably linked to an immunogenic carrier, preferably a carrier protein and more preferably $CRM_{197}$.

Preferred is a saccharide of general formula (I), wherein x represents 1 and a pharmaceutically acceptable salt thereof. Hence, a saccharide of general formula (I-a)

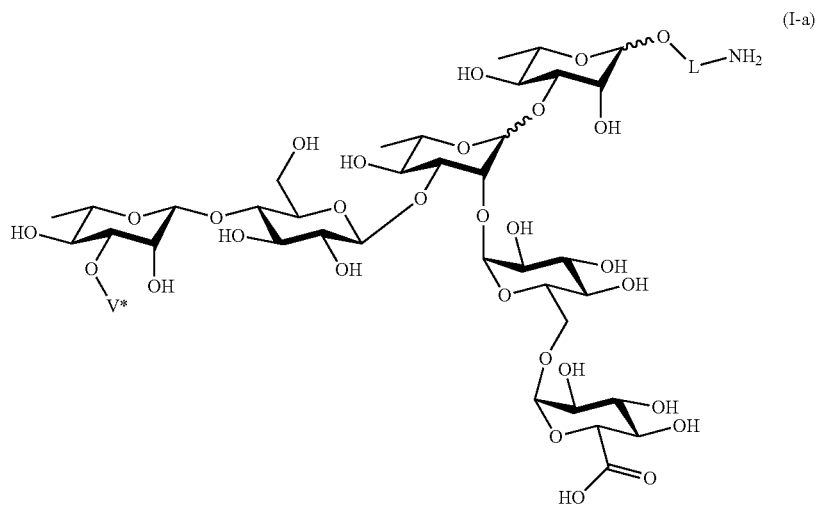

(I-a)

with L and V* having the meaning defined herein, or a pharmaceutically acceptable salt thereof is particularly preferred.

Also preferred is a saccharide of general formula (I), wherein x represents 2, 3 or 4, and a pharmaceutically acceptable salt thereof. Thus, a saccharide of general formula (I-b), (I-c) or (I-d)

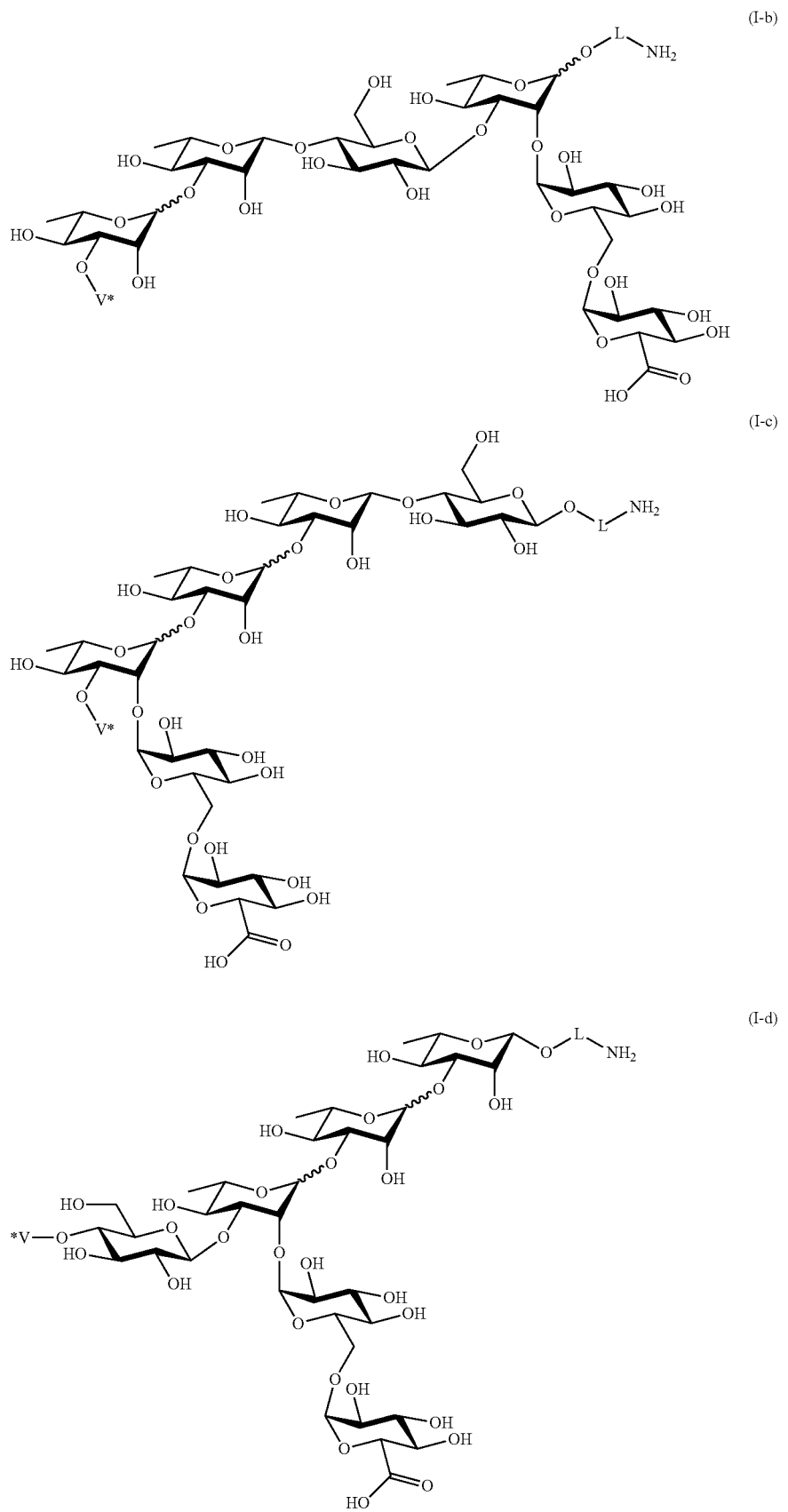

with L and V* having the meaning defined herein, or a pharmaceutically acceptable salt thereof are also preferred.

It is preferred that

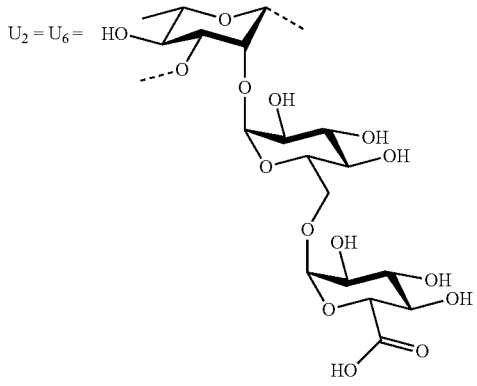

Thus, a saccharide of general formula (I), (I-a), (I-b), (I-c) or (I-d), wherein sugar fragment $U_2$ and $U_6$ has the stereochemistry β at the anomeric center of the rhamnose moiety is particularly preferred.

It is also preferred that

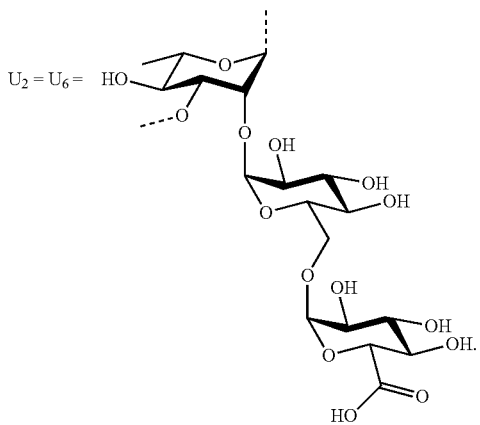

It is furthermore preferred that

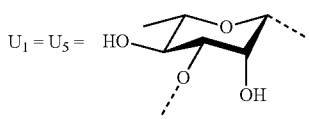

Thus, a saccharide of general formula (I), (I-a), (I-b), (I-c) or (I-d), wherein sugar fragment $U_1$ and/or $U_5$ has the stereochemistry β at its anomeric center is particularly preferred.

It is also preferred that

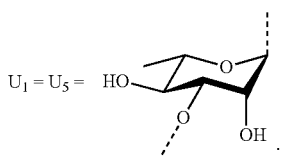

Thus, a saccharide of general formula (I), (I-a), (I-b), (I-c) or (I-d), wherein sugar fragment $U_1$ and/or $U_5$ has the stereochemistry α at its anomeric center is particularly preferred.

Preferably V*— represents H—. Thus, a saccharide of general formula (I), (I-a). (I-b), (I-c) or (I-d), wherein V*— represents H— is especially preferred.

Preferably the linker -L- is selected from: $-L^a-$, $-L^a-L^e-$, $-L^a-L^b-L^e-$, $-L^a-L^d-L^e-$; wherein $-L^a-$ is selected from: $-(CH_2)_o-$, $-(CH_2-CH_2-O)_o-C_2H_4-$, $-(CH_2-CH_2-O)_o-CH_2-$;

$-L^b-$ represents $-O-$;

$-L^d-$ is selected from: $-(CH_2)_q-$, $-(CF_2)_q-$, $-(CH_2-CH_2-O)_q-C_2H_4-$, and $-(CH_2-CH_2-O)_q-CH_2-$;

$-L^e-$ is selected from: $-(CH_2)_{p1}-$, $-(CF_2)_{p1}-$, $-C_2H_4-(O-CH_2-CH_2)_{p1}-$, $-CH_2-(O-CH_2-CH_2)_{p1}-$ and $-(CH_2)_{p1}-O-(CH_2)_{p2}-$;

and o, q, p1 and p2 are independently of each other an integer selected from 1, 2, 3, 4, 5, and 6.

Therefore, a saccharide of general formula (I), (I-a), (I-b), (I-c) or (I-d), wherein -L- is selected from: $-L^a-$, $-L^a-L^e-$, $-L^a-L^b-L^e-$ and $-L^a-L^d-L^e-$;

$-L^a-$ is selected from: $-(CH_2)_o-$, $-(CH_2-CH_2-O)_o-C_2H_4-$, $-(CH_2-CH_2-O)_o-CH_2-$;

$-L^b-$ represents $-O-$;

$-L^d-$ is selected from: $-(CH_2)_q-$, $-(CF_2)_q-$, $-(CH_2-CH_2-O)_q-C_2H_4-$, and $-(CH_2-CH_2-O)_q-CH_2-$;

$-L^e-$ is selected from: $-(CH_2)_{p1}-$, $-(CF_2)_{p1}-$, $-C_2H_4-(O-CH_2-CH_2)_{p1}-$, $-CH_2-(O-CH_2-CH_2)_{p1}-$ and $-(CH_2)_{p1}-O-(CH_2)_{p2}-$;

and o, q, p1 and p2 are independently of each other an integer selected from 1, 2, 3, 4, 5, and 6 is especially preferred.

Particularly preferred is a saccharide of general formula (I), (I-a), (I-b), (I-c) or (I-d), wherein -L- is selected from: $-L^a-$, $-L^a-L^e-$, $-L^a-L^b-L^e-$ and $-L^a-L^d-L^e-$;

$-L^a-$ is selected from: $-(CH_2)_o-$, $-(CH_2-CH_2-O)_o-C_2H_4-$, $-(CH_2-CH_2-O)_o-CH_2-$;

$-L^b-$ represents $-O-$;

$-L^d-$ is selected from: $-(CH_2)_q-$, $-(CF_2)_q-$, $-(CH_2-CH_2-O)_q-C_2H_4-$, and $-(CH_2-CH_2-O)_q-CH_2-$;

$-L^e-$ is selected from: $-(CH_2)_{p1}-$, $-(CF_2)_{p1}-$, $-C_2H_4-(O-CH_2-CH_2)_{p1}-$, $-CH_2-(O-CH_2-CH_2)_{p1}-$ and $-(CH_2)_{p1}-O-(CH_2)_{p2}-$;

o, q, p1 and p2 are independently of each other an integer selected from 1, 2, 3, 4, 5, and 6; and V*— represents H—.

It is particularly preferred that -L- represents $-(CH_2)_o-$ and o is an integer selected from 2, 3, 4, 5, 6, 7 and 8. Thus, a particularly preferred saccharide is a saccharide of general formula (I), (I-a), (I-b), (I-c) or (I-d), wherein -L- represents $-(CH_2)_o-$ and o is an integer selected from 2, 3, 4, 5, 6, 7 and 8.

Even more preferred is a saccharide of general formula (I), (I-a), (I-b), (I-c) or (I-d), wherein -L- represents —(CH$_2$)$_o$— and o is an integer selected from 2, 3, 4, 5, 6, 7 and 8 and V*— represents H—.

Preferably, the inventive saccharide is selected from: 5-amino pentyl β-L-rhamnopyranosyl-(1→4)-β-D-glucopyranosyl-(1→3)-α-L-{α-D-glucopyranosyluronate-(1→6)-α-D-glucopyranosyl-(1→2)} rhamnopyranosyl-(1→3)-α-L-rhamnopyranoside, 4-amino butyl β-L-rhamnopyranosyl-(1→4)-β-D-glucopyranosyl-(1→3)-α-L-{α-D-glucopyranosyluronate-(1→6)-α-D-glucopyranosyl-(1→2)} rhamnopyranosyl-(1→3)-α-L-rhamnopyranoside, 6-amino hexyl β-L-rhamnopyranosyl-(1→4)-β-D-glucopyranosyl-(1→3)-α-L-{α-D-glucopyranosyluronate-(1→6)-α-D-glucopyranosyl-(1→2)} rhamnopyranosyl-(1→3)-α-L-rhamnopyranoside, 7-amino heptyl β-L-rhamnopyranosyl-(1→4)-β-D-glucopyranosyl-(1→3)-α-L-{α-D-glucopyranosyluronate-(1→6)-α-D-glucopyranosyl-(1→2)} rhamnopyranosyl-(1→3)-α-L-rhamnopyranoside, 3-amino propyl β-L-rhamnopyranosyl-(1→4)-β-D-glucopyranosyl-(1→3)-α-L-{α-D-glucopyranosyluronate-(1→6)-α-D-glucopyranosyl-(1→2)} rhamnopyranosyl-(1→3)-α-L-rhamnopyranoside, 2-(2-aminoethoxy)ethyl β-L-rhamnopyranosyl-(1→4)-β-D-glucopyranosyl-(1→3)-α-L-{α-D-glucopyranosyluronate-(1→6)-α-D-glucopyranosyl-(1→2)} rhamnopyranosyl-(1→3)-α-L-rhamnopyranoside, and 2-amino ethyl β-L-rhamnopyranosyl-(1→4)-β-D-glucopyranosyl-(1→3)-α-L-{α-D-glucopyranosyluronate-(1→6)-α-D-glucopyranosyl-(1→2)} rhamnopyranosyl-(1→3)-α-L-rhamnopyranoside.

Chemical Synthesis

A saccharide of general formula (I) according to the present invention can be efficiently assembled using monosaccharides 1*, 2*, 3* and 4* as well as amino-alcohol linker 5* as starting material (Scheme 1).

Suitable amino protecting group include, but are not limited to tert-butyloxy carbonyl, 9-fluorenylmethoxy carbonyl, allyloxy carbonyl, 2,2,2-trichloroethyloxy carbonyl, benzyloxy carbonyl; carbonyls such as trifluoro acetyl, trichloro acetyl, acetyl, or benzoyl and aromatic alkyl such as benzyl, p-methoxybenzyl, p-methoxyphenyl, p-bromobenzyl, p-nitrophenyl, or 2-naphthylmethyl.

The protecting groups can be differentiated in "permanent protecting groups" and "temporary protecting groups". Permanent protecting groups are protecting groups that are stable during the entire synthesis and that can be efficiently removed at the late stage of the synthesis. The temporary protecting groups are generally orthogonal protecting groups that can be selectively removed at different levels of the synthesis to free hydroxyl groups for subsequent introduction of different substituents, including monosaccharides, other protecting groups or other residues present on the molecule.

The ingenious choice of protecting groups allows expedient access to a library of saccharides of general formula (I) functionalized with an amino group for subsequent conjugation to an immunogenic carrier or a solid support.

For expediently assembling the saccharide of general formula (I), protecting groups $P^1$, $P^2$, $P^6$, $P^7$, $P^8$ and $P^9$ are permanent protecting groups, protecting groups $P^{12}$, $P^{13}$, $P^{14}$ and $P^{15}$ represent temporary protecting groups and protecting group $P^{11}$ is either a permanent protecting group or a temporary permanent group.

It is particularly advantageous that $P^1$, $P^6$, $P^7$ and $P^9$ are benzyl groups, $P^2$ is an acetyl or benzoyl group, $P^8$ is a benzyloxy carbonyl, $P^{11}$ is a levulinoyl or a benzoyl group, Scheme 1: Retrosynthetic analysis.

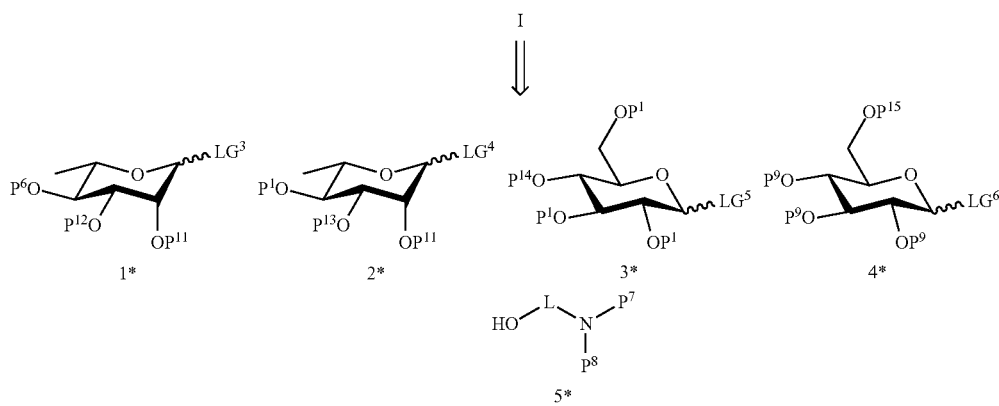

In Scheme 1, $P^1$, $P^6$-$P^9$, $P^{11}$-$P^{15}$ represent protecting groups, while $LG^3$-$LG^6$ represent leaving groups or temporary protecting groups.

The term "protecting group" as used herein refers to commonly used groups in organic synthesis for protection of amino and hydroxyl groups. Suitable hydroxyl protecting groups include, but are not limited to acetyl, benzyl, benzoyl, p-methoxybenzyl, p-methoxyphenyl, p-bromobenzyl, p-nitrophenyl, allyl, isopropyl, levulinoyl, dimethoxytrityl, trityl, 2-naphthylmethyl, pyvaloyl, triisopropylsilyl, tert-butyldimethylsilyl, tert-butyldiphenylsilyl, tert-butylmethoxphenylsilyl, triethylsilyl, trimethylsilyl, 2-trimethylsilylethoxymethyl, picolyl, 9-fluorenylmethoxy carbonyl.

$P^{12}$ is any hydroxyl protecting group orthogonal to $P^{11}$ and $P^6$, $P^{13}$ is any hydroxyl protecting group orthogonal to $P^1$, $P^{14}$ is any hydroxyl protecting group orthogonal to $P^1$ and $P^{15}$ is any hydroxyl protecting group orthogonal to $P^9$. Thus, a saccharide of general formula (I) can be advantageously synthesized starting from monosaccharides 1*-a, 1*-b, 2*-a, 3*-a, 3*-b, 4*-a and aminoalcohol linker 5*-a, wherein $P^{12}$ is any alcohol protecting group orthogonal to $P^{11}$ and benzyl, $P^{13}$ is any alcohol protecting group orthogonal to benzyl, $P^{14}$ is any alcohol protecting group orthogonal to benzyl and $P^2$, and $P^{15}$ is any alcohol protecting group orthogonal to benzyl (see Scheme 2).

Scheme 2: Retrosynthetic analysis

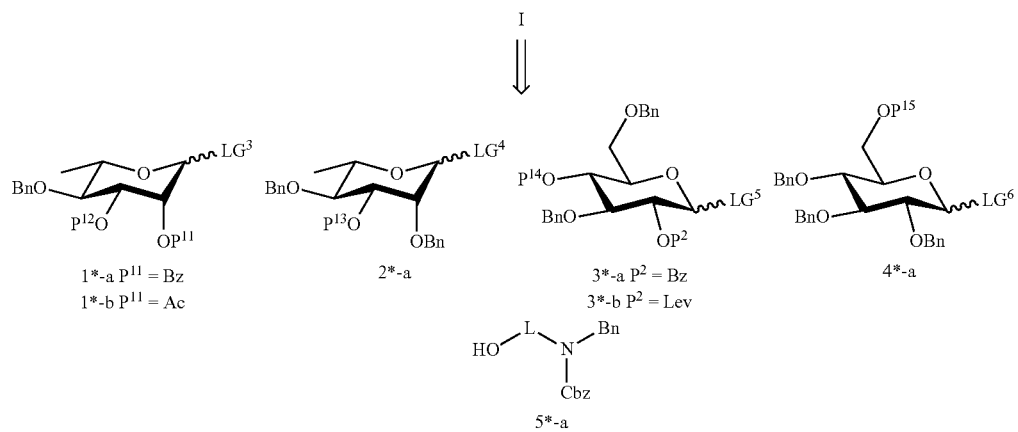

LG³-LG⁶ represent leaving groups including halides, thioethers, imidates, acetates, and phosphates, or OP¹⁶, wherein P¹⁶ is a temporary protecting group that is orthogonal to the other protecting groups on the molecule such as p-methoyphenyl, triethyl silyl, trimethyl silyl, t-butyldimethyl silyl, t-butyldiphenyl silyl, thexydimethylsilyl, and trimethyl silyl ethyl ($Me_3SiCH_2CH_2$).

Thus, starting from the building blocks 1*, 2*, 3*, 4* and 5*, but preferably from building blocks 1*-a, 1*-b, 2*-a, 3*-a, 3*-b, 4*-a and 5*-a, any saccharide of general formula (I) can be synthesized by linear synthesis or by modular synthesis via glycosylation, deprotection and/or protecting group conversion reactions.

Another aspect according to the present invention is directed to a method of synthesis of a saccharide of general formula (I)

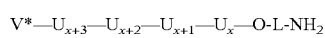

wherein

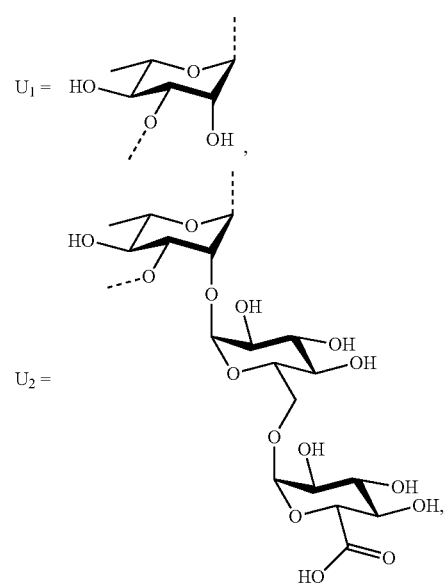

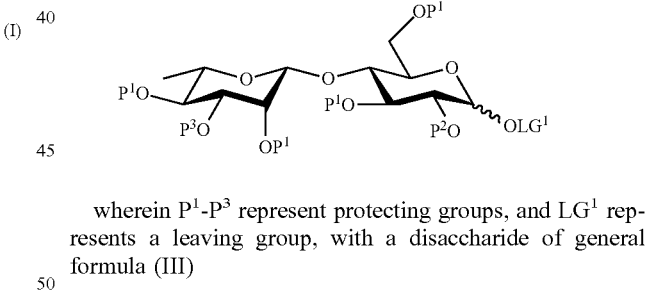

V*— represents H—, x represents 1 and linker L has the meaning defined herein comprising the following steps:

A) reacting a disaccharide of general formula (II)

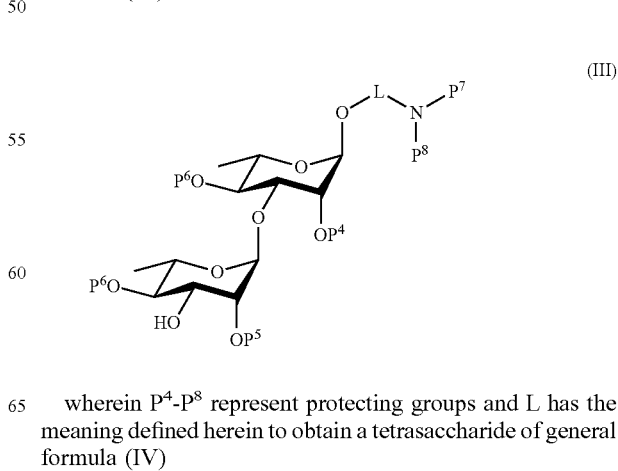

wherein $P^1$-$P^3$ represent protecting groups, and $LG^1$ represents a leaving group, with a disaccharide of general formula (III)

(III)

wherein $P^4$-$P^8$ represent protecting groups and L has the meaning defined herein to obtain a tetrasaccharide of general formula (IV)

(IV)

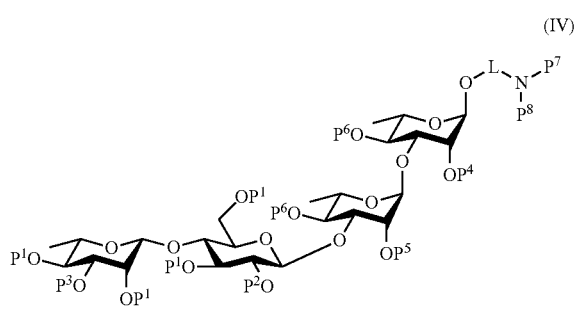

wherein $P^1$-$P^8$ represent protecting groups;

and

B) subjecting the tetrasaccharide of general formula (IV) to selective deprotection to obtain a compound of general formula (V)

(V)

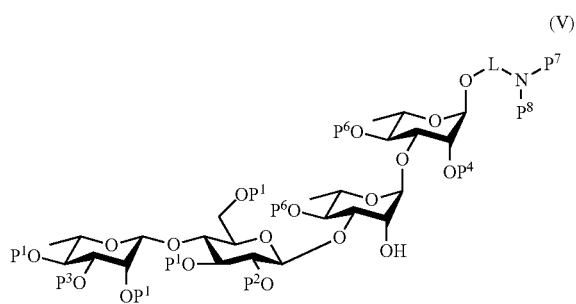

wherein $P^1$-$P^4$, $P^6$-$P^8$ represent protecting groups and L has the meaning defined herein;

and

C) reacting the disaccharide of general formula (V) with a compound of general formula (VI)

(VI)

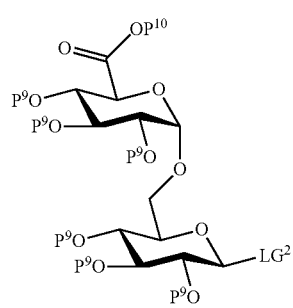

wherein $P^9$ and $P^{10}$ represent protecting groups and $LG^2$ represents a leaving group to obtain a hexasaccharide of general formula (VII)

(VII)

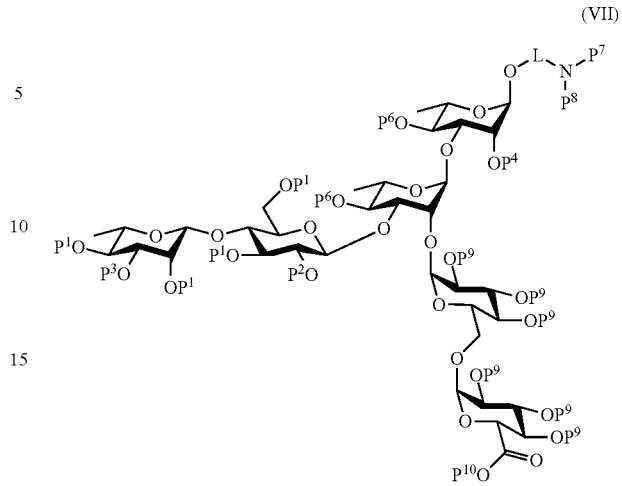

wherein $P^1$-$P^4$, $P^6$-$P^{10}$ represent protecting groups and L has the meaning defined herein;

and

D) performing the removal of protecting groups $P^1$-$P^4$, $P^6$-$P^{10}$ on the compound of general formula (VII).

The disaccharides of general formula (II), (III) and (VI) used as reagents in the method of the present invention can be assembled from the building blocks 1*, 2*, 3*, 4* and 5*, but preferably from building blocks 1*-a, 1*-b, 2*-a, 3*-a, 3*-b, 4*-a and 5*-a. For example, the disaccharide of general formula (II) can be synthesized starting from monosaccharides 2* and 3*, and preferably starting from monosaccharides 2*a and 3*a or 3*b, the disaccharide of general formula (III) can be synthesized starting from monosaccharide 1* and amino-alcohol 5*, but preferably starting from monosaccharide 1*a and/or 1*b and amino-alcohol 5*a.

$P^1$-$P^{10}$ represent protecting groups for amino group, hydroxyl group and carboxylic acid group, while $LG^1$ and $LG^2$ represent leaving groups.

Suitable hydroxyl protecting groups include, but are not limited to acetyl, benzyl, benzoyl, p-methoxybenzyl, p-methoxyphenyl, p-bromobenzyl, p-nitrophenyl, allyl, isopropyl, levulinyl, dimethoxytrityl, trityl, 2-naphthylmethyl, pyvaloyl, triisopropylsilyl, tert-butyldimethylsilyl, tert-butyldiphenylsilyl, tert-butylmethoxyphenylsilyl, triethylsilyl, trimethylsilyl, 2-trimethylsilylethoxymethyl, picoloyl, 9-fluorenylmethoxy carbonyl.

Suitable amino protecting groups include, but are not limited to tert-butyloxy carbonyl, 9-fluorenylmethoxy carbonyl, allyloxy carbonyl, 2,2,2-trichloroethyloxy carbonyl, benzyloxy carbonyl (Cbz), carbonyls such as trifluoro acetyl, trichloro acetyl, acetyl, or benzoyl and aromatic alkyl such as benzyl, p-methoxybenzyl, p-methoxyphenyl, p-bromobenzyl, p-nitrophenyl, or 2-naphthylmethyl.

A carboxylic acid can be protected as methyl ester, ethyl ester, allyl ester, isopropyl ester, tert-butyl ester, phenyl ester, benzyl ester or p-methoxybenzyl ester. Thus, protecting group $P^{10}$ can be a methyl, ethyl, allyl, isopropyl, tert-butyl, phenyl, benzyl or p-methoxybenzyl.

Suitable leaving groups include halides, thioethers, imidates, acetates, and phosphates.

To obtain high reaction yields and expedite the synthesis, it is advantageous that protecting groups $P^1$, $P^6$, $P^7$, $P^9$ represent benzyl groups, $P^8$ is a benzyloxy carbonyl group, $P^2$, $P^3$ and $P^4$ represent independently of each other an acetyl or benzoyl group and $P^5$ is any hydroxyl protecting group orthogonal to protecting groups $P^1$-$P^4$, $P^6$-$P^{10}$.

It is furthermore preferred that protecting group $P^5$ is a levulinoyl.

It is preferred that leaving groups $LG^1$ and $LG^2$ are selected from —$SCH_3$, —$SCH_2CH_3$, —$SPh$, —$OPO_3Bu_2$

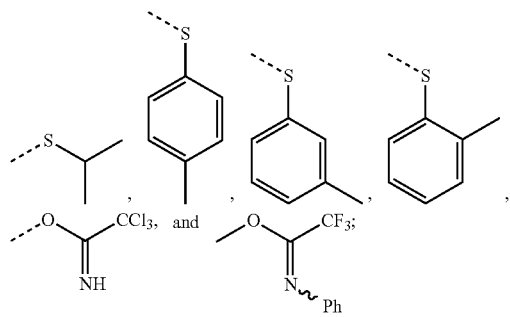

It is especially preferred that leaving group $LG^1$ is selected from

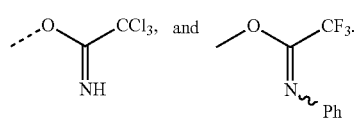

In such case, it is advantageous performing step A in presence of an imidate activating agent in an apolar solvent. Preferred apolar solvents are toluene, and halogenated solvents, such as chloroform and methylene chloride. Imidate activating agents are Lewis acids, such as silyl triflate or silver triflate. Examples of silyl triflate include, but are not restricted to trimethylsilyl trifluoromethanesulfonate, tert-butyl dimethyl trifluoromethanesulfonate, triiosopropyl trifluoromethanesulfonate. Preferably, the disaccharide of general formula (II) is reacted with a disaccharide of general formula (III) at a temperature of from about −60° C. to about 0° C., more preferably from about −40° C. to about 0° C.

It is also preferred that leaving group $LG^2$ is selected from: —$SCH_3$, —$SCH_2CH_3$,

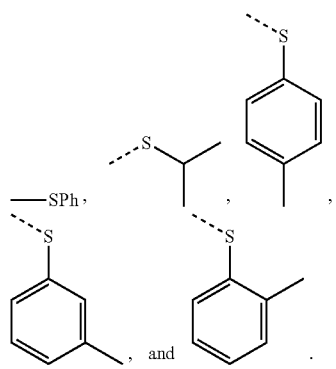

In such case, it is advantageous performing step C in presence of a thioether activating agents in a mixture of polar aprotic solvent and apolar solvent. Thioether activating agents include, but are not restricted to: NIS/TfOH, NIS/TMSOTf, NIS/$BF_3$.$Et_2O$, NIS/AgOTf, DMTST/$Tf_2O$, IDPC, BSP/$Tf_2O$, $Ph_2SO$/$Tf_2O$. Preferred polar aprotic solvents are tetrahydrofuran, diethyl ether and 1,4-dioxane. Preferred apolar solvents are toluene, halogenated solvents such as chloroform and methylene chloride. Preferred mixtures of apolar and polar aprotic solvent are: methylene chloride/1,4-dioxane, methylene chloride/tetrahydrofuran, methylene chloride/diethyl ether, toluene/diethyl ether, toluene/tetrahydrofuran. Preferably, the tetrasaccharide of general formula (V) is reacted with a disaccharide of general formula (VI) at a temperature of from about −60° C. to about 30° C., more preferably from about −45° C. to about 15° C., and even more preferably −30° C. to about 0° C.

The removal of protecting groups $P^1$-$P^4$, $P^6$-$P^{10}$ on the compound of general formula (VII) involves first removal of base-labile groups by treatment with a base in a mixture of polar aprotic and polar protic solvent; and second cleavage of the protecting groups sensitive to hydrogenation. For the first step suitable aprotic solvents include tetrahydrofuran, acetone, N,N-dimethylformamide, acetonitrile and N,N-dimethylsulfoxide, which are mixed with a suitable protic solvent such as water and alcohols including methanol, ethanol, propanol, isopropanol or tert-buthanol.

The basic cleavage of the protecting groups is preferably performed at temperatures comprised between 0° C. and room temperature. Appropriate base for performing first step include lithium hydroxide, sodium hydroxide, potassium hydroxide and sodium methoxide. The cleavage of the protecting groups sensitive to hydrogenation is conducted by exposure to hydrogen in presence of a hydrogenation catalyst in a mixture of polar protic and polar aprotic solvents at room temperature.

Intermediate

Another aspect of the present invention is directed to an intermediate of general formula (V)

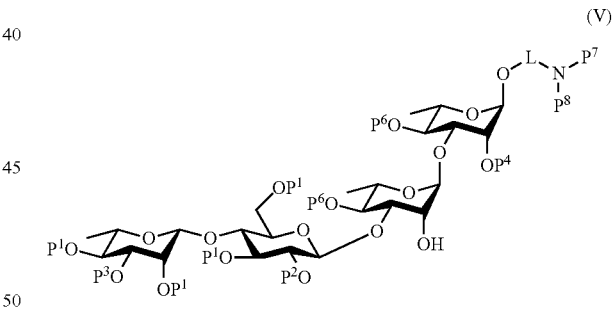

wherein $P^1$-$P^4$, $P^6$-$P^8$ represent protecting groups and L has the meaning defined herein. $P^1$-$P^4$, $P^5$ and $P^6$ are hydroxyl protecting groups, while $P^7$ and $P^8$ are amino protecting groups.

Suitable protecting groups for a hydroxyl group include, but are not limited to acetyl, benzyl, benzoyl, p-methoxybenzyl, p-methoxyphenyl, p-bromobenzyl, p-nitrophenyl, allyl, isopropyl, levulinyl, dimethoxytrityl, trityl, 2-naphthylmethyl, pyvaloyl, triisopropylsilyl, tert-butyldimethylsilyl, tert-butyldiphenylsilyl, tert-butylmethoxphenylsilyl, triethylsilyl, trimethylsilyl, 2-trimethylsilylethoxymethyl, picoloyl, 9-fluorenylmethoxy carbonyl.

Suitable protecting groups for an amino group include, but are not limited to tert-butyloxy carbonyl, 9-fluorenylmethoxy carbonyl, allyloxy carbonyl, 2,2,2-trichloroethyloxy carbonyl, benzyloxy carbonyl; carbonyls such as trifluoro acetyl, trichloro acetyl, acetyl, or benzoyl and aromatic alkyl such as benzyl, p-methoxybenzyl, p-methoxyphenyl, p-bromobenzyl, p-nitrophenyl, or 2-naphthylmethyl.

Preferred is an intermediate of general formula (V), wherein $P^1$, $P^6$ and $P^7$ represent a benzyl group, $P^2$, $P^3$ and $P^4$ are independently of each other selected from benzoyl and acetyl group, and $P^8$ represents a benzyloxy carbonyl (Cbz) group. Such intermediate can be efficiently coupled with a disaccharide of general formula (VI) to provide the hexasaccharide of general formula (VII).

Conjugate

Another aspect of the present invention is directed to a conjugate comprising a synthetic saccharide of general formula (I) covalently bound or covalently linked to an immunogenic carrier through the nitrogen atom of the —O-L-$NH_2$ group. In other words, another aspect of the present invention is directed to a saccharide of any of the general formulae (I), (I-a), (I-b), (I-c) or (I-d) conjugated with an immunogenic carrier through the nitrogen atom of the —O-L-$NH_2$ group. The inventive conjugate comprising a synthetic saccharide of the general formula (I), (I-a), (I-b), (I-c) or (I-d) covalently bound or covalently linked to an immunogenic carrier through the nitrogen atom of the —O-L-$NH_2$ group is also defined as a conjugate obtained by reacting a saccharide of any of the general formulae (I), (I-a), (I-b), (I-c) or (I-d) with an immunogenic carrier. Said conjugate proved to be efficient as a vaccine for immunization against diseases associated with Streptococcus pneumoniae serotype 2 bacteria.

Saccharides are known by the person skilled in the art as generally TI-2 (T cell independent-2) antigens and poor immunogens. TI-2 antigens are antigens, which are recognized only by mature B cells through the cross linking of surface exposed immunoglobulin receptors. Without T cell help, no immunological memory is generated and neither isotype switching from IgM to other IgG subclasses, nor B cells affinity maturation occurs. Moreover, saccharides are known as poor immunogens in humans due to the structural homology to human glycolipids and glycoproteins. Due to their poor immunogenic properties, saccharides manifest poor ability to produce both antibody production by B cells, as well as the formation of memory cells, features which are essential for the production of potent vaccines.

Therefore, to produce a potent saccharide-based vaccine, a saccharide of general formula (I), (I-a), (I-b), (I-c) or (I-d) is conjugated to an immunogenic carrier to provide a conjugate presenting increased immunogenicity in comparison with the saccharide.

Said conjugate consists of at least one synthetic saccharide of the general formula (I), (I-a), (I-b), (I-c) or (I-d) and an immunogenic carrier to which the at least one saccharide of the general formula (I), (I-a), (I-b), (I-c) or (I-d) is covalently bound.

Surprisingly, it was found that immunization with a conjugate according to the present invention results in the production of high titers of antibodies specific to the carbohydrate part of the saccharide according to the present invention. Said antibodies are cross-reacting with the natural S. pneumoniae serotype 2 capsular polysaccharide and present opsonophagocytic and bactericidal activity, thus conferring protection against S. pneumoniae serotype 2 bacteria.

In this context the term "immunogenic carrier" is defined as a structure, which is conjugated to the saccharide to form a conjugate that presents an increased immunogenicity in comparison with the saccharide per se. Thus, the conjugation of a saccharides of the general formula (I), (I-a), (I-b), (I-c) or (I-d) to the immunogenic carrier has as effect the stimulation of the immune response against the saccharide of the general formula (I), (I-a), (I-b), (I-c) or (I-d) without inducing an immune response against the said immunogenic carrier.

Preferred immunogenic carriers are carrier proteins or glycosphingolipids with immunomodulatory properties. For the person skilled in the art, a carrier protein is a protein selected from the group comprising or consisting of: a diphtheria toxoid, a mutated diphtheria toxoid, a modified diphtheria toxoid, a mutated and modified diphtheria toxoid, a tetanus toxoid, a modified tetanus toxoid, a mutated tetanus toxoid, outer membrane protein (OMP), bovine serum albumin (BSA), keyhole limpet hemocyanine (KLH), cholera toxoid (CT) and protein D (a non-typeable Haemophilus influenzae protein).

The term "toxoid" as used herein refers to a bacterial toxin (usually an exotoxin), whose toxicity has been inactivated or suppressed either by chemical (formalin) or heat treatment, while other properties, typically immunogenicity, are maintained. A mutated toxoid as used herein is a recombinant bacterial toxin, which has been amended to be less toxic or even non-toxic by amending the wild-type amino acid sequence. Such a mutation could be a substitution of one or more amino acids. Such a mutated toxoid presents on its surface a functionality that can react with the functional group Y of the interconnecting molecule to provide a modified toxoid. Said functionality is known to the person skilled in the art and includes, but is not restricted to the primary amino functionality of a lysine residue that can react with activated esters, an isocyanate group or an aldehyde in presence of a reducing agent, to the carboxylate functionality of a glutamate or aspartate residue that can be activated by carbodiimides or to the thiol functionality of a cysteine residue.

Activated esters include, but are not restricted to N-(γ-maleimidobutyryloxy) sulfosuccinimide ester (sulfo-GMBS), succinimidyl (4-iodoacetyl) aminobenzoate (sulfo-SIAB), succinimidyl-3-(bromoacetamido)propionate (SBAP), disuccinimidyl glutarate (DSG), disuccinimidyl adipate (DSA), 2-pyridyldithiol-tetraoxatetradecane-N-hydroxysuccinimide (PEG-4-SPDP), bis-(4-nitrophenyl) adipate and bis-(4-nitrophenyl) succinate (see FIG. 1). Preferred activated esters are disuccinimidyl adipate (DSA), disuccinimidyl glutarate (DSG), bis-(4-nitrophenyl) adipate and bis-(4-nitrophenyl) succinate.

The cysteine residue on the carrier protein can be converted to the corresponding dehydroalanine that can be further reacted with a suitable interconnecting molecule to provide modified carrier protein having on their surface the functional group X of the interconnecting molecule.

It is especially preferred that the inventive saccharides described herein are conjugated to the non-toxic mutated diphtheria toxin $CRM_{197}$ presenting as a functionality a primary amine functionality of a lysine residue.

$CRM_{197}$ like wild-type diphtheria toxin is a single polypeptide chain of 535 amino acids (58 kD) consisting of two subunits linked by disulfide bridges having a single amino acid substitution of glutamic acid for glycine. It is utilized as a carrier protein in a number of approved conjugate vaccines for diseases such as Prevnar.

Thus, in a preferred embodiment of the present invention the carrier protein presents on its surface primary amino functionalities of lysine residues that are able to react with the functional group Y of the interconnecting molecule to provide modified carrier protein having on their surface said functional group X of the interconnecting molecule, which is able to react with the terminal amino group of the linker functionalizing the inventive saccharides.

Said functional group X of the interconnecting molecules is selected from the group comprising or consisting of maleimide; α-iodoacetyl; α-bromoacetyl; and N-hydroxysuccinimide ester (NHS), aldehyde, imidoester, carboxylic acid, alkyl sulfonate, sulfonyl chloride, epoxide, anhydride, carbonate (see FIG. 2).

Preferred is a conjugate of general formula (X)

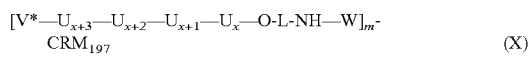

wherein m is comprised between about 2 and about 18;
—W— is selected from:

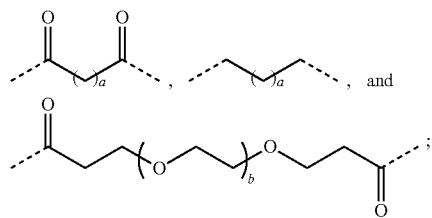

a represents an integer from 1 to 10;
b represents an integer from 1 to 4; and
$V^*$, $U_{x+3}$, $U_{x+2}$, $U_{x+1}$, $U_x$, x and L have the meanings defined herein.

As well known to the skilled person, "m" in structure X corresponds to the average load of saccharide units per unit of $CRM_{197}$ protein as determined by MALDI-TOF MS method using the molecular weight of $CRM_{197}$ as reference (see for e.g. FIG. 4). By varying the reaction conditions for the coupling of the saccharide according to the present invention to the $CRM_{197}$ carrier protein any conjugate of structure X with m being comprised between about 2 and about 18 can be obtained.

Preferably, the linker -L- is selected from: $-L^a-$, $-L^a-L^e-$, $-L^a-L^b-L^e-$, and $-L^a-L^d-L^e-$;

$-L^a-$ is selected from: $—(CH_2)_o—$, $—(CH_2—CH_2—O)_o—C_2H_4—$, $—(CH_2—CH_2—O)_o—CH_2—$;

$-L^b-$ represents $—O—$;

$-L^d-$ is selected from: $—(CH_2)_q—$, $—(CF_2)_q—$, $—(CH_2—CH_2—O)_q—C_2H_4—$, and $—(CH_2—CH_2—O)_q—CH_2—$;

$-L^e-$ is selected from: $—(CH_2)_{p1}—$, $—(CF_2)_{p1}—$, $—C_2H_4—(O—CH_2—CH_2)_{p1}—$, $—CH_2—(O—CH_2—CH_2)_{p1}—$ and $—(CH_2)_{p1}—O—(CH_2)_{p2}—$;

and o, q, p1 and p2 are independently of each other an integer selected from 1, 2, 3, 4, 5, and 6.

It is also preferred that —W— represents

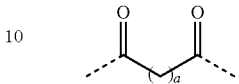

and a is an integer selected from 2, 3, 4, 5 and 6 is especially preferred.

Hence, a conjugate of general formula (X), wherein
the linker -L- is selected from: $-L^a-$, $-L^a-L^e-$, $-L^a-L^b-L^e-$, and $-L^a-L^d-L^e-$;

$-L^a-$ is selected from: $—(CH_2)_o—$, $—(CH_2—CH_2—O)_o—C_2H_4—$, $—(CH_2—CH_2—O)_o—CH_2—$;

$-L^b-$ represents $—O—$;

$-L^d-$ is selected from: $—(CH_2)_q—$, $—(CF_2)_q—$, $—(CH_2—CH_2—O)_q—C_2H_4—$, and $—(CH_2—CH_2—O)_q—CH_2—$;

$-L^e-$ is selected from: $—(CH_2)_{p1}—$, $—(CF_2)_{p1}—$, $—C_2H_4—(O—CH_2—CH_2)_{p1}—$, $—CH_2—(O—CH_2—CH_2)_{p1}—$ and $—(CH_2)_{p1}—O—(CH_2)_{p2}—$;

o, q, p1 and p2 are independently of each other an integer selected from 1, 2, 3, 4, 5, and 6;

—W— represents

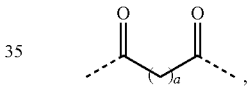

a is an integer selected from 2, 3, 4, 5 and 6 is especially preferred.

Even more preferred is a conjugate of general formula (X), wherein x represents 1. Thus, a conjugate of general formula (XI)

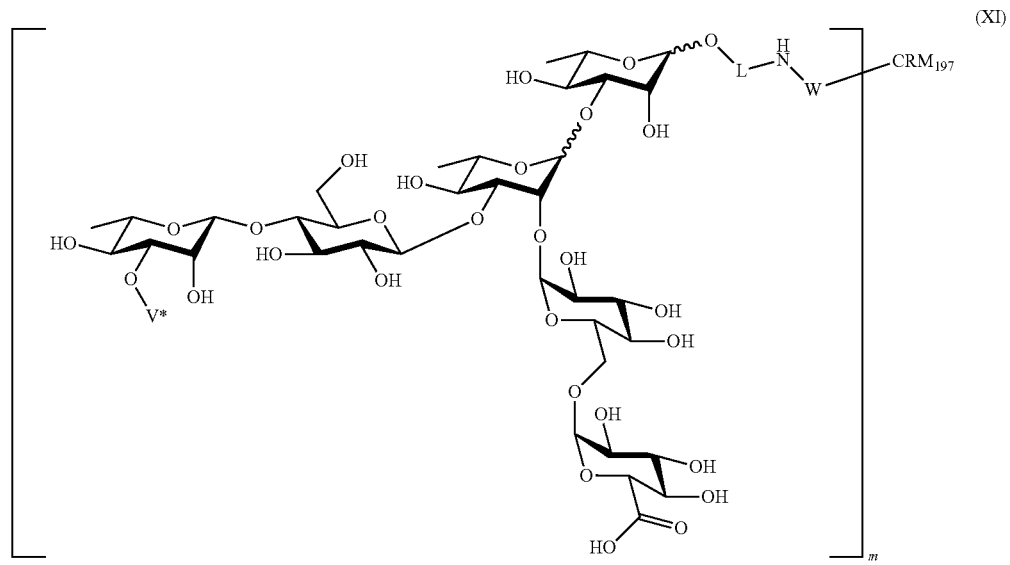

wherein m is comprised between about 2 and about 18;
—W— is selected from:

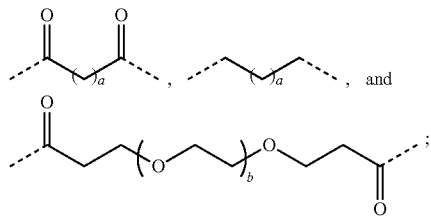, and a represents an integer from 1 to 10;
b represents an integer from 1 to 4;
V*— represents H—, H—U$_1$—, H—U$_2$—U$_1$—, H—U$_3$—U$_2$—U$_1$— or H—U$_4$—U$_3$—U$_2$—U$_1$—;
and L has the meaning defined herein.

Preferably, in general formula (XI) the linker -L- is selected from: -L$^a$-, -L$^a$-L$^e$-, -L$^a$-L$^b$-L$^e$-, and -L$^a$-L$^d$-L$^e$-
-L$^a$- is selected from: —(CH$_2$)$_o$—, —(CH$_2$—CH$_2$—O)$_o$—C$_2$H$_4$—, —(CH$_2$—CH$_2$—O)$_o$—CH$_2$—;
-L$^b$- represents —O—;
-L$^d$- is selected from: —(CH$_2$)$_q$—, —(CF$_2$)$_q$—, —(CH$_2$—CH$_2$—O)$_q$—C$_2$H$_4$—, and —(CH$_2$—CH$_2$—O)$_q$—CH$_2$—;
-L$^e$- is selected from: —(CH$_2$)$_{p1}$—, —(CF$_2$)$_{p1}$—, —C$_2$H$_4$—(O—CH$_2$—CH$_2$)$_{p1}$—, —CH$_2$—(O—CH$_2$—CH$_2$)$_{p1}$— and —(CH$_2$)$_{p1}$—O—(CH$_2$)$_{p2}$—;
o, q, p1 and p2 are independently of each other an integer selected from 1, 2, 3, 4, 5, and 6;
—W— represents

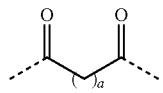

and a is an integer selected from 2, 3, 4, 5 and 6.

Especially preferred is a conjugate of general formula (X) or (XI), wherein the linker -L- represents —(CH$_2$)$_o$—,
o is an integer selected from 2, 3, 4, 5, 6, 7 and 8;
—W— represents

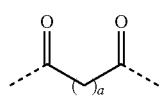

and a is an integer selected from 2, 3, 4, 5 and 6.

It is also preferred that V*— represents H— in general formulae (X) and (XI). Thus, particularly preferred is a conjugate of general formula (X) or (XI), wherein V*— represents H—, the linker -L- represents —(CH$_2$)$_o$—,
o is an integer selected from 2, 3, 4, 5, 6, 7 and 8;
—W— represents

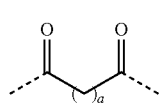

and a is an integer selected from 2, 3, 4, 5 and 6.

Preferably m is comprised between about 2 and about 18, more preferably between about 5 and about 15, even more preferably between about 8 and about 12.

In another embodiment, said immunogenic carrier is preferably a glycosphingolipid with immunomodulatory properties, and more preferably (2S,3S,4R)-1-(α-D-galactopyranosyl)-2-hexacosanoylaminooctadecane-3,4-diol. The term glycosphingolipid with immunomodulatory properties, as used herein, refers to a suitable glycosphingolipid capable of stimulating the immune system's response to a target antigen, but which does not in itself confer immunity as defined above.

Glycosphingolipids as used herein are compounds containing a carbohydrate moiety α-linked to a sphingolipid. Preferably, the carbohydrate moiety is a hexopyranose and most preferably is α-D-galactopyranose. For the person skilled in the art, sphingolipids are a class of lipids containing a C18 amino alcohol connected via an amide bond to a fatty acid. The C18 amino alcohol is preferably mono-, di- or polysubstituted with hydroxyl groups. Especially preferred, the C18 amino alcohol is phytosphingosine. The fatty acid is preferably a monocarboxylic acid having a saturated alkyl chain of a number of carbons ranging from 16 to 28 and more preferably from 18 to 26. Glycosphingolipids with immunomodulatory properties include, but they are not restricted to (2S,3S,4R)-1-(α-D-galactopyranosyl)-2-hexacosanoylaminooctadecane-3,4-diol, which can stimulate natural killer (NK) activity and cytokine production by natural killer T (NKT) cells and exhibits potent antitumor activity in vivo (*Proc. Natl Acad. Sci. USA*, 1998, 95, 5690).

The conjugates of the inventive saccharides with a glycosphingolipid with immunomodulatory properties have the advantage of being heat stable. To be suitable for conjugation, on the glycosphingolipid with immunomodulatory properties a functionality is introduced. Said functionality is prone to react directly with the terminal amino group of the linker of the inventive to provide conjugates of the saccharides or with the functional group Y of the interconnecting molecule to provide the modified glycosphingolipid with immunomodulatory properties.

Preferably, said functionality is introduced at the C6 of the carbohydrate moiety of the glycosphingolipid with immunomodulatory properties. Thus, the glycosphingolipid with immunomodulatory properties is functionalized with a functionality, which is prone of reacting with the terminal amino group of the saccharides or with the functional group Y of the interconnecting molecule. A functionality prone to react with an amino group includes, but it is not restricted to activated ester, isocyanate group, aldehyde, epoxide, imidoester, carboxylic acid, alkyl sulfonate and sulfonyl chloride. A functionality prone to react with the functional group Y of the interconnecting molecule so that to provide the modified glycosphingolipid with immunomodulatory properties presenting the functional group X of the interconnecting molecule includes, but it is not restricted to amine, alcohol, thiol, activated ester, isocyanate group, aldehyde, epoxide, vinyl, imidoester, carboxylic acid, alkyl sulfonate, sulfonyl chloride, vinyl group, alkynyl group and azido group.

Preferably, the functionality introduced at the C-6 position of the carbohydrate moiety of the glycosphingolipid with immunomodulatory properties is selected from the group comprising or containing an amine, a thiol, an alcohol, a carboxylic acid, a vinyl, maleimide, α-iodoacetyl, α-bromoacetyl, N-hydroxysuccinimide ester (NHS), 2-pyridyldithiols.

Said functional group X of the interconnecting molecules is selected from the group comprising or consisting of maleimide, α-iodoacetyl, α-bromoacetyl, N-hydroxysuccinimide ester (NHS), aldehyde, carboxylic acid, epoxyde, alkyl sulfonate, sulfonyl chloride, anhydride, carbonate.

Preferably, di(N-succinimidyl) adipate or bis(4-nitrophenyl) adipate is first reacted with a synthetic saccharide having a primary amino group. Activated saccharide is subsequently condensed with a glycosphingolipid, which is modified at C-6 position by an interconnecting molecule having a terminal amino functionality in order to afford the conjugate.

As used herein, the term "interconnecting molecule" refers to a bifunctional molecule containing functional group X and functional group Y, wherein functional group X is capable of reacting with the terminal amino group on the linker -L- and the functional group Y is capable of reacting with a functionality present on the immunogenic carrier or on the solid support.

It was found that the saccharide of general formula (I), (I-a), (I-b), (I-c) and (I-d) covalently linked or covalently bound to an immunogenic carrier through the nitrogen atom of the —O-L-NH$_2$ group or in other words the conjugate obtained by reacting a saccharide of general formula (I), (I-a), (I-b), (I-c) and (I-d) with an immunogenic carrier, and especially a conjugate of general formula (X), and (XI) elicits a protective immune response in a human and/or animal host, and therefore is useful in the prevention and/or treatment of a disease caused by S. pneumoniae serotype 2. Such disease includes pneumonia, meningitis, otitis media, bacteremia and acute exacerbation of chronic bronchitis, sinusitis, arthritis and conjunctivitis.

Vaccine Composition

A further aspect of the present invention relates to a vaccine composition containing at least one synthetic saccharide and/or a pharmaceutically acceptable salt thereof according to the present invention and/or a conjugate comprising a saccharide according to the present invention covalently linked to an immunogenic carrier, preferably to CRM$_{197}$ carrier protein, through the nitrogen atom of the —O-L-NH$_2$ group together with at least one pharmaceutically acceptable adjuvant and/or excipient.

In a preferred embodiment, said vaccine composition further comprises at least one of capsular polysaccharide of Streptococcus pneumoniae and/or a fragment of a capsular polysaccharide of Streptococcus pneumoniae and/or conjugate of a carrier protein and a capsular polysaccharide of Streptococcus pneumoniae or a fragment of a capsular polysaccharide of Streptococcus pneumoniae, wherein Streptococcus pneumoniae is selected from the group comprising Streptococcus pneumoniae, wherein the Streptococcus pneumoniae is selected from the group comprising or consisting of Streptococcus pneumoniae type 4, 6B, 9V, 14, 18C, 19F and 23F, preferably type 1, 3, 4, 5, 6A, 6B, 7F, 9V, 14, 18C, 19F and 23F, and more preferably serotypes 1, 3, 4, 5, 6A, 6B, 7F, 8, 9N, 9V, 10A, 11A, 14, 15B, 17F, 18C, 19F, 19A, 20, 22F, 23F and 33F.

Such a vaccine composition is particularly advantageous since it provides simultaneously protection against S. pneumoniae type 2 and other serotypes that are specific for a certain population.

The term "adjuvant" as used herein refers to an immunological adjuvant i.e. a material used in a vaccine composition that modifies or augments the effects of said vaccine by enhancing the immune response to a given antigen contained in the vaccine without being antigenically related to it. For the persons skilled in the art, classically recognized examples of immunological adjuvants include, but are not restricted to oil emulsions (e.g. Freund's adjuvant), saponins, aluminium or calcium salts (e.g. alum), non-ionic block polymer surfactants, and many others.

Vaccine compositions are preferably in aqueous form, particularly at the point of administration, but they can also be presented in non-aqueous liquid forms or in dried forms e.g. as gelatin capsules, or as lyophilisates, etc.

Vaccine compositions may include one or more preservatives, such as thiomersal or 2-phenoxyethanol. Mercury-free compositions are preferred, and preservative-free vaccines can be prepared.

Vaccine compositions may include a physiological salt, such as a sodium salt e.g. to control tonicity. Sodium chloride (NaCl) is typical and may be present at between 1 and 20 mg/ml. Other salts that may be present include potassium chloride, potassium dihydrogen phosphate, disodium phosphate dehydrate, magnesium chloride, calcium chloride, etc.

Vaccine compositions can have an osmolality of between 200 mOsm/kg and 400 mOsm/kg.

Vaccine compositions may include compounds (with or without an insoluble metal salt) in plain water (e.g. w.f.i.), but will usually include one or more buffers. Typical buffers include: a phosphate buffer; a Tris buffer; a borate buffer; a succinate buffer; a histidine buffer (particularly with an aluminium hydroxide adjuvant); or a citrate buffer. Buffer salts will typically be included in the 5-20 mM range.

Vaccine compositions typically have a pH between 5.0 and 9.5 e.g. between 6.0 and 8.0.

Vaccine compositions are preferably sterile and gluten free.

Vaccine compositions are suitable for administration to animal (and, in particular, human) patients, and thus include both human and veterinary uses. They may be used in a method of raising an immune response in a patient, comprising the step of administering the composition to the patient.

The vaccine compositions of the present invention may be administered before a subject is exposed to a Streptococcus pneumoniae type 2 and/or after a subject is exposed to a Streptococcus pneumoniae type 2.

Vaccine compositions may be prepared in unit dose form. In some embodiments a unit dose may have a volume of between 0.1-1.0 mL e.g. about 0.5 mL.

Vaccine compositions of the invention may be prepared in various forms. For example, the vaccine compositions may be prepared as injectables, either as liquid solutions or suspensions. Solid forms suitable for solution in, or suspension in, liquid vehicles prior to injection can also be prepared (e.g. a lyophilized composition or a spray-freeze dried composition). The composition may be prepared for topical administration e.g. as an ointment, cream or powder. The composition may be prepared for oral administration e.g. as a tablet or capsule, as a spray, or as a syrup (optionally flavored). The composition may be prepared for pulmonary administration e.g. by an inhaler, using a fine powder or a spray. The composition may be prepared as a suppository. The composition may be prepared for nasal, aural or ocular administration e.g. as a spray or drops. Injectables for intramuscular administration are typical.

The pharmaceutical compositions may comprise an effective amount of an adjuvant i.e. an amount which, when administered to an individual, either in a single dose or as part of a series, is effective for enhancing the immune response to a co-administered S. pneumoniae type 2 antigen. This amount can vary depending upon the health and physical condition of the individual to be treated, age, the taxonomic group of individual to be treated (e.g. non-human primate, primate, etc.), the capacity of the individual's immune system to synthesize antibodies, the degree of protection desired, the formulation of the vaccine, the treating doctor's assessment of the medical situation, and other relevant factors. The amount will fall in a relatively broad range that can be determined through routine trials.

Techniques for the formulation and administration of the vaccine of the present invention may be found in "Remington's Pharmaceutical Sciences" Mack Publishing Co., Easton Pa.

A therapeutically effective dosage of one conjugate according to the present invention or of one saccharide of general formula (I) refers to that amount of the compound that results in an at least a partial immunization against a disease. Toxicity and therapeutic efficacy of such compounds can be determined by standard pharmaceutical, pharmacological, and toxicological procedures in cell cultures or experimental animals. The dose ratio between toxic and therapeutic effect is the therapeutic index. The actual amount of the composition administered will be dependent on the subject being treated, on the subject's weight, the severity of the affliction, the manner of administration and the judgement of the prescribing physician.

Immunological Assay

A further embodiment of the present invention is directed to a saccharide according to the present invention for use as marker in immunological assays for detection of antibodies against *Streptococcus pneumoniae* type 2. Such assay comprises, for instance, microarray and ELISA.

Hence, the inventive saccharide can be used for diagnosis of diseases caused by *S. pneumoniae* serotype 2. An assay conducted for diagnostic purposes according to the invention may be an immune assay like a solid-phase enzyme immunoassay (EIA), an enzyme linked immunosorbent assay (ELISA), especially an "indirect" ELISA or a radioimmune assay (RIA). Preferably, the saccharide according to the present invention is covalently linked on the solid support through an interconnecting molecule. Thus, the saccharide according to the present invention can be covalently linked on the solid support directly or indirectly through the nitrogen atom of the —O-L-NH$_2$ group. The solid support is preferably selected from the group comprising or consisting of: a glass slide, a microtitre plate, test tubes, microspheres, nanoparticle or beads.

It is particularly preferred that the solid support is a glass slide or a microtitre plate. A microtitre plate or microplate or microwell plate is a flat plate with multiple "wells" used as small test tubes. Typically, a microtitre plate having 6, 24, 96, 384 or even 1536 sample wells can be used. Microplates are produced from many different materials, like polycarbonate for microtitre plate used for PCR. The most common is polystyrene as used for most optical detection microplates. It can be colored white by the addition of titanium dioxide for optical absorbance or luminescence detection or black by the addition of carbon for fluorescent biological assays.

DESCRIPTION OF THE FIGURES

As shown in FIG. 5B immunization with conjugate CRM$_{197}$-hexasaccharide 2 induces specific antibodies recognizing the core glycan structures being present in *S. pneumoniae* serotype 2. Generated antibodies are specific for serotype 2 since they crossreact to the native serotype 2 capsular polysaccharides, but not with control SP19F polysaccharides or polysaccharides contained in bacterial cell wall.

FIG. 6 shows the induction of substantial serotype 2-specific antibody titers in mice following a repeated immunization with conjugate CRM$_{197}$ hexasaccharide 2 in the presence of aluminium hydroxide (A) and significant killing of immune-sera opsonized bacteria (B). Clearly detectable OPKA was also observed with sera being induced in the absence of aluminium hydroxide during the immunization protocol. These results show that conjugate CRM$_{197}$-hexasaccharide 2 containing vaccines are highly immunogenic and induce functional antibodies in mice.

FIG. 7 shows that immunization only with conjugate CRM$_{197}$-hexasaccharide 2 leads to a significant reduction of bacterial colony forming units (CFU) and, thus, increased number of protected mice following challenge with the pathogenic *S. pneumoniae* serotype 2 strain D39. In two body compartments of infected mice analyzed, lung (A) and blood (B), a partial (A) or a complete bacterial elimination (B) following challenge infection was observed.

Figure 1:
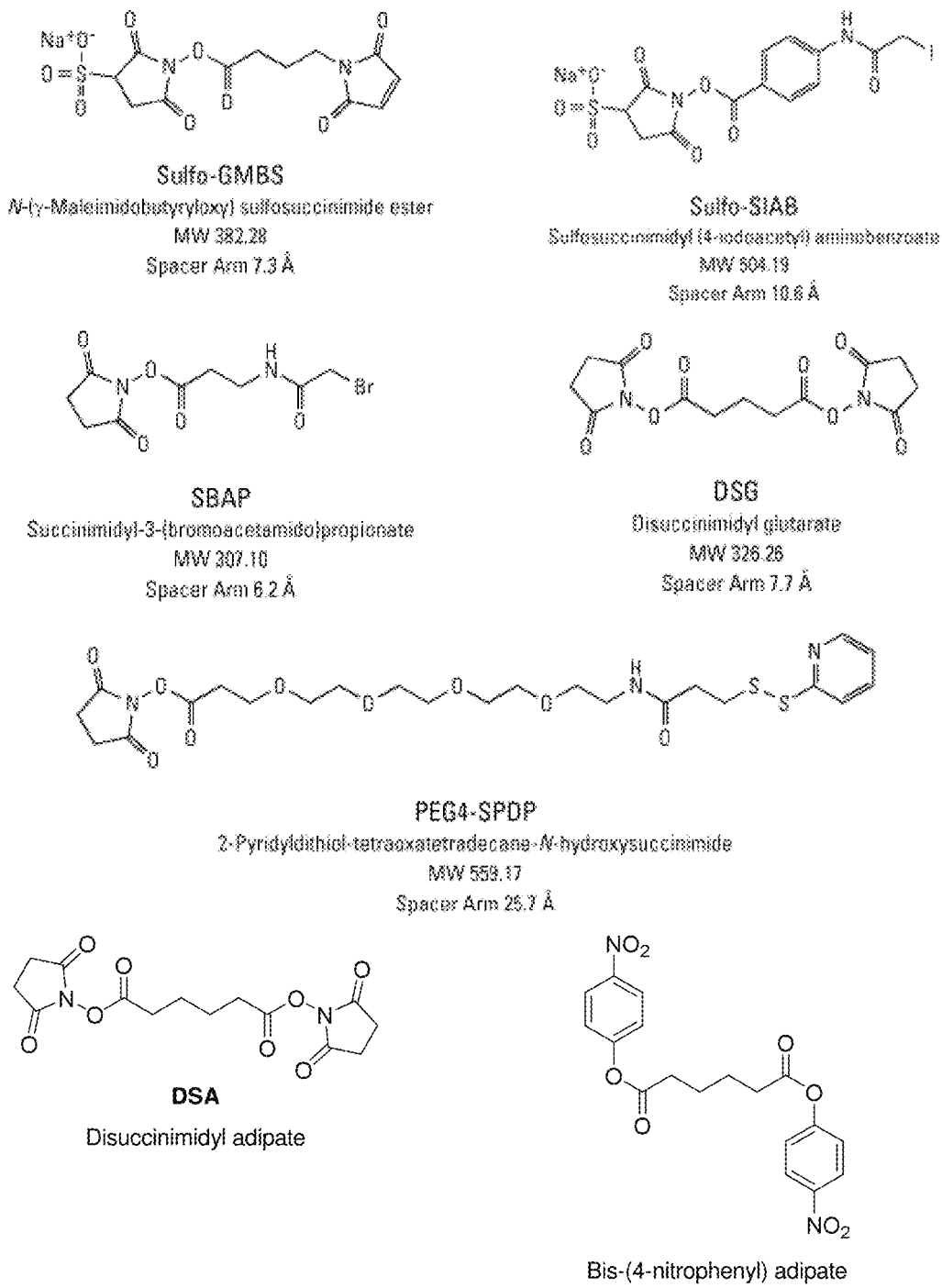
FIG. 1: Commercially available interconnecting molecules according to the present invention.
Figure 1:
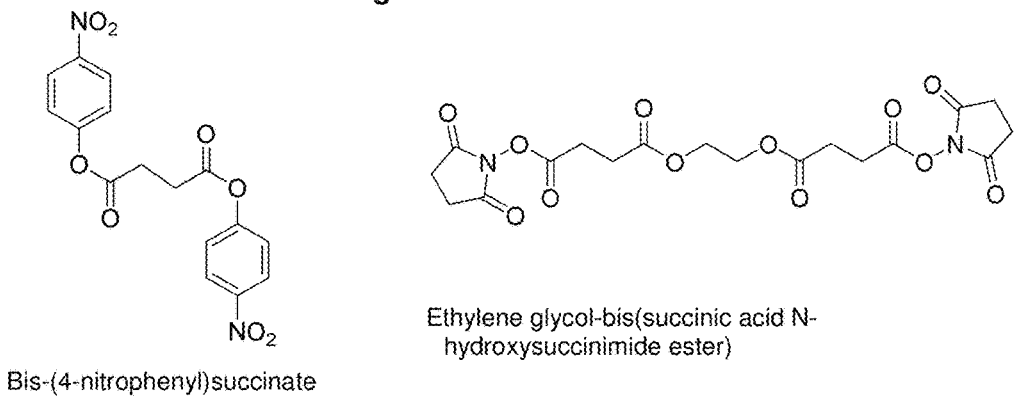
Figure 2:
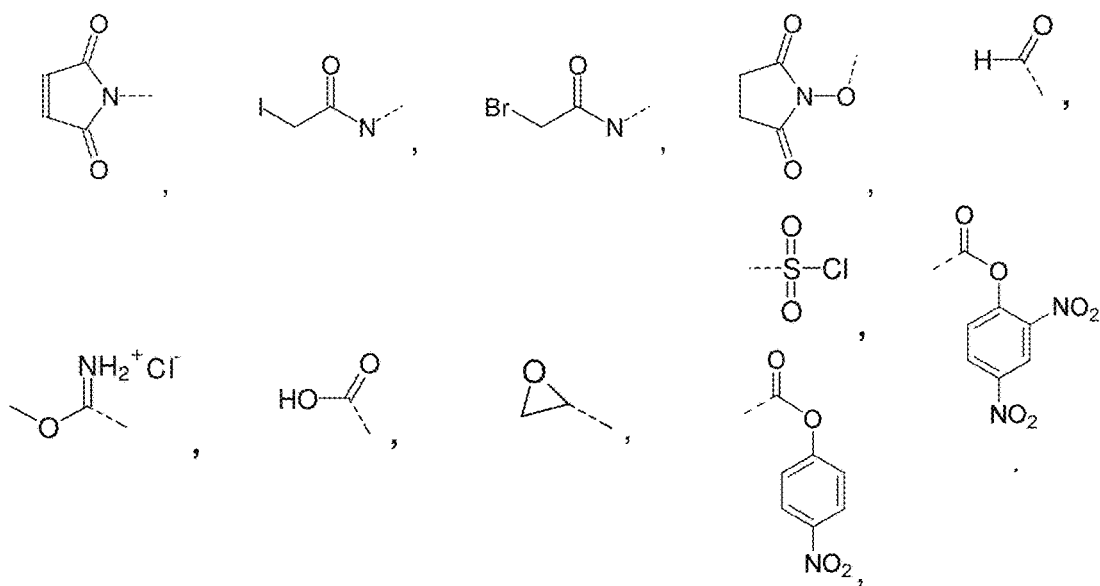
FIG. 2: Examples of functional group X of the interconnecting molecule according to the present invention.
Figure 3:
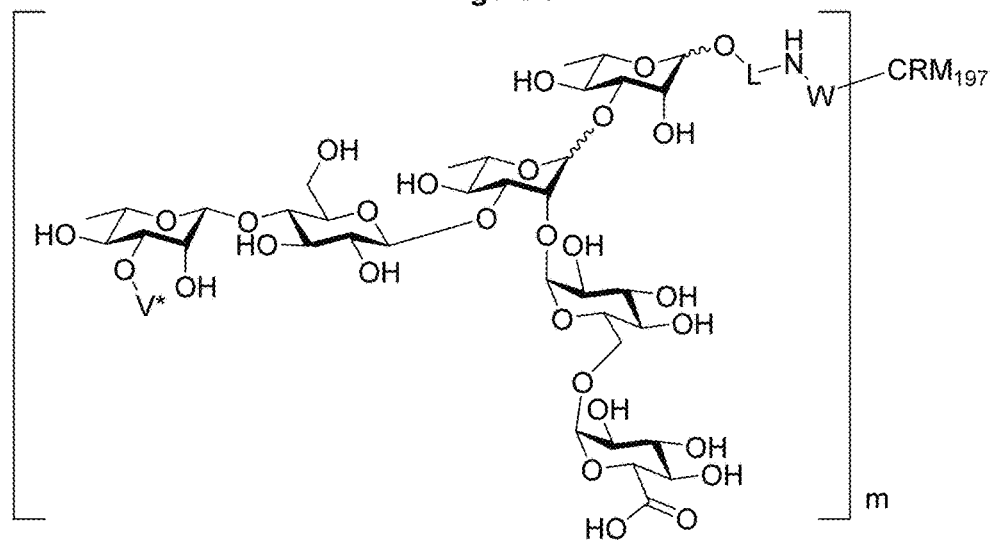
FIG. 3: Shows a CRM$_{197}$ conjugate of the present invention.

The following examples are included to demonstrate preferred embodiments of the invention. It should be appreciated by those skilled in the art that the techniques disclosed in the examples, which follow represent techniques discovered by the inventor to function well in the practice of the invention, and thus can be considered to constitute preferred modes for its practice. However, those skilled in the art should, in light of the present disclosure, appreciate that many changes can be made in the specific embodiments, which are disclosed and still obtain a like or similar result.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention.

EXAMPLES

A. Chemical Synthesis

General Information

Commercial grade solvents were used unless stated otherwise. Dry solvents were obtained from a Waters Dry Solvent System. Solvents for chromatography were distilled prior to use. Sensitive reactions were carried out in heat-dried glassware and under an argon atmosphere. Analytical thin layer chromatography (TLC) was performed on Kieselgel 60 F254 glass plates precoated with a 0.25 mm thickness of silica gel. Spots were visualized by staining with vanillin solution [6% (w/v) vanillin and 10% (v/v) sulfuric acid in 95% EtOH] or Hanessian's stain [5% (w/v) ammonium molybdate, 1% (w/v) cerium (II) sulfate and 10% (v/v) sulfuric acid in water]. Silica column chromatography was performed on Fluka Kieselgel 60 (230-400 mesh). $^1$H, $^{13}$C and two-dimensional NMR spectra were measured with a Varian 400-MR, 600-MR and Bruker Avance 700 spectrometer at 296 K. Chemical shifts (δ) are reported in parts per million (ppm) relative to the respective residual solvent peaks (CDCl$_3$: δ 7.26 in $^1$H and 77.16 in $^{13}$C NMR; D$_2$O: δ 4.79 in $^1$H NMR). The following abbreviations are used to indicate peak multiplicities: s singlet; d doublet; dd doublet of doublets; t triplet; dt doublet of triplets; q quartet; m multiplet. Coupling constants (J) are reported in Hertz (Hz). High resolution mass spectrometry (HRMS) was performed at the Free University Berlin, Mass Spectrometry Core Facility, with an Agilent 6210 ESI-TOF mass spectrometer.

ABBREVIATIONS

Ac Acetyl
AcOH Acetic acid
Ac$_2$O Acetic anhydride
BAIB Bisacetyliodobenzene
Bn Benzyl
$^t$BuOH t-Butanol
Bz Benzoyl
CAN Cericammonium nitrate
Cbz Benzyloxycarbonyl
Cu(OAc)$_2$ Copper(II) acetate
DBU 1,8-Diazabicyclo[5.4.0]undec-7-ene
DCC N,N'-Dicyclohexylcarbodiimide
DCM Dichloromethane
DMAP N,N-Dimethylaminopyridine
DMF N,N'-Dimethylformamide
ESI Electrosprayionization
Et$_3$N Triethylamine
Et Ethyl
EtOAc Ethyl acetate
FmocCl 9-Fluorenylmethylchloroformate
g Grams
h Hours
HRMS High resolution mass spectrometry
Lev Levulinyl
min Minute
mL Millilitre
Me Methyl
MeI Methyl iodide
MeOH Methanol
MP p-Methoxy phenyl
MS Molecular sieves
NaHCO$_3$ Sodium bicarbonate
NaOH Sodium hydroxide
NaOMe Sodium methoxide
NIS N-Iodo succinimide
NMR Nuclear magnetic resonance
Pd/C Palladium on charcoal
Ph Phenyl
Pico Picoloyl
CPS Capsular polysaccharide
Py Pyridine
RT Room temperature
TCA Trichloroacetamide
TEMPO 2,2,6,6-Tetramethylpiperidinyloxy
TfOH Trifluoromethanesulfonic acid
TMSOTf Trimethylsilyltrifluromethanesulfonate
THF Tetrahydrofuran
Tol p-Tolyl Example A.1: Synthesis of Disaccharide Acceptor 8

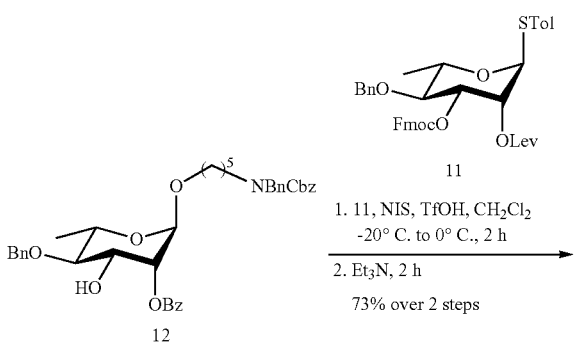

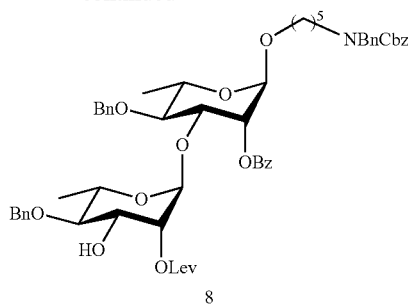

8

Synthesis of Building Block 14

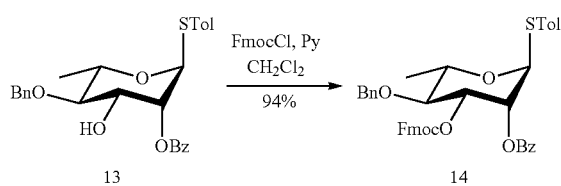

To a clear solution of 13 (Dhenin S. G. Y. et al., *Org. Biomol. Chem.* 2009, 7, 5184) (6.7 g, 14.4 mmol) in CH$_2$Cl$_2$ (80 mL) were added FmocCl (5.6 g, 21.62 mmol), and pyridine (2.4 mL, 28.8 mmol) and stirred at room temperature for 12 h. After complete consumption of starting material, the reaction mixture was diluted with CH$_2$Cl$_2$ (80 mL) and washed successively with 1 M HCl (60 mL), water (60 mL) and aq. sat. NaHCO$_3$ (60 mL). The organic layer was dried over Na$_2$SO$_4$, filtered and concentrated. The crude was purified by flash chromatography using hexanes and ethyl acetate as eluent (9:1) to afford the desired product 14 as white foam (9.3 g, 94%).

H NMR (400 MHz, CDCl$_3$) δ 8.06 (d, J=7.7 Hz, 2H), 7.78-7.67 (m, 2H), 7.63 (t, J=7.5 Hz, 1H), 7.58-7.52 (m, 2H), 7.49 (t, J=7.6 Hz, 2H), 7.44-7.05 (m, 13H), 5.89 (s, 1H), 5.49 (s, 1H), 5.29 (dd, J=9.5, 3.2 Hz, 1H), 4.87 (d, J=11.1 Hz, 1H), 4.71 (d, J=11.1 Hz, 1H), 4.61-4.48 (m, 1H), 4.41 (dq, J=12.2, 6.5 Hz, 1H), 4.28 (d, J=6.0 Hz, 2H), 3.76 (t, J=9.6 Hz, 1H), 2.32 (s, 3H), 1.42 (d, J=6.1 Hz, 3H);

$^{13}$C NMR (101 MHz, CDCl$_3$) δ 165.6, 154.3, 143.7, 143.2, 141.4, 141.3, 138.2, 137.9, 133.6, 132.7, 130.1, 130.0, 129.7, 129.6, 128.6, 128.5, 128.1, 128.0 (2C), 127.9, 127.3, 127.2, 125.5, 125.2, 120.1 (2C), 86.2, 78.8, 76.8, 75.4, 72.1, 70.4, 69.1, 46.8, 21.3, 18.1; HRMS (ESI): Calcd for C$_{42}$H$_{38}$O$_7$S [M+Na]+709.2236, found: 709.2238.

Synthesis of Building Block 12

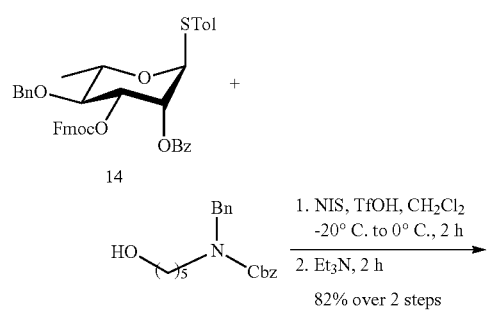

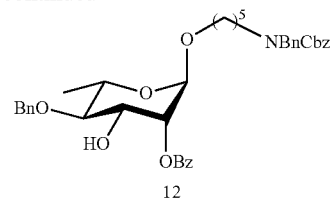

12

A solution of compound 14 (0.17 g, 0.25 mmol), aminopentyl linker 15 (0.16 g, 0.5 mmol) and 4 Å acid washed molecular sieves (AWMS) (0.3 g) in CH$_2$Cl$_2$ (5 mL) were stirred at room temperature for 30 min. The solution was cooled to −20° C. and NIS (62 mg, 0.28 mmol), and TfOH (2.5 μL, 0.028 mmol) were added. The reaction mixture was gradually brought to room temperature over 2 h. After complete consumption of starting material, Et$_3$N (2 mL) was added and the reaction mixture was stirred at room temperature for another 2 h. Reaction mixture was diluted with CH$_2$Cl$_2$ (25 mL) and washed with aq. sat. Na$_2$S$_2$O$_3$ (10 mL). Separated organic layer was dried over Na$_2$SO$_4$, filtered and concentrated. The crude was purified by flash chromatography using hexanes and ethyl acetate as eluent (4:1) to obtain the desired product 12 as colorless oil (0.135 g, 82%).

$^1$H NMR (400 MHz, CDCl$_3$) δ 8.06 (d, J=7.7 Hz, 2H), 7.59 (q, J=9.3, 8.4 Hz, 1H), 7.47 (t, J=7.6 Hz, 2H), 7.42-7.13 (m, 15H), 5.32 (s, 1H), 5.18 (d, J=12.1 Hz, 2H), 4.86 (d, J=11.1 Hz, 1H), 4.83-4.79 (m, 1H), 4.75 (d, J=11.1 Hz, 1H), 4.51 (d, J=6.4 Hz, 2H), 4.21 (s, 1H), 3.78 (d, J=8.1 Hz, 1H), 3.62 (d, J=16.6 Hz, 1H), 3.46 (t, J=9.4 Hz, 1H), 3.42-3.13 (m, 2H), 2.16 (s, 1H), 1.70-1.42 (m, 6H), 1.39 (d, J=6.2 Hz, 3H);

$^{13}$C NMR (101 MHz, CDCl$_3$) δ 174.0, 166.4, 133.5, 130.0, 129.8, 128.7, 128.6, 128.2, 128.1, 128.0, 127.4, 125.3, 110.1, 97.4, 81.9, 75.4, 73.5, 70.7, 67.6, 67.3, 50.4, 29.2, 18.3; HRMS (ESI): Calcd for C$_{40}$H$_{45}$O$_8$N [M+K]+ 706.2782, found: 706.2705.

Synthesis of Building Block 11

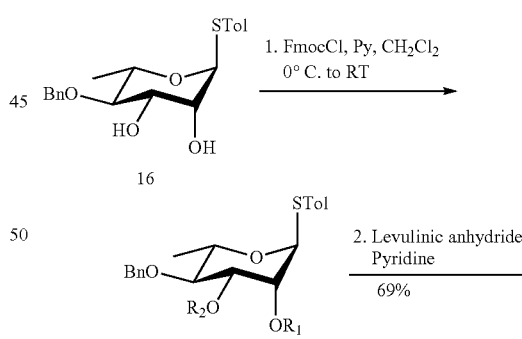

Pyridine (0.8 mL, 10.0 mmol) was added dropwise at 0° C. to a stirred solution of 16 (Rajput V. K. *J. Org. Chem.* 2008, 73, 6924) (2.4 g, 6.6 mmol) and FmocCl (1.8 g, 7.0 mmol) in CH$_2$Cl$_2$ (50 mL). The mixture was gradually heated to room temperature over 2 h, and diluted CH$_2$Cl$_2$ (100 mL), washed successively with 1 M HCl (50 mL) and water (50 mL). The organic layer was dried over Na$_2$SO$_4$, filtered and concentrated. The crude was purified by flash chromatography using hexanes and ethyl acetate as eluent (10:1 to 4:1) to obtain 24a (0.92 g, 24%) and 24b (1.3 g, 34%; 20% of 16 was recovered).

$^1$H NMR (400 MHz, CDCl$_3$) δ 7.78 (d, J=7.5 Hz, 2H), 7.71 (t, J=8.4 Hz, 2H), 7.42 (t, J=8.3 Hz, 4H), 7.38-7.28 (m, 7H), 7.13 (d, J=7.8 Hz, 2H), 5.39 (d, J=3.5 Hz, 1H), 4.86-4.71 (m, 3H), 4.56-4.42 (m, 2H), 4.36 (t, J=7.6 Hz, 1H), 3.88 (dt, J=8.2, 3.6 Hz, 1H), 3.49 (t, J=9.2 Hz, 1H), 3.41 (dd, J=9.5, 5.8 Hz, 1H), 2.34 (s, 3H), 1.46 (d, J=6.0 Hz, 3H); $^{13}$C NMR (101 MHz, CDCl$_3$) δ 155.8, 143.5, 141.5, 138.3, 138.2, 132.5, 130.2, 130.0, 128.8, 128.2 (2C), 128.0, 127.4, 127.3, 125.6, 125.5, 120.2, 120.1, 85.7, 80.9, 77.9, 76.2, 75.6, 74.3, 70.7, 46.9, 21.3, 18.4; HRMS (ESI): Calcd for C$_{35}$H$_{34}$O$_6$S [M+Na]+605.1974, found: 609.1993.

Levulinic anhydride (1.4 g, 6.69 mmol) and pyridine (0.54 mL, 6.69 mmol) were added to a stirred solution of 24b (1.3 g, 2.23 mmol) in CH$_2$Cl$_2$ (20 mL). After stirring at room temperature for 2 days, the reaction mixture was diluted with CH$_2$Cl$_2$ (50 mL) and washed successively with 1 M HCl (50 mL) and aq. sat. NaHCO$_3$ (50 mL). The organic layer was dried over Na$_2$SO$_4$, filtered and concentrated. The crude was purified by flash chromatography using hexanes and ethyl acetate as eluent (4:1) to obtain 11 as viscous oil (1.04 g, 69%).

$^1$H NMR (400 MHz, CDCl$_3$) δ 7.77 (d, J=7.6 Hz, 2H), 7.61 (dd, J=15.4, 7.5 Hz, 2H), 7.45-7.27 (m, 11H), 7.12 (d, J=7.8 Hz, 2H), 5.62 (dd, J=3.2, 1.6 Hz, 1H), 5.33 (d, J=1.6 Hz, 1H), 5.16 (dd, J=9.7, 3.3 Hz, 1H), 4.83 (d, J=11.0 Hz, 1H), 4.67 (d, J=11.0 Hz, 1H), 4.51 (dd, J=10.3, 6.7 Hz, 1H), 4.42-4.24 (m, 3H), 3.62 (t, J=9.5 Hz, 1H), 2.80-2.65 (m, 4H), 2.33 (s, 3H), 2.15 (s, 3H), 1.36 (d, J=6.2 Hz, 3H); $^{13}$C NMR (101 MHz, CDCl$_3$) δ 206.1, 171.8, 154.1, 143.6, 143.1, 141.3, 141.2, 138.1, 137.8, 132.6, 129.9, 129.5, 128.4, 127.9, 127.8 (2C), 127.2, 127.1, 125.2, 125.1, 120.1, 120.0, 85.8, 78.6, 76.3, 75.3, 71.7, 70.1, 68.9, 46.7, 37.9, 29.8, 28.0, 21.1, 17.8; HRMS (ESI): Calcd for C$_{40}$H$_{40}$O$_8$S [M+Na]+703.2342, found: 703.2359.

Synthesis of Disaccharide Acceptor 8

A solution of donor 11 (0.25 g, 0.37 mmol), acceptor 12 (0.165 g, 0.25 mmol) and 4 Å acid washed molecular sieves (AWMS) (0.3 g) in CH$_2$Cl$_2$ (5 mL) were stirred at room temperature for 30 min. The solution was cooled to −200C and NIS (83 mg, 0.37 mmol), TfOH (3.3 µL, 0.037 mmol) were added. The reaction mixture was gradually brought to room temperature over 2 h. After complete consumption of starting material, Et$_3$N (2 mL) was added and the reaction mixture was stirred at room temperature for another 2 h. Reaction mixture was diluted with CH$_2$Cl$_2$ and washed with aq. sat. Na$_2$S$_2$O$_3$. The organic layer was dried over Na$_2$SO$_4$, filtered and concentrated. The crude was purified by flash chromatography using hexanes and ethyl acetate as eluent (3:1) to obtain the desired product 8 as colorless oil (0.18 g, 73%).

$^1$H NMR (400 MHz, CDCl$_3$) δ 8.05 (d, J=7.7 Hz, 2H), 7.60 (t, J=7.4 Hz, 1H), 7.48 (t, J=7.6 Hz, 2H), 7.39-7.18 (m, 20H), 5.32 (s, 1H), 5.24-5.12 (m, 3H), 4.87 (d, J=10.8 Hz, 1H), 4.83-4.76 (m, 2H), 4.76-4.55 (m, 3H), 4.50 (d, J=4.8 Hz, 2H), 4.26-4.15 (m, 1H), 3.97 (dd, J=9.5, 3.4 Hz, 1H), 3.77 (dd, J=9.7, 6.0 Hz, 2H), 3.57 (t, J=9.4 Hz, 2H), 3.24 (dd, J=19.8, 10.2 Hz, 4H), 2.75 (q, J=6.4, 5.8 Hz, 2H), 2.60 (qd, J=16.7, 8.1 Hz, 2H), 2.18 (s, 3H), 1.64-1.43 (m, 6H), 1.31 (d, J=6.2 Hz, 3H), 1.18 (d, J=6.2 Hz, 3H); $^{13}$C NMR (101 MHz, CDCl$_3$) δ 207.1, 172.2, 166.0, 138.4, 138.0, 133.4, 129.9, 129.8, 128.6 (2C), 128.5 (2C), 128.51, 128.4, 128.3, 128.0, 127.7 (2C), 127.3, 99.5, 97.0, 81.4, 80.5, 77.9, 77.4, 75.7, 74.1, 73.0, 69.9, 68.3, 67.8, 67.3, 50.6, 50.3, 47.2, 46.3, 38.3, 29.9, 29.2, 28.3, 23.5, 18.2, 17.9; HRMS (ESI): Calcd for C$_{58}$H$_{67}$O$_{14}$N [M+Na]+ 1024.4459, found: 1024.4321.

Applying the synthetic procedures described at example A.1 to linker building blocks 15a, 15b, 15c and 15d provides disaccharides 8a, 8b, 8c and 8d.

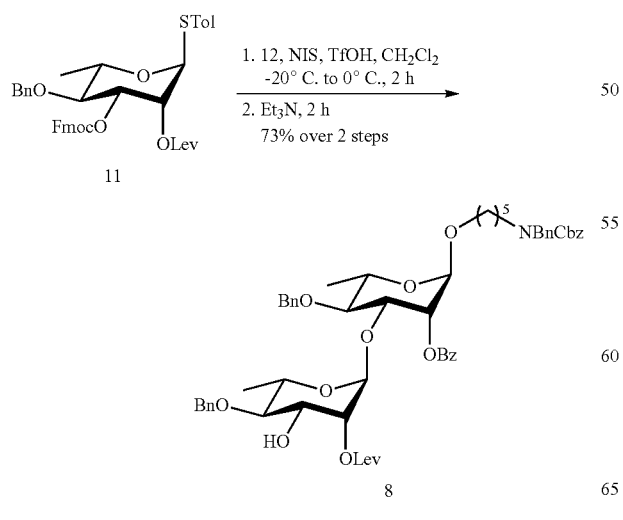

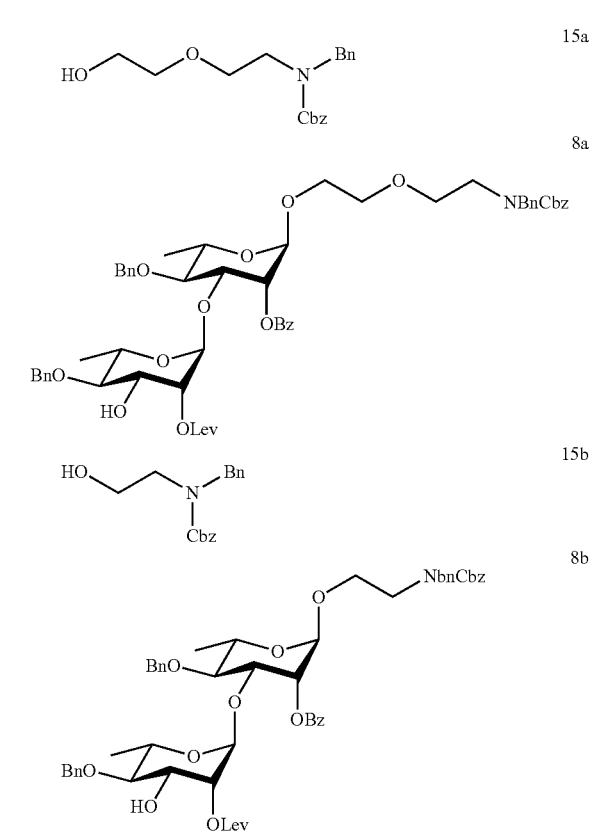

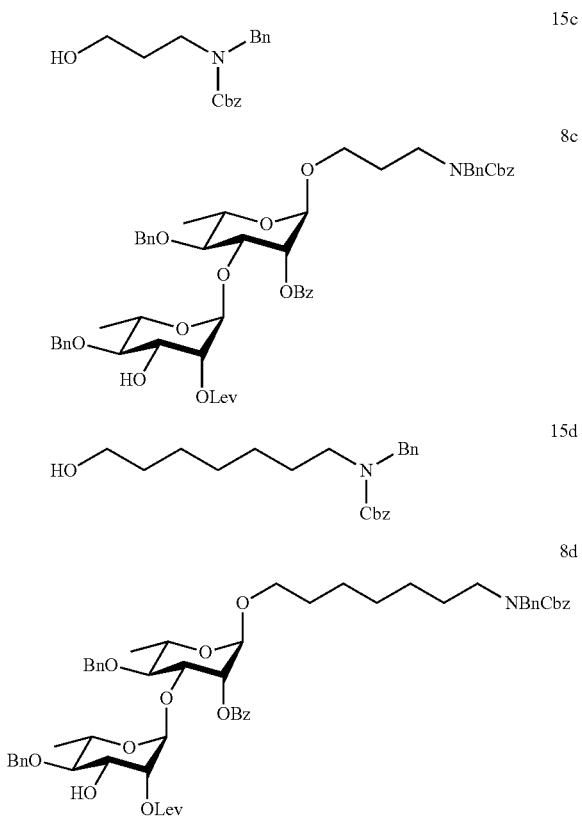

Example A.2: Synthesis of Disaccharide Donor 7

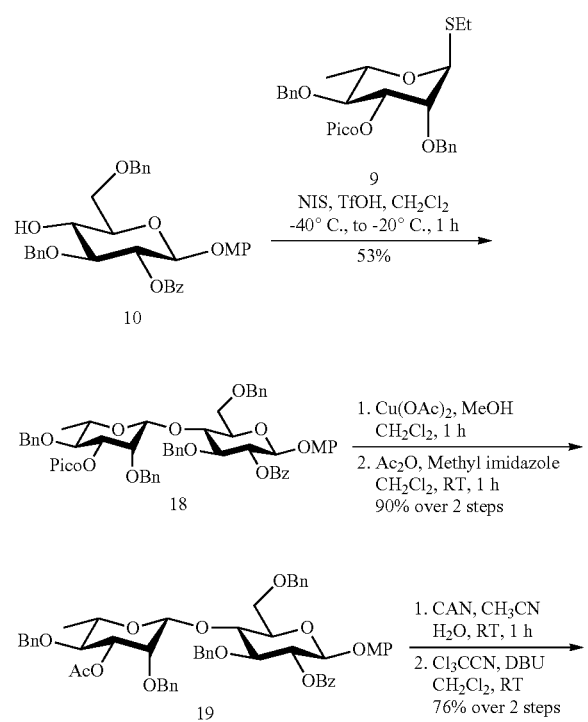

Synthesis of Building Block 9

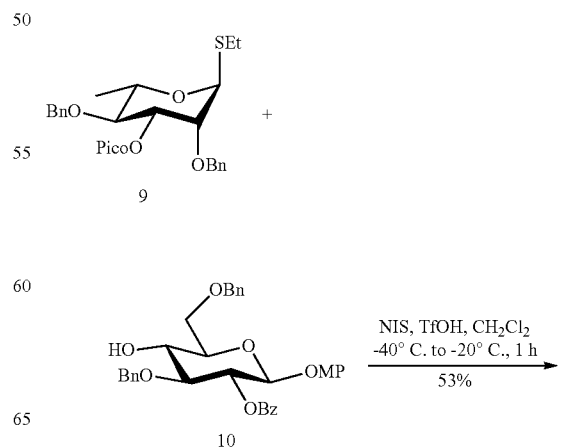

To a stirred solution of compound 17 (Bourke J. *Org. Biomol. Chem.* 2014, 12, 1114) (0.25 g, 0.55 mmol) in $CH_2Cl_2$ (2.5 mL) were added picolinic acid (93 mg, 0.75 mmol), DCC (0.17 g, 0.8 mmol) and DMAP (13.5 mg, 0.11 mmol). After stirring at room temperature for 2.5 h, the reaction mixture was diluted with $CH_2H_2$ (25 mL) and washed successively with cold water (10 mL) and aq. sat. $NaHCO_3$ (10 mL). The organic layer was dried over $Na_2SO_4$ filtered and concentrated. The crude was purified by flash chromatography using hexanes and ethyl acetate as eluent (3:1) to give the desired product 9 as pale yellowish oil (0.307 g, quantitative).

$^1$H NMR (400 MHz, $CDCl_3$) δ 8.80 (ddd, J=4.7, 1.8, 0.9 Hz, 1H), 8.01 (dt, J=7.9, 1.1 Hz, 1H), 7.81 (td, J=7.7, 1.8 Hz, 1H), 7.49 (ddd, J=7.6, 4.7, 1.2 Hz, 1H), 7.32-7.27 (m, 2H), 7.25-7.17 (m, 4H), 7.17-7.09 (m, 4H), 5.43 (dd, J=9.5, 3.4 Hz, 1H), 5.31 (d, J=1.7 Hz, 1H), 4.85 (d, J=11.1 Hz, 1H), 4.74-4.65 (m, 2H), 4.57 (d, J=12.3 Hz, 1H), 4.27-4.14 (m, 1H), 4.11 (dd, J=3.4, 1.7 Hz, 1H), 3.90 (t, J=9.5 Hz, 1H), 2.74-2.51 (m, 2H), 1.38 (d, J=6.2 Hz, 3H), 1.27 (t, J=7.4 Hz, 3H).

Synthesis of Disaccharide 18

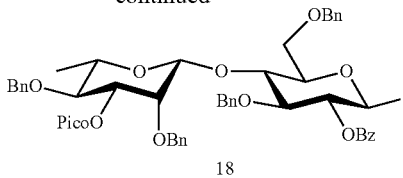

18

NIS (0.15 g, 0.65 mmol) and TfOH (6.0 μL, 0.065 mmol) were added to a cooled solution of donor 9 (0.32 g, 0.64 mmol), acceptor 10 (Bundle D. R. et al. *ACS Chem. Biol.* 2012, 7, 1754) (0.25 g, 0.43 mmol) and 4 Å acid washed molecular sieves (AWMS) (2.0 g) in $CH_2Cl_2$ (20 mL) at −40° C. Reaction mixture was gradually warmed to −20° C. over 1 h, diluted with $CH_2Cl_2$ (30 mL) and washed with aq. sat. $Na_2S_2O_3$ (15 mL). The organic layer was dried over $Na_2SO_4$ filtered and concentrated. The crude was purified by flash chromatography using hexanes and ethyl acetate as eluent (4:1 to 3:1) to obtain the desired product 18 as pale yellowish oil (0.23 g, 53%).

$^1$H NMR (400 MHz, $CDCl_3$) δ 8.88 (d, J=4.7 Hz, 1H), 8.15 (d, J=7.8 Hz, 2H), 8.05 (d, J=8.0 Hz, 1H), 7.87 (t, J=7.9 Hz, 1H), 7.64 (t, J=7.4 Hz, 1H), 7.59-7.44 (m, 3H), 7.42-7.17 (m, 20H), 7.04 (d, J=8.6 Hz, 2H), 6.77 (d, J=8.8 Hz, 2H), 5.59 (t, J=8.3 Hz, 1H), 5.09 (d, J=7.9 Hz, 1H), 5.03 (dd, J=9.8, 3.2 Hz, 1H), 4.88-4.82 (m, 3H), 4.76-4.58 (m, 6H), 4.54 (d, J=10.4 Hz, 1H), 4.27 (d, J=10.4 Hz, 1H), 4.11 (d, J=3.2 Hz, 1H), 4.00-3.79 (m, 4H), 3.77 (s, 3H), 3.39 (dq, J=11.9, 6.2 Hz, 1H), 1.40 (d, J=6.0 Hz, 3H);

$^{13}$C NMR (101 MHz, $CDCl_3$) δ 165.3, 164.0, 155.4, 151.5, 150.2, 147.7, 138.7, 138.4, 138.0, 137.0, 133.4, 129.8 (2C), 128.9, 128.6, 128.4, 128.3 (3C), 128.1, 128.0, 127.8, 127.6, 127.5 (2C), 127.0, 125.2, 118.6, 114.5, 100.8, 100.5, 83.2, 78.6, 75.8, 75.7, 75.3, 74.8, 74.0, 73.5, 71.7, 70.0, 55.6, 17.9; HRMS (ESI): Calcd for $C_{60}H_{59}O_{13}N$ [M+Na]+ 1024.3884, found: 1024.3896.

Synthesis of Disaccharide Building Block 19

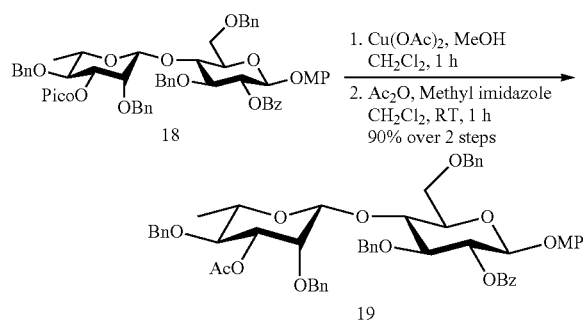

Cu(OAc)$_2$.H$_2$O (70 mg, 0.347 mmol) was added to a solution of 18 (0.23 g, 0.23 mmol) in $CH_2Cl_2$ (6 mL) and MeOH (3 mL). After stirring at room temperature for 1 h, reaction mixture was filtered through celite pad and the filtrate was concentrated. The crude product was dissolved in $CH_2Cl_2$ (5 mL) and to this Ac$_2$O (1 mL), and methyl imidazole (0.2 mL) was added. After 1 h, the reaction mixture was evaporated and purified by flash chromatography using hexanes and ethyl acetate as eluent (6:1 to 5:1) to obtain the desired product 19 as colorless oil (0.193 g, 90%).

$^1$H NMR (400 MHz, $CDCl_3$) δ 8.01 (d, J=7.7 Hz, 2H), 7.51 (t, J=7.4 Hz, 1H), 7.39 (t, J=7.6 Hz, 2H), 7.33-7.01 (m, 20H), 6.89 (d, J=8.9 Hz, 2H), 6.64 (d, J=8.9 Hz, 2H), 5.42 (t, J=8.3 Hz, 1H), 4.93 (d, J=7.9 Hz, 1H), 4.71 (t, J=6.2 Hz, 2H), 4.65-4.43 (m, 7H), 4.39 (d, J=10.5 Hz, 1H), 4.15-4.07 (m, 1H), 3.83-3.67 (m, 4H), 3.65 (s, 3H), 3.63-3.41 (m, 2H), 3.19 (dq, J=12.1, 6.2 Hz, 1H), 1.87 (s, 3H), 1.23 (d, J=6.1 Hz, 3H);

$^{13}$C NMR (101 MHz, $CDCl_3$) δ 170.2, 165.3, 155.4, 151.6, 138.7, 138.6, 138.2, 137.1, 133.4, 129.9, 129.8, 128.8, 128.7, 128.6, 128.5, 128.4, 128.3 (2C), 128.0, 127.9, 127.8, 127.6, 127.5, 118.7, 114.5, 100.8, 100.6, 83.1, 78.7, 77.4, 76.0, 75.79, 75.76, 75.4 (2C), 75.3, 74.9, 74.0, 73.5, 71.8, 70.1, 55.7, 29.8, 21.1, 17.9; HRMS (ESI): Calcd for $C_{56}H_{58}O_{13}$ [M+Na]+961.3775, found: 961.3841.

Synthesis of Imidate Donor 7

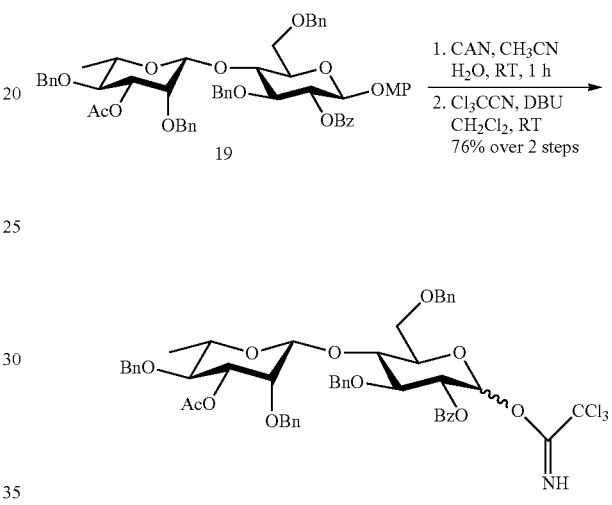

Ceric ammonium nitrate (0.46 g, 0.85 mmol) was added to a solution of 19 (0.16 g, 0.17 mmol) in acetonitrile (5 mL) and H$_2$O (1 mL). After stirring at room temperature for 1 h, Na$_2$SO$_4$ was added to the reaction mixture and filtered through celite pad. The filtrate was concentrated and purified by flash chromatography using hexanes and ethyl acetate as eluent (4:1) to obtain the desired hemiacetal as pale yellowish oil.

The obtained hemiacetal was dissolved in $CH_2Cl_2$ (5 mL) and to this Cl$_3$CCN (0.17 mL, 0.17 mmol), DBU (5.2 μL) were added. After 30 min, hexanes (5 mL) was added to the reaction mixture and purified by flash chromatography using hexanes and ethyl acetate as eluent (5:1) to afford the desired product 7 as colorless oil (0.126 g, 76%, α/β=9:1).

$^1$H NMR (400 MHz, $CDCl_3$) δ 8.47 (s, 1H), 7.95 (d, J=7.8 Hz, 2H), 7.50 (t, J=7.5 Hz, 1H), 7.36 (t, J=7.7 Hz, 2H), 7.32-7.01 (m, 20H), 6.56 (d, J=3.5 Hz, 1H), 5.29 (dd, J=9.9, 3.5 Hz, 1H), 4.76 (s, 1H), 4.70-4.49 (m, 7H), 4.43 (dd, J=23.8, 11.2 Hz, 2H), 4.12 (t, J=9.3 Hz, 1H), 4.05-3.90 (m, 2H), 3.90-3.76 (m, 2H), 3.73 (dd, J=11.2, 4.8 Hz, 1H), 3.51 (t, J=9.5 Hz, 1H), 3.19 (dt, J=12.1, 6.2 Hz, 1H), 1.90 (s, 3H), 1.19 (d, J=4.9 Hz, 3H);

$^{13}$C NMR (101 MHz, $CDCl_3$) δ 170.2, 165.5, 160.6, 138.5 (2C), 138.2, 137.2, 133.6, 129.9, 129.3, 128.8, 128.7, 128.6, 128.5, 128.4, 128.3 (2C), 127.9, 127.8 (2C), 127.6, 127.5, 101.2, 94.1, 91.3, 79.6, 78.7, 76.0, 75.9, 75.9, 75.3, 75.0, 74.8, 73.4, 73.3, 72.9, 71.8, 68.6, 29.8, 21.2, 17.9.

Example A.3: Synthesis of Tetrasaccharide Acceptor 4

Synthesis of Tetrasaccharide 20

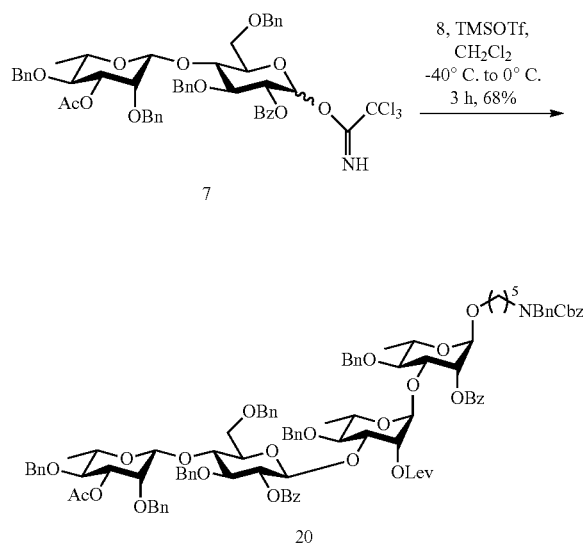

To a solution of donor 7 (60 mg, 0.06 mmol), acceptor 8 (40 mg, 0.04 mmol) and 4 Å acid washed molecular sieves (AWMS) (100 mg) in CH$_2$Cl$_2$ (2 mL) at −40° C. was added TMSOTf (1.5 μL, 8 μmol). The reaction mixture was gradually warmed to 0° C. over 3 h. After complete consumption of donor, a drop of Et$_3$N was added and the solvents were removed under vacuum. The crude was purified by flash chromatography using hexanes and ethyl acetate as eluent (3:1 to 2:1) to afford the desired product 20 as pale yellowish oil (49 mg, 68%).

$^1$H NMR (400 MHz, CDCl$_3$) δ 8.02 (d, J=7.6 Hz, 2H), 7.82 (d, J=7.7 Hz, 2H), 7.54-7.33 (m, 6H), 7.31-7.14 (m, 36H), 6.98-6.90 (m, 2H), 6.79-6.70 (m, 2H), 5.30 (s, 1H), 5.21 (s, 1H), 5.19-5.05 (m, 3H), 4.95 (s, 1H), 4.80 (d, J=10.5 Hz, 1H), 4.76-4.62 (m, 3H), 4.61-4.45 (m, 5H), 4.43-4.37 (m, 4H), 4.35-4.21 (m, 4H), 4.12-4.09 (m, 2H), 3.80-3.69 (m, 2H), 3.67-3.57 (m, 3H), 3.55-3.37 (m, 5H), 3.30-3.03 (m, 7H), 2.63 (t, J=7.0 Hz, 2H), 2.55-2.45 (m, 2H), 2.06 (s, 3H), 1.85 (s, 3H), 1.62-1.31 (m, 6H), 1.19 (s, 3H), 1.10 (d, J=6.1 Hz, 3H), 0.91 (d, J=6.1 Hz, 3H);

$^{13}$C NMR (101 MHz, CDCl$_3$) δ 206.9, 171.7, 170.1, 166.1, 165.0, 139.1, 138.6, 138.5, 138.2, 138.1, 138.0, 136.7, 133.3, 130.1, 129.9, 129.7, 129.6, 128.7, 128.6 (2C), 128.5 (2C), 128.4, 128.3 (2C), 128.2 (2C), 128.0, 127.9 (2C), 127.8, 127.7, 127.3, 127.2, 127.1, 126.7, 101.1, 100.9, 99.29, 97.0, 83.1, 80.4, 80.1, 78.6, 78.0, 77.4, 76.0, 75.8, 75.6, 75.3, 75.2, 74.8, 74.7, 74.1, 74.0, 73.1, 73.0, 72.4, 71.6, 69.3, 68.3, 67.8, 67.5, 67.2, 62.4, 60.5, 50.6, 50.3, 47.2, 46.2, 38.3, 29.8, 29.2, 28.3, 28.0, 27.6, 25.0, 23.4, 22.8, 22.3, 21.2, 21.1, 18.1, 17.7, 17.6; HRMS (ESI): Calcd for C$_{107}$H$_{117}$O$_{25}$N [M+Na]+1839.7846, found: 1839.7621.

Synthesis of Tetrasaccharide Acceptor 4

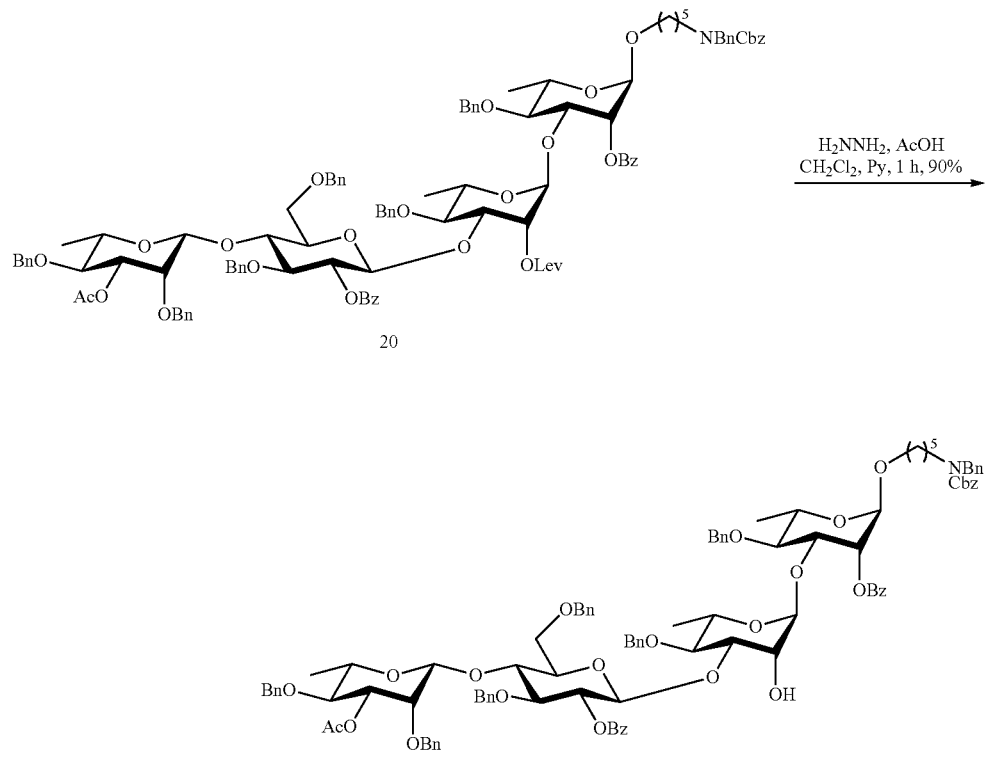

Hydrazine solution [310 μL, a premixed solution of H$_2$NNH$_2$.H$_2$O (50 μL), pyridine (0.6 mL), AcOH (0.4 mL)] was added to a stirred solution of compound 20 (57 mg, 0.03 mmol) in CH$_2$Cl$_2$ (2.0 mL) and pyridine (2 mL) at 0° C. After stirring at 0° C. for 1 h, the reaction mixture was diluted with CH$_2$Cl$_2$ (10 mL) and washed successively with 1 M HCl (5 mL) and aq. sat. NaHCO$_3$ (5 mL). The organic layer was dried over Na$_2$SO$_4$ filtered and concentrated. The crude was purified by flash chromatography using hexanes and ethyl acetate as eluent (3:1 to 2.5:1) to give the desired product 4 as colorless oil (49 mg, 90%).

$^1$H NMR (400 MHz, CDCl$_3$) δ 7.98 (d, J=7.7 Hz, 2H), 7.81 (d, J=7.8 Hz, 2H), 7.52-7.32 (m, 6H), 7.31-7.13 (m, 28H), 7.12-6.94 (m, 10H), 6.77 (d, J=7.3 Hz, 2H), 5.24 (dd, J=14.9, 6.1 Hz, 2H), 5.09 (d, J=9.9 Hz, 2H), 4.90 (s, 1H), 4.81-4.67 (m, 3H), 4.65-4.38 (m, 10H), 4.36-4.21 (m, 3H), 4.20-3.96 (m, 4H), 3.85-3.63 (m, 5H), 3.60-3.39 (m, 6H), 3.35-3.07 (m, 7H), 1.86 (s, 3H), 1.56-1.38 (m, 6H), 1.23 (d, J=6.2 Hz, 3H), 1.19 (d, J=6.2 Hz, 3H), 0.85 (d, J=6.4 Hz, 3H);

$^{13}$C NMR (101 MHz, CDCl$_3$) δ 170.2, 165.9, 165.2, 138.6, 138.5, 138.4, 138.3, 138.1, 138.0, 136.9, 133.3, 133.2, 130.2, 129.9, 129.8, 129.5, 128.8, 128.7, 128.6, 128.5 (3C), 128.4 (3C), 128.3, 128.1, 127.9 (3C), 127.8 (2C), 127.6, 127.4, 127.2, 127.1, 101.2, 100.9, 100.5, 97.1, 83.0, 82.1, 80.2, 79.2, 78.6, 78.3, 77.4, 76.0, 75.7, 75.6, 75.5, 75.3, 74.8, 74.4, 74.3, 73.6, 73.5, 72.9, 71.7, 70.1, 69.5, 68.1, 68.0, 67.6, 67.3, 50.7, 50.3, 47.2, 46.3, 21.1, 18.2, 17.9, 17.7; HRMS (ESI): Calcd for C$_{102}$H$_{111}$O$_{23}$N [M+Na]+1741.7478, found: 1741.7240.

Example A.4: Synthesis of Disaccharide Donor 3

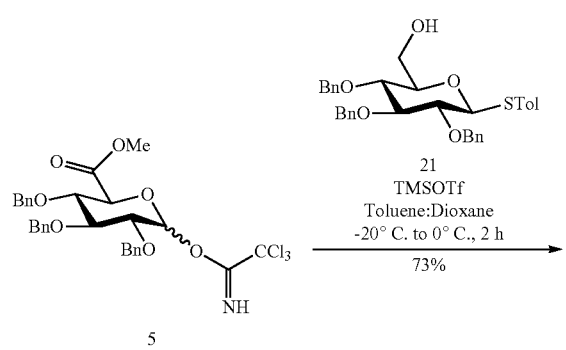

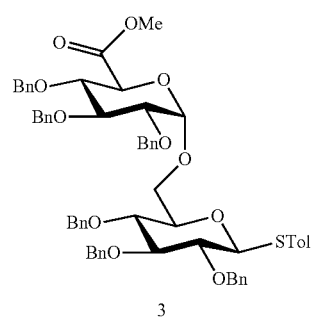

Synthesis of Glucuronic Acid Building Block 22

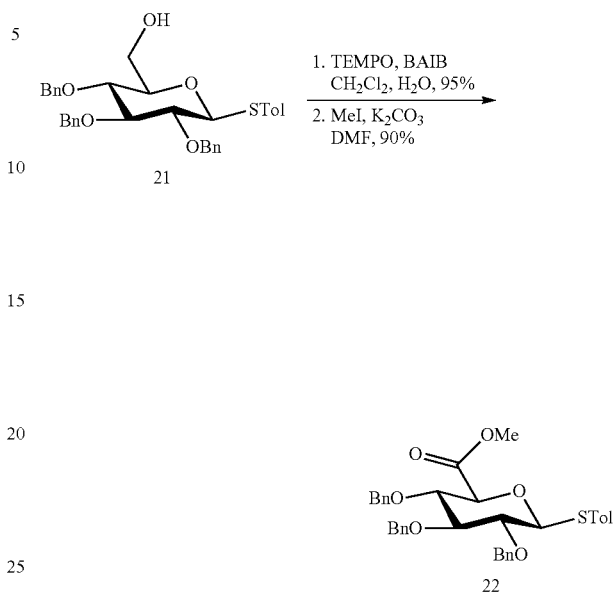

BAIB (4.34 g, 13.47 mmol) and TEMPO (0.17 g, 1.08 mmol) were added to a solution of 21 (Z. Guan et al. *J. Org. Chem.* 2012, 77, 8888) (3 g, 5.39 mmol) in CH$_2$Cl$_2$ (15 mL) and H$_2$O (7.5 mL). The reaction mixture was stirred at room temperature for 2 h and quenched using aq. sat. Na$_2$S$_2$O$_3$ solution (150 mL). The aqueous phase was extracted with EtOAc (3×100 mL) and dried over Na$_2$SO$_4$. After concentration, the residue was purified by flash chromatography using cyclohexane and ethyl acetate as eluent (7:1 and 0.5% formic acid in eluent) to afford the acid as a white solid (2.92 g, 95%).

To a stirred solution of the acid (2.92 g, 5.12 mmol) in DMF (25 mL) was added MeI (1.45 g, 10.23 mmol) and K$_2$CO$_3$ (1.7 g, 12.3 mmol). The solution was stirred at room temperature for 10 h and quenched by the addition of MeOH (20 mL). The reaction mixture was diluted with EtOAc (80 mL) and washed with H$_2$O (50 mL). The organic layer was dried over Na$_2$SO$_4$ and concentrated. The crude was purified by flash chromatography using hexanes and ethyl acetate as eluent (9:1 to 6:1) to give the desired product 22 as a white solid (2.7 g, 90%).

$^1$H NMR (400 MHz, CDCl$_3$) δ 7.49-7.42 (m, 2H), 7.40-7.27 (m, 13H), 7.22 (m, 2H), 7.15-7.09 (m, 2H), 4.91-4.67 (m, 5H), 4.61 (m, 2H), 3.90 (m, 1H), 3.81 (t, J=9.3 Hz, 1H), 3.73 (s, 3H), 3.70 (t, J=8.8 Hz, 1H), 3.49 (dd, J=9.7, 8.7 Hz, 1H), 2.34 (s, 3H);

$^{13}$C NMR (101 MHz, CDCl$_3$) δ 168.9, 138.2 (2C), 138.0, 137.8, 133.0, 129.9, 129.4, 128.6, 128.5 (3C), 128.3, 128.1, 128.0 (2C), 127.9 (2C), 127.7, 88.7, 86.0, 80.4, 79.4, 78.1, 76.0, 75.6, 75.2, 52.6, 21.3; HRMS (ESI): Calcd for C$_{35}$H$_{36}$O$_6$S [M+Na]+607.2130, found: 607.2140.

Synthesis of Imidate Donor 5

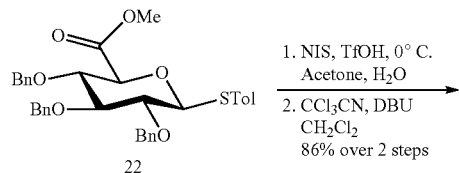

Synthesis of Disaccharide 3

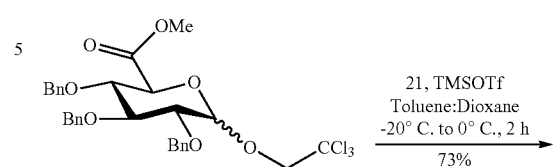

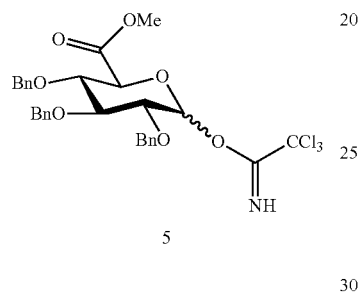

NIS (92 mg, 0.41 mmol) and TfOH (3 µL, 0.34 mmol) were added at 0° C. to a solution of 22 (0.2 g, 0.34 mmol) in acetone (2 mL) and water (1 mL). After stirring at 0° C. for 4 h, the reaction mixture was quenched with Et$_3$N (0.5 mL). Diluted the reaction mixture with CH$_2$Cl$_2$ (15 mL). and washed with aq. sat. Na$_2$S$_2$O$_3$ (5 mL). Separated organic layer was dried over Na$_2$SO$_4$ filtered and concentrated. The crude was purified by flash chromatography using hexanes and ethyl acetate as eluent (4:1 to 3:1) to give the hemiacetal as pale yellowish liquid (0.164 g).

DBU (5 µL, 0.034 mmol) and Cl$_3$CCN (0.34 mL, 3.42 mmol) were added to a cooled solution of hemiacetal (0.164 g, 0.342 mmol) in CH$_2$Cl$_2$ (2 mL) 0° C. After stirring at 0° C. for 1 h, the reaction mixture was evaporated on rotor and the crude was purified by flash chromatography using hexanes and ethyl acetate as eluent (5:1 to 4:1) to obtain the product 5 as colorless oil (0.183 g, 86%, α/β=2.7/1).

$^1$H NMR (400 MHz, CDCl$_3$) δ 8.60 (s, 1H), 7.33-7.08 (m, 15H), 6.45 (d, J=3.5 Hz, 1H), 5.00-4.50 (m, 5H), 4.36 (d, J=10.1 Hz, 1H), 4.11-3.95 (m, 1H), 3.82-3.66 (m, 3H), 3.65 (s, 3H);

$^{13}$C NMR (101 MHz, CDCl$_3$) δ 169.3, 161.1, 138.4, 138.0, 137.8, 137.7, 129.2, 128.6, 128.5 (3C), 128.4, 128.3, 128.2, 128.1, 128.0 (2C), 127.9, 127.8 (2C), 125.4, 94.0, 91.1, 83.7, 80.8, 78.9, 78.8, 75.9, 75.7, 75.5, 75.2, 73.2, 72.6, 52.7; HRMS (ESI): Calcd for C$_{30}$H$_{30}$O$_7$NCl$_3$ [M+Na]$^+$ 644.0986, found: 644.1014.

TMSOTf (4 µL, 0.02 µmol) was added to a solution of donor 5 (0.14 g, 0.22 mmol), and acceptor 21 (90 mg, 0.16 mmol) in a mixture of solvents toluene (2 mL) and dioxane (6 mL) at −20° C. The reaction mixture was gradually warmed to 0° C. over 2 h. A drop of Et$_3$N was added and the solvents were removed under vacuum. The crude was purified by flash chromatography using hexanes and ethyl acetate as eluent (7:1 to 5:1) to afford the desired product 3 as pale yellowish oil (0.12 g, 73%, α/β=3.5:1).

$^1$H NMR (400 MHz, CDCl$_3$, α-anomer) δ 7.43 (d, J=7.8 Hz, 2H), 7.40-7.18 (m, 30H), 7.06 (d, J=7.8 Hz, 2H), 5.08 (d, J=3.5 Hz, 1H), 4.94 (d, J=10.9 Hz, 1H), 4.88-4.60 (m, 9H), 4.58-4.47 (m, 3H), 4.29 (d, J=10.0 Hz, 1H), 3.95 (t, J=9.3 Hz, 1H), 3.86 (dd, J=12.1, 4.3 Hz, 1H), 3.82-3.69 (m, 3H), 3.67 (d, J=4.9 Hz, 3H), 3.64-3.54 (m, 2H), 3.39 (dd, J=9.7, 3.9 Hz, 1H), 3.17 (t, J=9.3 Hz, 1H), 2.21 (s, 3H);

$^{13}$C NMR (101 MHz, CDCl$_3$) δ 170.4, 138.6, 138.3, 138.2, 138.1 (2C), 138.0, 133.2, 129.9, 128.6 (2C), 128.5 (3C), 128.4 (3C), 128.3, 128.1 (2C), 128.0, 127.9, 127.8, 127.7, 127.6 (2C), 98.0, 88.6, 86.7, 81.1, 81.0, 79.8, 79.6, 78.9, 77.3, 75.9, 75.7, 75.6, 75.2, 75.1, 72.6, 70.4, 66.5, 52.5, 21.2; HRMS (ESI): Calcd for C$_{62}$H$_{64}$O$_{11}$S [M+Na]+ 1039.4067, found: 1039.4091.

Example A.5: Synthesis of Hexasaccharide 2
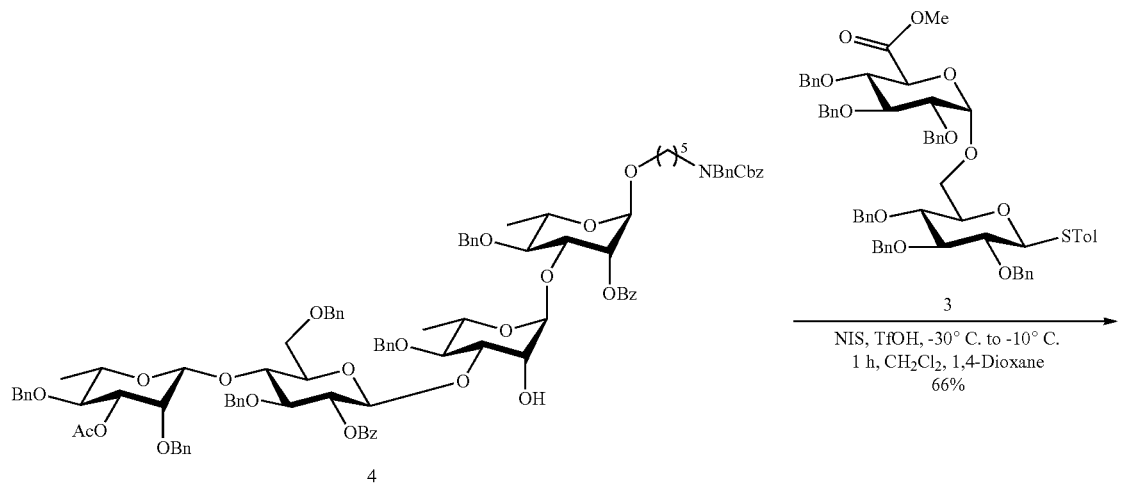
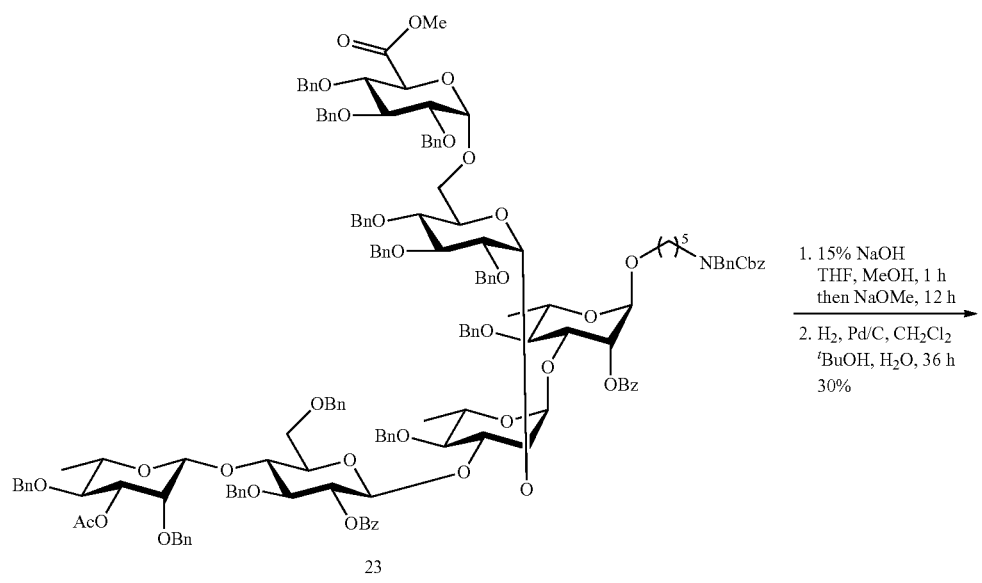

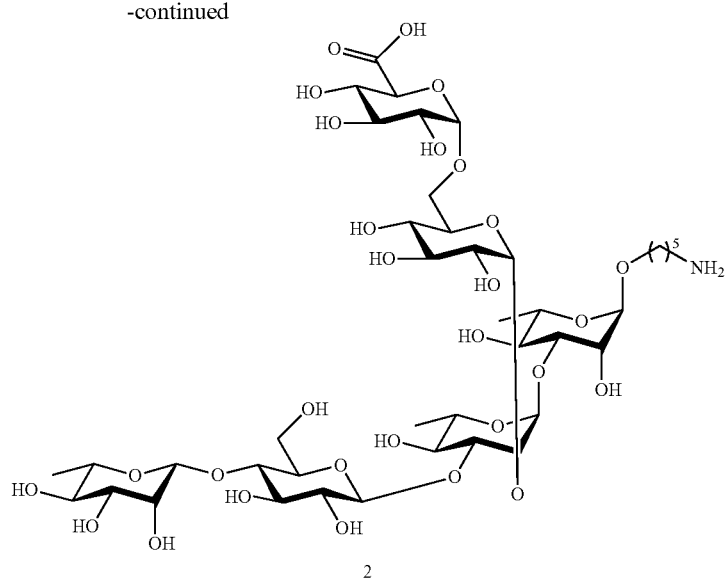

2

Synthesis of Hexasaccharide 23

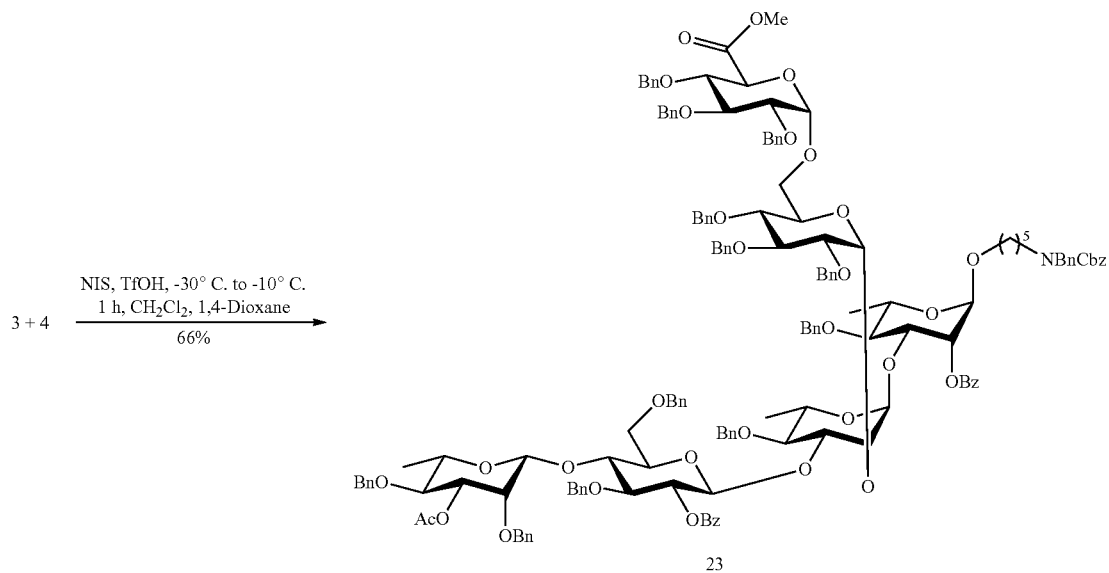

NIS (12 mg, 0.05 mmol) and TfOH (1 μL) were added at −30° C. to a cooled solution of donor 3 (52 mg, 0.05 mmol), acceptor 4 (45 mg, 0.026 mmol) and 4 Å acid washed molecular sieves (AWMS) (0.2 g) in mixture of $CH_2Cl_2$ (1 mL) and dioxane (1 mL).

Reaction mixture was gradually warmed to −10° C. over 1 h, diluted with $CH_2Cl_2$ (10 mL) and washed with aq. sat. $Na_2S_2O_3$ (5 mL). Separated organic layer was dried over $Na_2SO_4$, filtered and concentrated. The crude was purified by flash chromatography using hexanes and ethyl acetate as eluent (4:1 to 3:1) to obtain the desired product 23 as colorless oil (45 mg, 66%).

$^1$H NMR (400 MHz, $CDCl_3$) δ 8.05 (d, J=7.7 Hz, 2H), 7.78 (d, J=7.8 Hz, 2H), 7.50-7.32 (m, 8H), 7.30-7.01 (m, 63H), 6.98-6.89 (m, 3H), 6.86-6.83 (m, 2H), 5.25 (s, 1H), 5.19-5.12 (m, 2H), 5.07 (d, J=4.5 Hz, 2H), 4.90-4.45 (m, 20H), 4.42-4.08 (m, 12H), 4.06-3.52 (m, 16H), 3.50 (d, J=4.1 Hz, 3H), 3.48-2.95 (m, 13H), 1.87 (s, 3H), 1.58-1.36 (m, 6H), 1.14 (d, J=6.2 Hz, 3H), 1.07 (d, J=6.1 Hz, 3H), 0.88 (d, J=6.2 Hz, 3H);

$^{13}$C NMR (101 MHz, $CDCl_3$) δ 170.6, 170.2, 166.2, 164.6, 139.4, 139.3, 138.9 (2C), 138.8, 138.7, 138.5, 138.3, 138.2, 137.0, 133.3, 133.0, 130.2, 130.0, 129.9, 128.8, 128.6 (2C), 128.5 (3C), 128.4 (3C), 128.3, 128.2 (3C), 128.1, 128.0, 127.9 (3C), 127.8, 127.7, 127.6, 127.5, 127.4, 127.3, 127.2, 127.1, 126.6, 101.4, 100.7, 99.3, 98.1, 97.0, 95.9, 83.2, 81.7, 81.0, 80.7, 80.4, 80.2, 79.8, 79.6, 78.7, 77.5, 77.4, 77.3, 77.2, 76.8, 76.1, 75.7, 75.2, 75.1, 75.0, 74.7, 73.8, 73.7, 73.3, 73.1, 72.7, 71.8, 71.5, 71.3, 70.4, 67.6, 67.3, 66.9, 58.6, 53.6, 52.3, 31.1, 29.8, 21.1, 18.6, 18.1, 17.8, 17.6; HRMS (ESI): Calcd for $C_{157}H_{167}O_{34}N$ [M+Na]$^+$ 2634.1301, found: 2634.0912.

Synthesis of 5-amino pentyl β-L-rhamnopyranosyl-(1→4)-β-D-glucopyranosyl-(1→3)-α-L-{α-D-glucopyranosyl uronate-(1→6)-α-D-glucopyranosyl-(1→2)}rhamnopyranosyl-(1→3)-α-L-rhamnopyranoside (2)

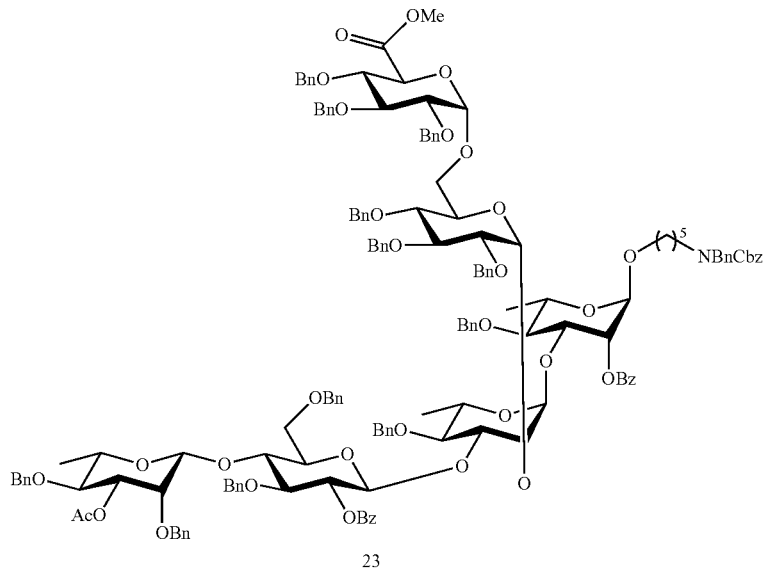

23

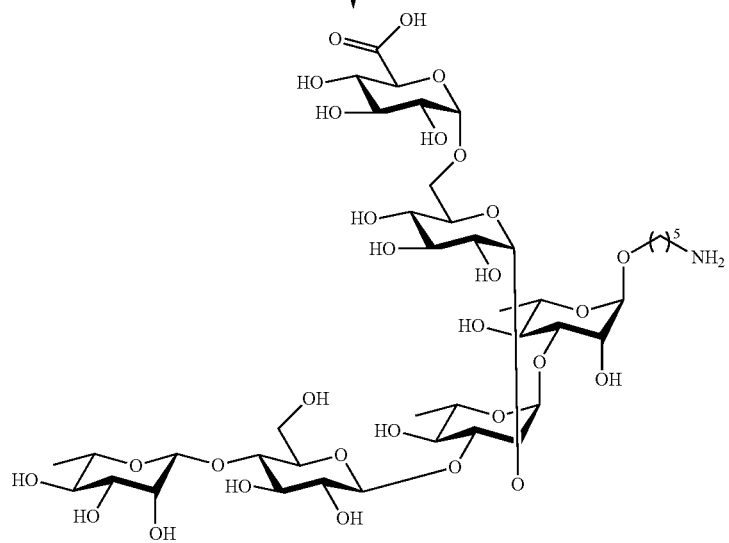

2

To a stirred solution of hexasaccharide 23 (6 mg, 2.3 μmol) in THF (0.5 mL) and MeOH (0.5 mL), was added aq. NaOH (15%, 100 μL). After stirring at room temperature for 1 h, NaOMe (6 mg) was added and allowed to stir for 12 h. After complete consumption of starting material, the reaction mixture was neutralized with Amberlite 120 H+resin, filtered, and concentrated. The crude material was purified by flash column chromatography using hexanes and ethyl acetate as eluent (1:1 to 1:2) to afford the desired deacylated product as white solid. The obtained deacylated product was dissolved in $CH_2Cl_2$ (0.5 mL), $^tBuOH$ (1 mL) and water (0.5 mL). To this solution a suspension of Pd/C (50 mg) in a mixture of $^tBuOH$ (1 mL) and water (0.5 mL) was added and stirred under hydrogen atmosphere for 36 h. Reaction mixture was then filtered, concentrated and purified by C18 column to afford the desired product 2 (0.7 mg, 30%) as a white solid.

$^1$H NMR (400 MHz, D$_2$O) δ 5.07 (s, 1H), 5.02-4.94 (m, 2H), 4.91 (d, J=3.7 Hz, 1H), 4.73 (d, J=1.5 Hz, 1H), 4.63 (d, J=7.9 Hz, 1H), 4.35-4.18 (m, 3H), 4.05 (m, 4H), 3.96-3.81 (m, 3H), 3.80-3.61 (m, 8H), 3.61-3.40 (m, 8H), 3.38-3.25 (m, 3H), 3.24-3.13 (m, 1H), 2.96 (t, J=7.6 Hz, 2H), 1.66 (dt, J=15.9, 8.0 Hz, 4H), 1.43 (p, J=7.8, 7.3 Hz, 2H), 1.33-1.19 (m, 9H);
HRMS (ESI): Calcd for C$_{41}$H$_{71}$O$_{29}$N [M+Na]$^+$ 1064.4009, found: 1064.4067.
Applying the synthetic procedures of example A.5 to disaccharides 15a, 15b, 15c and 15d provides hexasaccharides 2a, 2b, 2c and 2d, respectively.
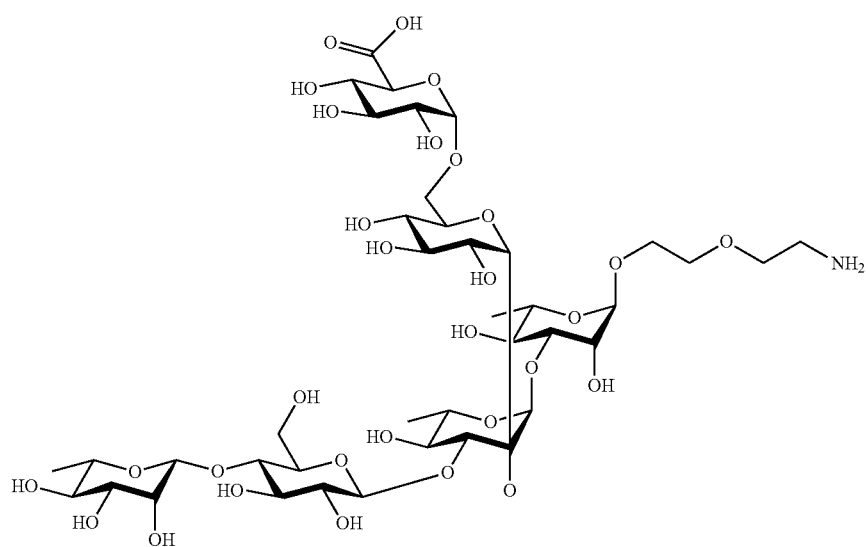
2a
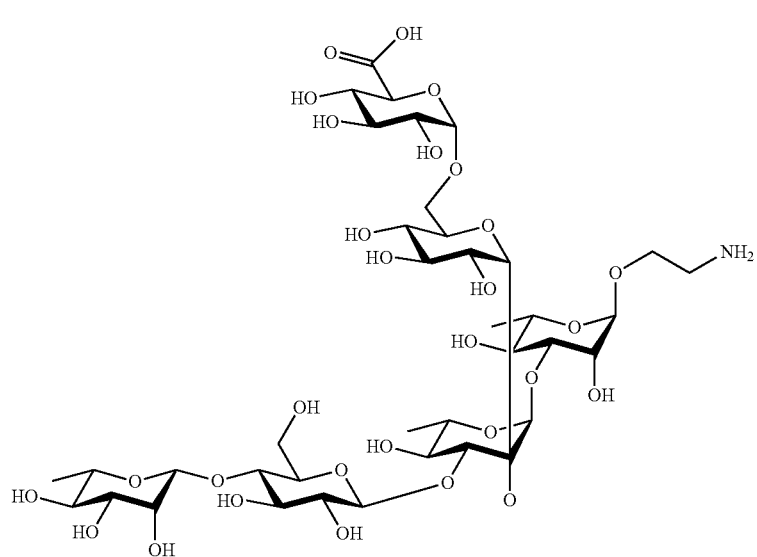
2b

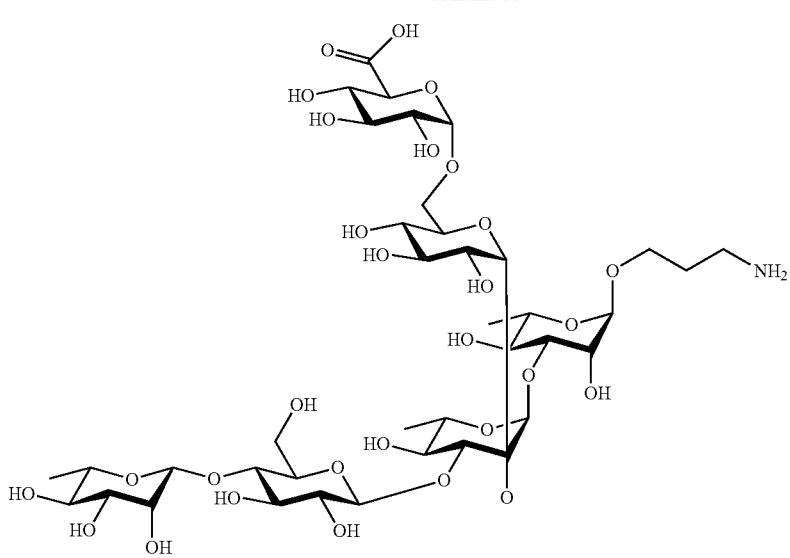

2c

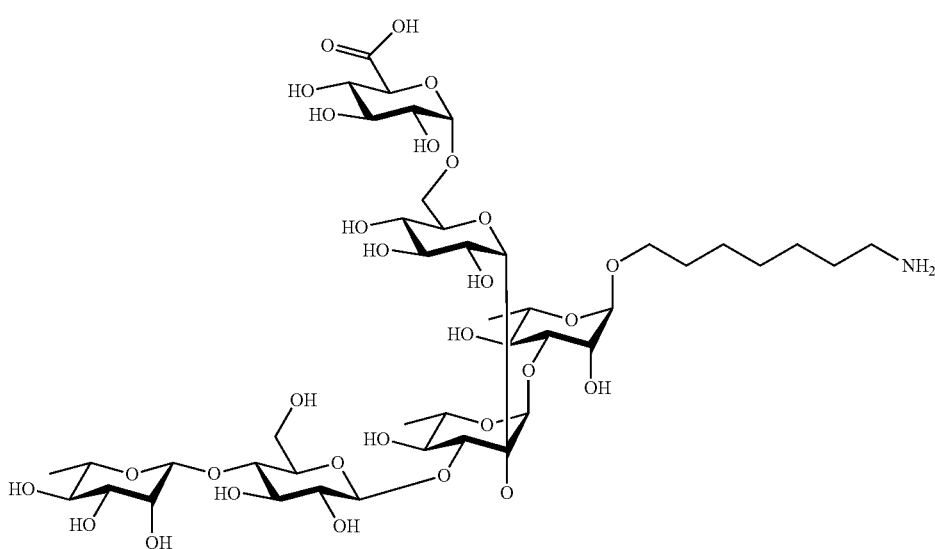

2d

Example A.6: Synthesis and Characterization of Conjugates

General Procedure Synthesis

Formation of the p-Nitro Phenyl (PNP) Amide

To the saccharide of general formula (I) (1 equivalent) and diphenyl adipate (7 equivalents) in a glass vial were added a mixture of pyridine and DMSO (1:1) and the mixture let stir for 5 minutes for complete solubilization. Then, triethylamine (0.83 µL, 6 µmol, 10 equivalents) was added and let stir for 20 minutes. TLC indicated complete consumption of the starting material. The solvent was removed in vacuum. The residue was washed with dichloromethane (3×1 mL) to remove PNP ester excess and the white solid obtained was dried in vacuum.

Conjugation of PNP Ester Derivatized Saccharide to $CRM_{197}$ 40 equivalents of lyophilized $CRM_{197}$ was dissolved in 0.4 mL of sterile 0.1 M sodium phosphate, pH 8.0 and transfer into upper chamber of 10,000 Da Millipore centrifugal filter (0.5 mL). Rinse glass vial with 3×0.4 mL of sterile 0.1 M sodium phosphate, pH 8.0, transfer to the same centrifugal filter. Centrifuge at 10,000 rpm for 6-8 min. If needed, prolong final centrifugation step such that volume in upper chamber is 80-100 µL. The $CRM_{197}$ solution was then transfer into 1.5 mL tube containing lyophilized PNP ester derivatized saccharide and shake slowly (around 180-200 rpm) for 18-24 hrs at room temperature. The conjugate was washed once with 0.1M Sodium phosphate, pH 8.0 and 2-3 times with deionized, autoclaved water using 10,000 Da Millipore centrifugal filters. Take out small sample for MALDI analysis and transfer the conjugate into PBS. If needed, prolong final centrifugation step such that volume in upper chamber is about 250 µL. Transfer content of upper chamber to new 1.5 mL Eppendorf tube, store at 4° C.

Characterization of Glycoconjugates

A. MALDI analysis: The average molecular size of conjugates were determined by Matrix-assisted laser desorption/ionization (MALDI) analysis using $CRM_{197}$ as standard and calculate the average oligosaccharides attachments with per $CRM_{197}$ molecule.

B. SDS-PAGE: The conjugates were resolved by SDS-PAGE (10%) in denaturing condition. The samples were prepared in 6×SDS-PAGE sample loading dye. The electrophoresis was carried out at 120 V and 25 mA for 1 hr 30 min in electrode buffer and gel was stained with Coomassie brilliant blue R250.

Protein Estimation

The protein concentration was estimated using Micro BCA Protein Assay Kit (Thermo-scientific, USA) following the manufacturer's instructions. The sample was prepared in PBS and mixed with equal volume of reagent mixture (B:C:A:24:1:25). The plate was incubated at 37° C. and the absorbance was measured at 560 nm. The standard curve was plotted with known concentration of BSA provided with the kit.

Synthesis of Conjugate $CRM_{197}$-Hexasaccharide 2

Figure 4:
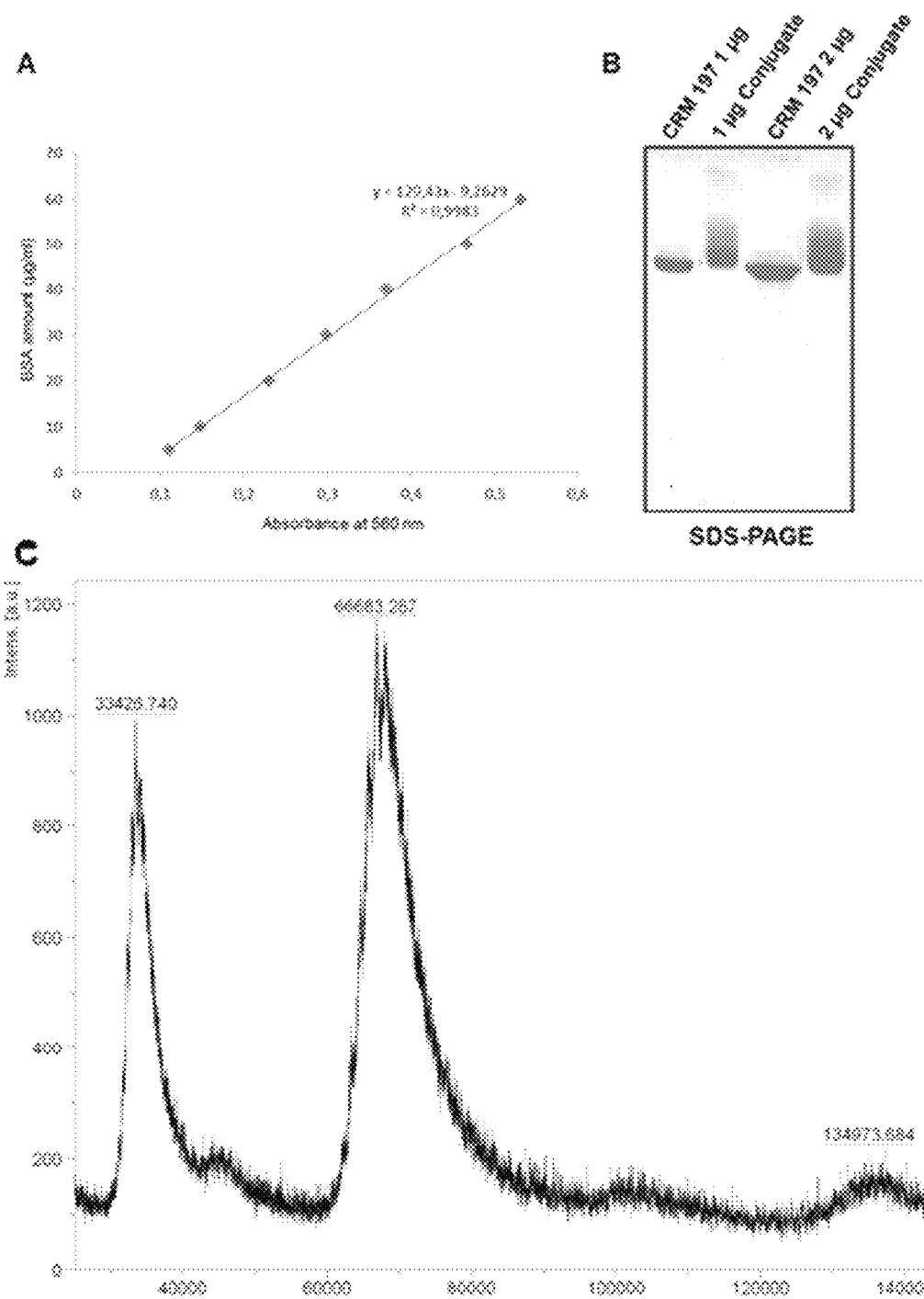
FIG. 4: Characterization of conjugate CRM$_{197}$-hexasaccharide 2. (A) The protein amount was estimated using the standard curve plotted with known concentration of BSA. (B) The conjugate CRM$_{197}$-hexasaccharide 2 was resolved on 10% SDS-PAGE along with CRM$_{197}$ and stained with Coomassie brilliant blue R250. (C) Matrix-assisted laser desorption/ionization (MALDI) analysis was carried out to measure the average molecular size of the conjugate. CRM$_{197}$ was used as standard.
Figure 5:
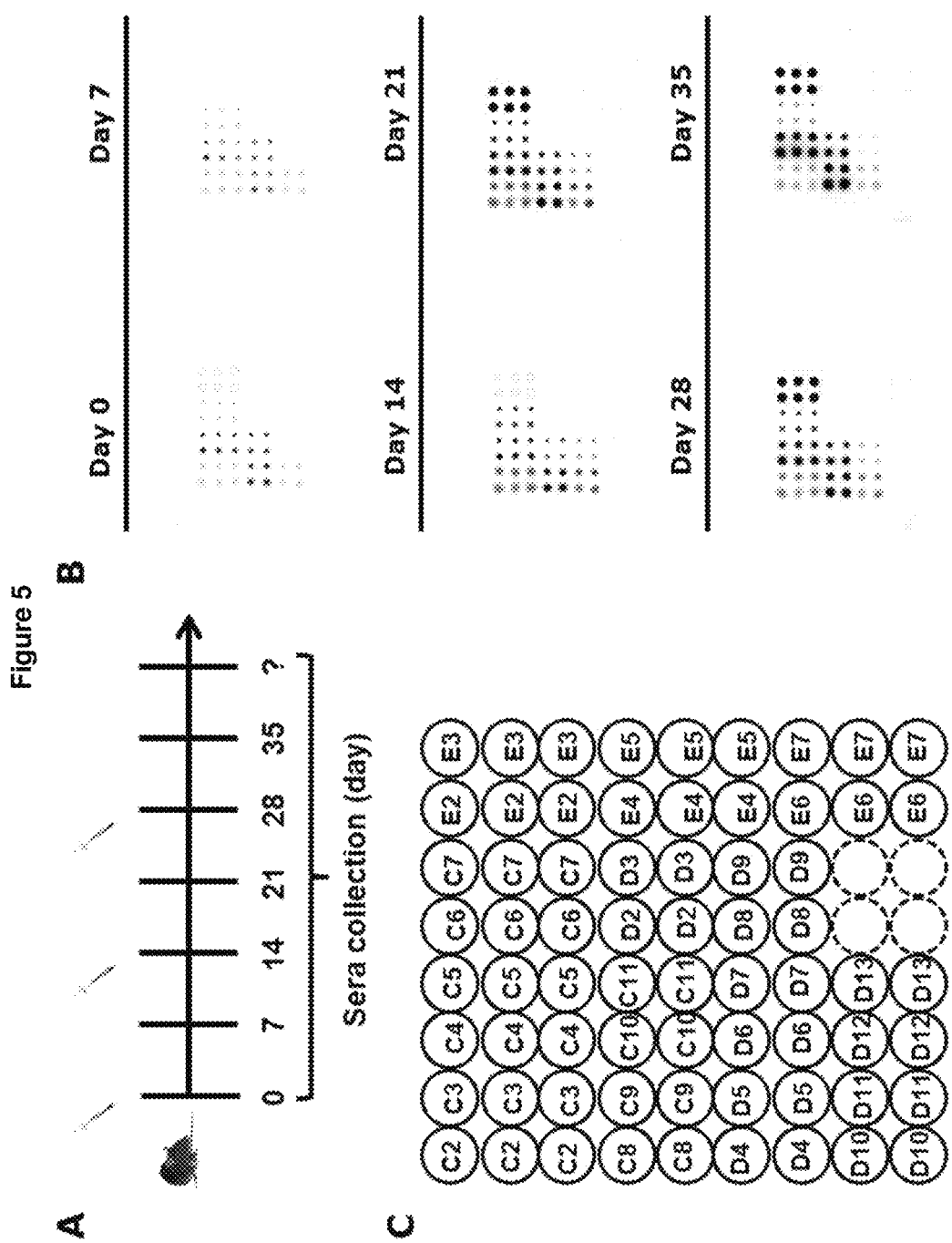
FIG. 5: Glycan microarray analysis. The hyperimmune sera raised in mice immunized with conjugate CRM$_{197}$-hexasaccharide 2 with alum adjuvant was subjected to microarray analysis. (A) Immunization pattern. (B) The representative microarray scanning with pooled sera (pre-immune and every week after first immunization) from mice (n=3) immunized and boosted with conjugate CRM$_{197}$-hexasaccharide 2. Fluorescence excited at 635 nm of the microarray slide incubated with pooled mouse sera (1 in 100 dilution in 1% BSA-PBS) and subsequently with anti-mouse IgG Alexa Fluor 635 (1 in 400 dilution in 1% BSA-PBS). (C) Printing pattern of microarray slides printed with synthetic oligosaccharides and polysaccharides. The printed slide also contains type 19F polysaccharide, cell wall polysaccharide (CWPS) and printing buffer. (D) Oligosaccharide name and position as printed on slides.

Following the above-described procedure, conjugate $CRM_{197}$-hexasaccharide 2 was synthesized. The conjugate was estimated using known amount of BSA as slandered and confirmed by 10% SDS-PAGE, showing a shift toward a higher mass of the glycoconjugates compared with unconjugated $CRM_{197}$ (FIGS. 4A and B). MALDI-TOF mass spectrometry analysis was used to determine the oligosaccharide-to-$CRM_{197}$ molar ratio (FIG. 4C). Mass analysis of the conjugate $CRM_{197}$-hexasaccharide 2 revealed that an average of 7-8 molecules of hexasaccharide 2 was loaded onto one molecule of $CRM_{197}$.

B. Biological Evaluation

Example B.1: Mice Immunization and Generation of Polyclonal Sera

Material and Methods

Mice: Six to eight week old female C57BL/6J inbred strains of mice were obtained from the Charles River, Sulzfeld (Germany). Animals were rested and handled in accordance with the Institutional Animal Ethics guidelines.

Mice Immunization and Generation of Polyclonal Sera

In brief, groups of 3 C57BL/6J female 6-8 week old inbred mice were immunized subcutaneously with conjugate $CRM_{197}$-hexasaccharide 2 (3 µg sugar per dose) emulsified with 1:1 (v/v) alum (aluminium hydroxide) adjuvants. On day 14 and 28 mice were received a booster injection with the same amount of antigen emulsified with 1:1 (v/v) alum. A group of mice were also immunized with conjugate $CRM_{197}$-hexasaccharide 2 (3 µg sugar per dose) only to check the immunogenicity. Mice were bled submandibular weekly using sterile single-use blood lancet. Control mice received only PBS and PBS in alum. The antibody responses were measured in both sera by glycan microarray and ELISA.

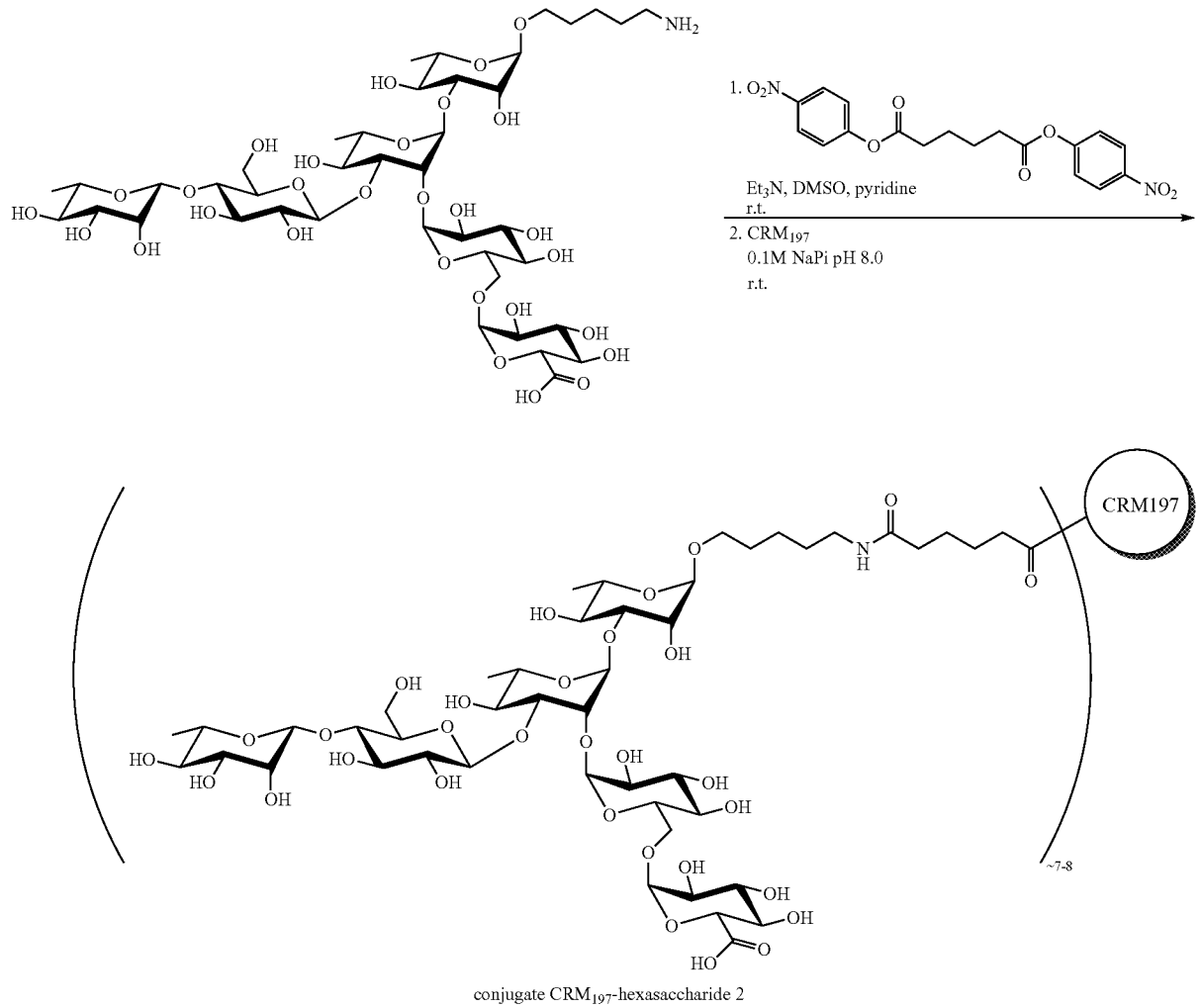

conjugate $CRM_{197}$-hexasaccharide 2

Preparation of microarrays slides: The CodeLink NHS activated glass slides (Surmodics) were spotted with synthetic glycans and native polysaccharides at two different concentration (100 µM and 200 µM) in printing buffer (50 mM sodium phosphate, pH 8.5) by using a S3 piezoelectric microarray printer (Scienion) equipped with a type 4 coated nozzle. The relative humidity of spotted chamber was constantly maintained at 65%. The spotted slides were incubated over night at room temperature in a humidifying chamber. The unreactive groups on the slides were blocked with 50 mM sodium phosphate, 100 mM ethanolamine pH 9.0 at room temperature for one hour. Slides were subsequently washed three times for 5 min with water, dried by centrifugation at 300 g for 5 min (CombiSlide system, Eppendorf) and stored at 4° C. until use.

Microarray binding assays: The printed slides were blocked with PBS-BSA (1%) for 1 h at room temperature and washed 3 times with PBS. The slides were dried by centrifugation at 1200 rpm for 5 min before use. A FlexWell 64 (Grace Bio-Labs, Bend, Oreg., USA) grid was applied to microarray slides. Slides were incubated with polyclonal sera raised in mice against conjugate $CRM_{197}$-hexasaccharide 2 at multiple dilutions, diluted in 1% BSA in PBS (w/v) and incubated in a humid chamber for 1 h at room temperature. Slides were washed three times with PBST (0.1% Tween-20 in PBS) and dried by centrifugation (300×g, 5 min). Slides were incubated with a fluorescence-labeled goat anti-mouse secondary antibodies (Life Technologies) diluted in 1% BSA in PBS (w/v) in a humid chamber for 1 h at room temperature, washed three times with PBST, rinsed once with deionized water and dried by centrifugation (300×g, 5 min) prior to scanning with a GenePix 4300A microarray scanner (Molecular Devices, Sunnyvale, Calif., USA). Image analysis was carried out with the GenePix Pro 7 software (Molecular Devices). The photomultiplier tube (PMT) voltage was adjusted such that scans were free of saturation signals.

Results:

To analyze the antibody response against conjugate $CRM_{197}$-hexasaccharide 2, hyperimmune sera raised in mice immunized with conjugate $CRM_{197}$-hexasaccharide 2 was subjected at different dilution to microarray slides printed with synthetic oligosaccharides and polysaccharides. The microarray data confirmed that the conjugate $CRM_{197}$-hexasaccharide 2 is immunogenic in mice and exhibits robust antibody response as shown by the analysis performed every week before and after immunization (FIG. 4B). Interestingly, hexasaccharide 2 specific serum antibody level increased gradually after the immunization, observed robust induction after boosting and exhibited the reactivity with native polysaccharides. Hexasaccharide 2 specific antibodies were also cross-reactive with other fragments of hexasaccharide 2 printed on the slides (FIG. 4B). Hence, the microarray analyses attest that hexasaccharide 2 is immunogenic in mice and induces cross-reactive antibodies.

Example B.2: Evaluation of Cross-Reactivity of Antibodies

ELISA: The cross-reactivity of antibodies raised in mice immunized with conjugate $CRM_{197}$-hexasaccharide 2 was analyzed with capsular polysaccharide (CPS) of S. pneumoniae serotype 2 by ELISA. Ninety six well polystyrene microtiter plate (Corning, N.Y.) was coated overnight at 4° C. with CPS (50 µl of 10 µg/ml per well) in phosphate buffer saline, pH 7.4. The plates were washed thrice with PBS containing 0.1% Tween-20 (PBST) and blocked with PBS containing 2% BSA at room temperature for 1 hr. After washing thrice with PBST, the plate was incubated with pooled sera in two fold dilutions starting from 1 in 500 dilutions room temperature for 1 hr. The plate was washed 4 to 5 times with PBST and further incubated with horseradish peroxidase (HRP) conjugated goat anti-mouse Ig antibody (diluted 1 in 10000 in PBS containing 0.5% BSA) followed by incubation at room temperature for 1 hr. The plate was washed thoroughly with PBST and developed using 1-Step Ultra TMB (ThermoFisher Sci. USA). The reaction was stopped by adding 2% $H_2SO_4$ and absorbance was recorded at 450 nm.

Figure 6:
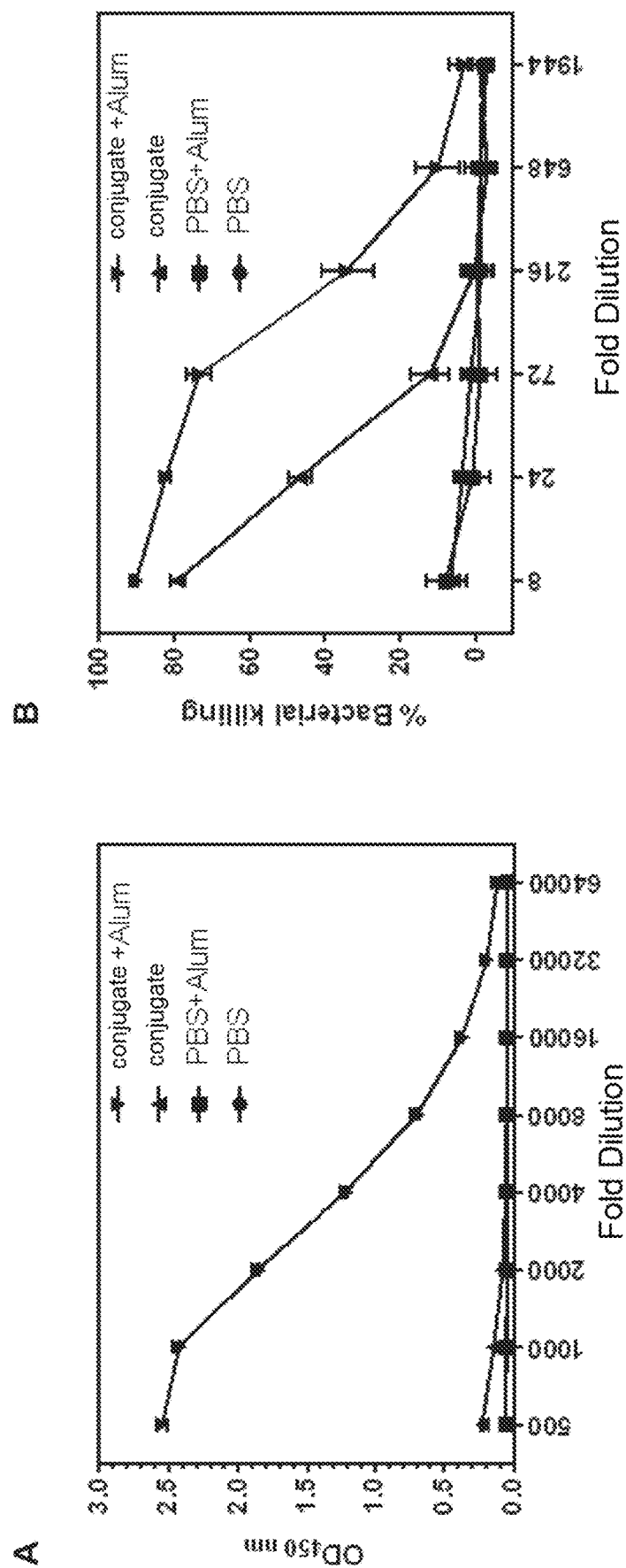
FIG. 6: ELISA and opsonophagocytic killing assay (OPKA). (A) Mice were immunized with conjugate CRM$_{197}$-hexasaccharide 2 with alum (1:1) and without alum. Pre and post immunized sera were collected and end point titer was analyzed by ELISA. In negative control mice were received PBS alone and with alum. (B) The opsonophagocytic killing assay was performed with HL-60 cells incubated with pre-opsonized type 2 pneumococcal strain D39 and antibodies raised from conjugate CRM$_{197}$-hexasaccharide 2 with alum (1:1) and without alum. Survival was assessed after 45 min incubation. Percent killing of pneumococci was calculated based on viable pneumococcal colonies obtained relative to control sera. PBS and PBS+alum sera were used as negative controls. Data were represented as mean±SD values of triplicates.

Results:

The ELISA data suggested that conjugate $CRM_{197}$-hexasaccharide 2 with alum induced high titer of CPS specific antibodies, in contrast to mice vaccinated with conjugate $CRM_{197}$-hexasaccharide 2 only or immunized with PBS (PBS+alum or PBS only) (see FIG. 6A).

Example B.3: Opsonophagocytic Killing Assay

S. pneumoniae serotype 2 strain 39 (NCTC 7466) was pre-opsonized with hyperimmune sera 15 min at 37° C. and incubated with differentiated HL-60 cells (DSMZ no.:ACC 3) in 1:400 ratio (bacteria: HL-60 cells). Baby rabbit complement (Cedarlane, Canada; cat # CL3441-S) was used as complement source. The whole mixture was incubated for 45 min at 37° C. with shaking. The phagocytic activity was stopped by keeping the mixture on ice for 20 min and the survival was assessed by plating on Columbia agar with 5% sheep blood plates. Percent killing of pneumococci was calculated based on viable pneumococcal colonies obtained relative to control sera.

The results suggest that anti-conjugate $CRM_{197}$-hexasaccharide 2 antibodies exhibited very high bactericidal activity compared to the control groups (FIG. 6B). These results supported the notion that conjugate $CRM_{197}$-hexasaccharide 2 induced functional immune response and thereby contributed to killing of pneumococci in vitro.

Example B.4: Vaccination with Conjugate $CRM_{197}$-Hexasaccharide 2 Provides Full Protection in Mice Against Intranasal Challenge with S. pneumoniae Seven week old female C57BL/6J mice (n=11) were immunized subcutaneously with conjugate $CRM_{197}$-hexasaccharide 2 (2.2 µg sugar per dose) with or without aluminium hydroxide (125 mg Al) in PBS on day 0, 14 and 28. Two control groups (n=11) received only PBS and PBS plus aluminium hydroxide (125 mg Al). Another shame group (n=11) was injected PBS only to minus the background. One week after the second booster, mice were challenged intranasally with $1 \times 10^7$ cfu of type strain D39 per mouse. The shame group received only PBS intranasally. Animals were monitored every 12 hr. Thirty six hours post challenge mice were anesthetized with Ketamine/Xylazine and euthanized in sterile conditions. The bacterial load was analyzed in lung and blood. Flushed lungs were homogenized and single cell suspension was prepared with the help of syringe. The pneumococci from alveoli and blood were enumerated by plating on blood agar plates.

Figure 7:
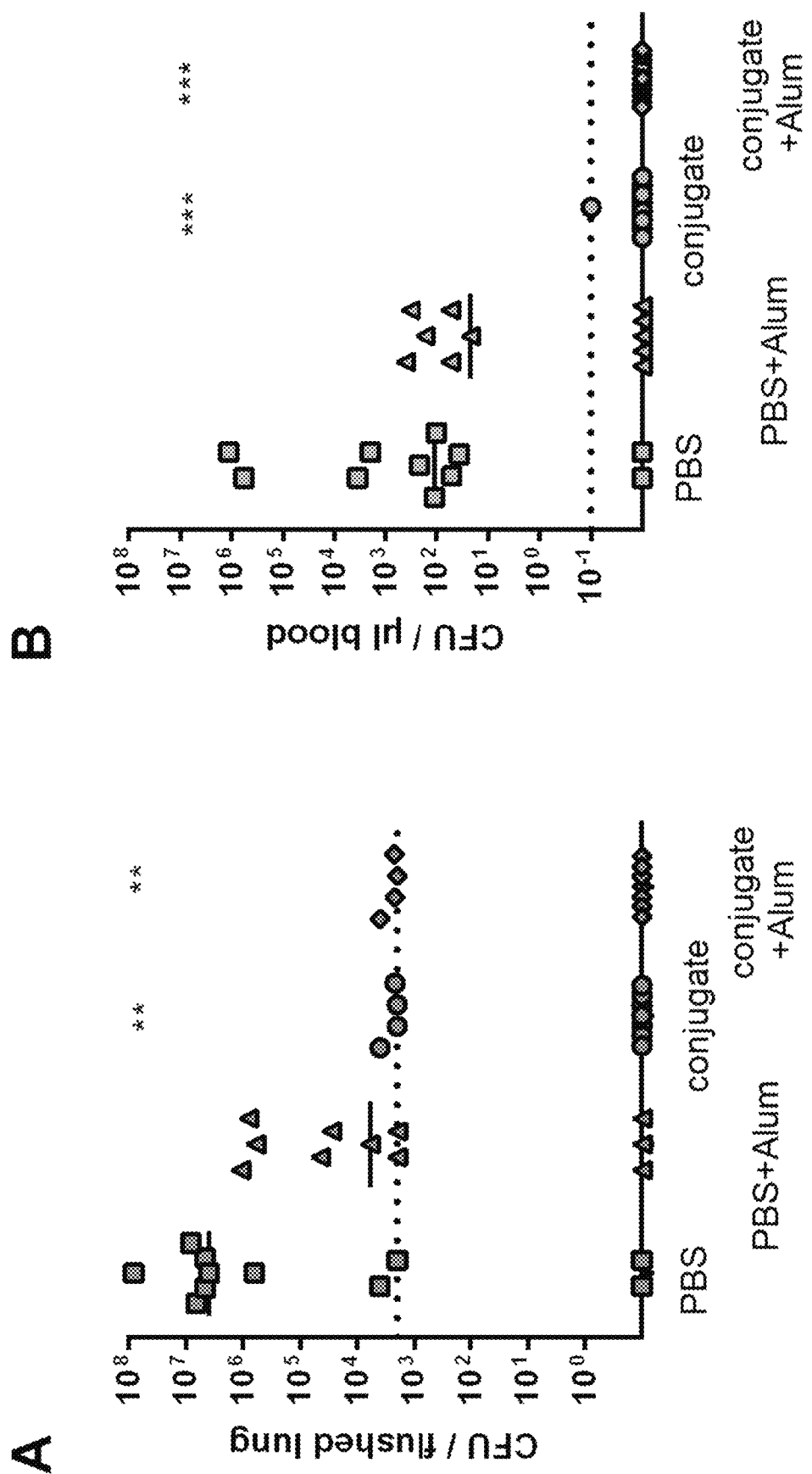
FIG. 7: Immunization with conjugate CRM$_{197}$-hexasaccharide 2 induces protective immunity in mice. Female C57BL/6J mice (n=11) were immunized subcutaneously with conjugate CRM$_{197}$-hexasaccharide 2 with or without alum subcutaneously (solid circle and diamond). The control group received PBS (squire) or PBS with alum (triangle). All groups of mice were challenged intranasally with 1×10$^7$ cfu of strain D39 and the mouse survival was monitored every 12 hr. Protection was analyzed after thirty six hour by cfu counting.

The colony forming unit data (CFU) suggested that mice vaccinated with conjugate $CRM_{197}$-hexasaccharide 2 reduced significantly the number of CFU against intranasal challenge compared to the PBS injected mice (see FIGS. 7A

The invention claimed is:

1. A saccharide of general formula (I)

$$V^*-U_{x+3}-U_{x+2}-U_{x+1}-U_x-O-L-NH_2 \quad (I)$$

wherein x is an integer selected from 1, 2, 3 and 4;

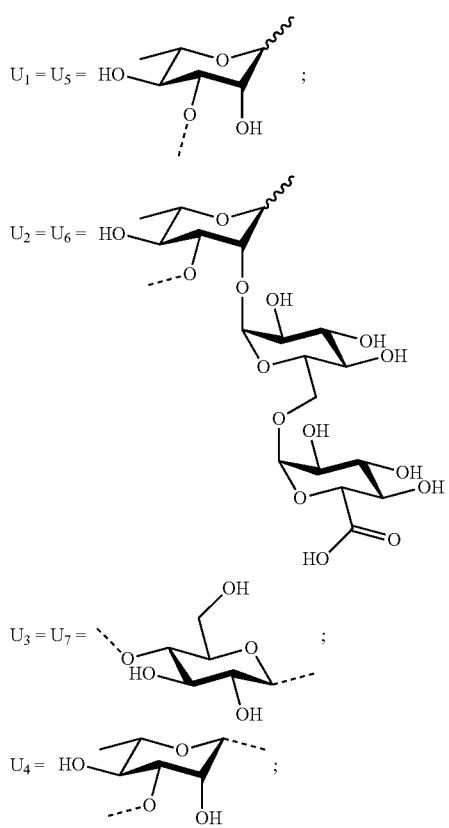

V*- represents H-, H-$U_x$-, H-$U_{x+1}$-$U_x$-, H-$U_{x+2}$-$U_{x+1}$-$U_x$- or H-$U_{x+3}$-$U_{x+2}$-$U_{x+1}$-$U_x$-;

L is selected from

—CH$_2$—, —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, —(CH$_2$)$_8$—, —(CH$_2$)$_9$—, —(CH$_2$)$_{10}$—, —CF$_2$—, —(CF$_2$)$_2$—, —(CF$_2$)$_3$—, —(CF$_2$)$_4$—, —(CF$_2$)$_5$—, —(CF$_2$)$_6$—, —(CF$_2$)$_7$—, —(CF$_2$)$_8$—, —(CF$_2$)$_9$—, —(CF$_2$)$_{10}$—, —(CH$_2$)$_2$—O—(CH$_2$)$_2$—, —CH$_2$—O—(CH$_2$)$_3$—, —(CH$_2$)$_3$O—CH$_2$—, —CH$_2$—O—(CH$_2$)$_2$—, —(CH$_2$)$_2$O—CH$_2$—, —(CH$_2$)$_3$—O—(CH$_2$)$_2$—, —(CH$_2$)$_2$—O—(CH$_2$)$_3$—, —(CH$_2$)$_4$—O—CH$_2$—, —CH$_2$—O—(CH$_2$)$_4$—, -L$^a$-, -L$^a$-L$^e$-, -L$^a$-L$^b$-L$^e$-, -L$^a$-L$^b$-L$^d$-L$^c$-L$^e$-, and -L$^a$-L$^d$-L$^e$-;

wherein

-L$^a$- is selected from: —(CH$_2$)$_o$—, —(CF$_2$)$_o$—, —(CH$_2$—CH$_2$—O)$_o$—C$_2$H$_4$—, —(CH$_2$—CH$_2$—O)$_o$—CH$_2$—, —(CR$^{10}$R$^{11}$)$_o$—,

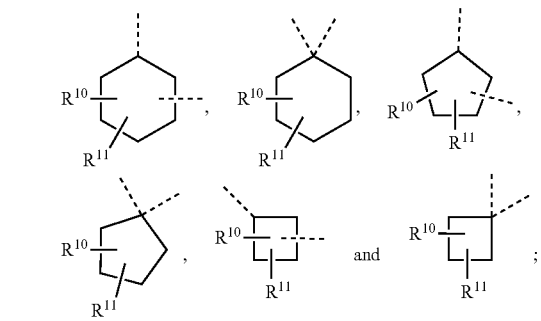

-L$^b$- and -L$^c$- are independently of each other selected from: —O—, —NH—C(O)—NH—, —NH—C(S)—NH—, —NH—C(O)—, —C(O)—NH—, —NH—C(O)—O—, —NR$^9$—, —NR$^{18}$—, —SO$_2$—,

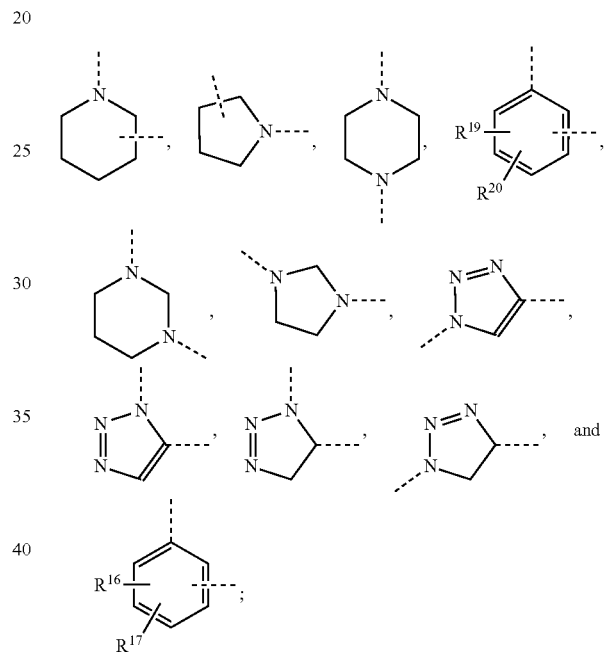

-L$^d$- represents —(CH$_2$)$_q$—, —(CF$_2$)$_q$—, —(CR$^{12}$R$^{13}$)$_q$—, —(CH$_2$—CH$_2$—O)$_q$—C$_2$H$_4$—, —CH$_2$—CH$_2$—O)$_q$—CH$_2$—,

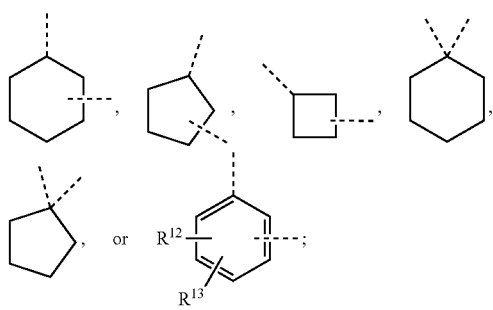

-L$^e$- is selected from: —(CH$_2$)$_{p1}$—, —(CF$_2$)$_{p1}$—, —C$_2$H$_4$—(O—CH$_2$—CH$_2$)$_{p1}$—, —CH$_2$—(O—CH$_2$—CH$_2$)$_{p1}$—, —(CH$_2$)$_{p1}$—O—(CH$_2$)$_{p2}$—, —(CR$^{14}$R$^{15}$)$_{p1}$—, —(CR$^{14}$R$^{15}$)$_{p1}$—O—(CR$^{21}$R$^{22}$)$_{q2}$—,

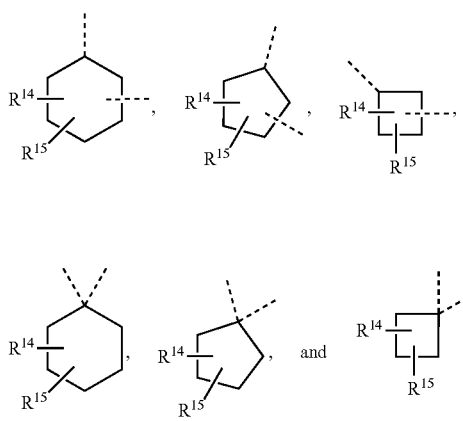

R⁹ and R¹⁸ are independently of each other selected from: —CH₃, —C₂H₅, —C₃H₇, and —C(O)CH₃;

R¹⁰, R¹¹, R¹², R¹³, R¹⁴, R¹⁵, R¹⁶, R¹⁷, R¹⁹, R²⁰, R²¹ and R²² are independently of each other selected from: —H, —F, —Cl, —CH₃, —C₂H₅, —C₃H₇, —C₅H₉, —C₆H₁₃, —OCH₃, —OC₂H₅, —CH₂F, —CHF₂, —CF₃, —C(O)—NH₂, —SCH₃, —SC₂H₅, —NHC(O)CH₃, —N(CH₃)₂ and —N(C₂H₅)₂;

o, q, p1 and p2 are independently of each other an integer selected from 1, 2, 3, 4, 5, 6, 7, 8, 9, and 10;

or a pharmaceutically acceptable salt thereof.

2. The saccharide according to claim 1, wherein x represents 1, or a pharmaceutically acceptable salt thereof.

3. The saccharide according to claim 1, wherein

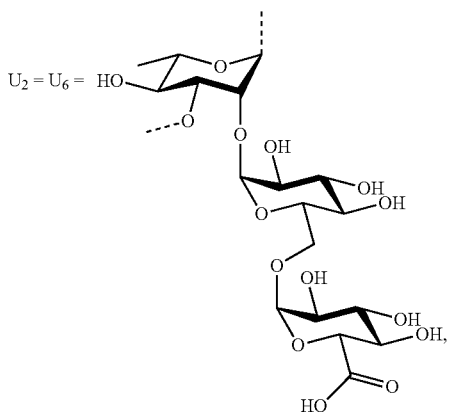

or a pharmaceutically acceptable salt thereof.

4. The saccharide according to claim 1, wherein

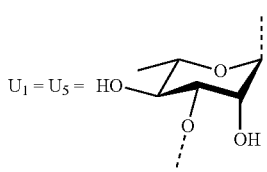

or a pharmaceutically acceptable salt thereof.

5. A method of synthesis of a saccharide of general formula (I) according to claim 1, wherein x represents 1, V*- represents H- and

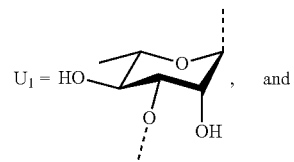

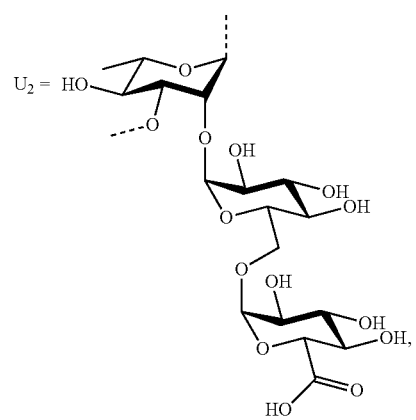

comprising the following steps:

A) reacting a disaccharide of general formula (II)

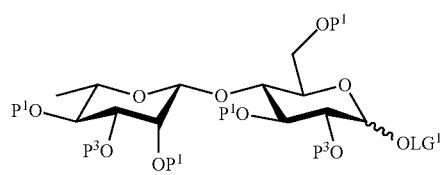

(II)

wherein P¹-P³ represent protecting groups, and LG¹ represents a leaving group, with a disaccharide of general formula (III)

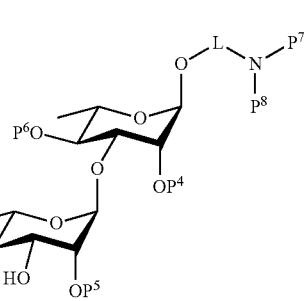

(III)

wherein P⁴-P⁸ represent protecting groups and L has the meaning as defined in claim 1, to obtain a tetrasaccharide of general formula (IV)

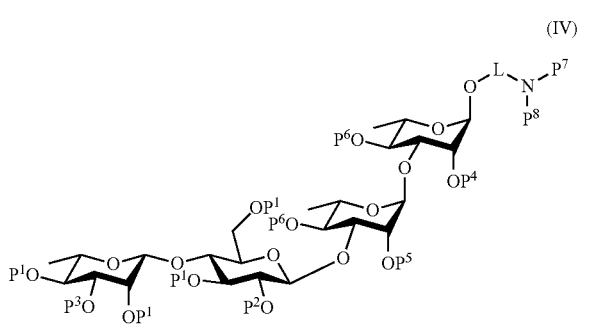

(IV)

wherein P¹-P⁸ represent protecting groups;
and

B) subjecting the tetrasaccharide of general formula (IV) to selective deprotection to obtain a tetrasaccharide of general formula (V)

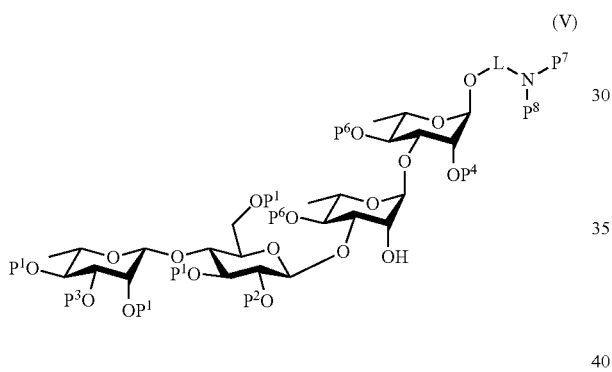

(V)

wherein P¹-P⁴, P⁶-P⁸ represent protecting groups and L has the meaning defined in claim 1; and C) reacting the tetrasaccharide of general formula (V) with a disaccharide of general formula (VI)

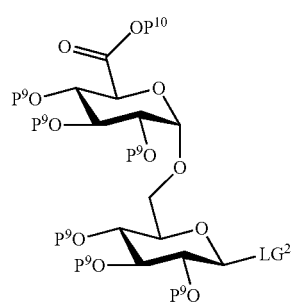

(VI)

wherein P⁹ and P¹⁰ represent protecting groups and LG² represents a leaving group to obtain a hexasaccharide of general formula (VII)

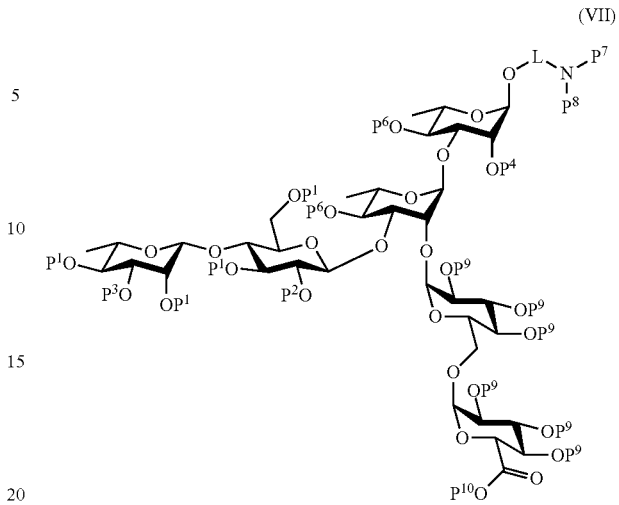

(VII)

wherein P¹-P⁴, P⁶-P¹⁰ represent protecting groups and L has the meaning defined in claim 1;
and D) performing the removal of protecting groups P¹-P⁴, P⁶-P¹⁰ on the compound of general formula (VII).

6. An intermediate of general formula (V)

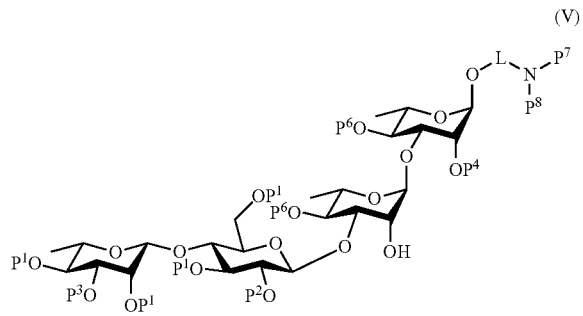

(V)

wherein P¹- P⁴, P⁶-P⁸ represent protecting groups and L has the meaning defined in claim 1.

7. The intermediate of general formula (V) according to claim 6, wherein P¹, P⁶ and P⁷ represent a benzyl group, P², P³ and P⁴ are independently of each other selected from benzoyl and acetyl group, and P⁸ represents a benzyloxy carbonyl group.

8. A conjugate of general formula (X)

$$[V^*\text{-}U_{x+3}\text{-}U_{x+2}\text{-}U_{x+1}\text{-}U_x\text{-}O\text{-}L\text{-}NH\text{-}W]_m\text{-}CRM_{197} \quad (X)$$

wherein m is comprised between about 2 and about 18;
-W- is selected from:

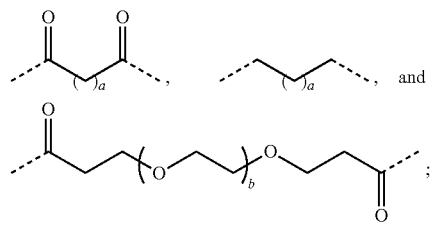

a represents an integer from 1 to 10;

b represents an integer from 1 to 4; and

V*, $U_{x+3}$, $U_{x+2}$, $U_{x+1}$, $U_x$, x and L have the meanings as defined in claim 1.

9. A saccharide according to claim 1 for use in raising a protective immune response in a human and/or animal host.

10. A saccharide according to claim 1 for use in the prevention and/or treatment of a disease caused by *Streptococcus pneumoniae* type 2.

11. A vaccine comprising the saccharide and/or the pharmaceutically acceptable salt thereof according to claim 1 together with at least one pharmaceutically acceptable adjuvant and/or excipient.

12. The vaccine composition according to claim 11, further comprising at least a capsular polysaccharide of *Streptococcus pneumoniae* and/or a fragment of a capsular polysaccharide of *Streptococcus pneumoniae* and/or a conjugate of a carrier protein and a capsular polysaccharide of *Streptococcus pneumoniae* or a fragment of a capsular polysaccharide of *Streptococcus pneumoniae*, wherein *Streptococcus pneumoniae* is selected from the group comprising *Streptococcus pneumoniae* type 1, 3, 4, 5, 6A, 6B, 7F, 8, 9N, 9V, 10A, 11A, 12F, 14, 15B, 17F, 18C, 19F, 19A, 20, 22F, 23F and 33F.

13. A saccharide according to claim 1 for use as marker in immunological assays for detection of antibodies against *Streptococcus pneumoniae* type 2.

14. A conjugate according to claim 8 for use in raising a protective immune response in a human and/or animal host.

15. A conjugate according to claim 8 for use in the prevention and/or treatment of a disease caused by *Streptococcus pneumoniae* type 2.

16. A vaccine comprising the conjugate according to claim 8 together with at least one pharmaceutically acceptable adjuvant and/or excipient.

17. The vaccine composition according to claim 16, further comprising at least a capsular polysaccharide of *Streptococcus pneumoniae* and/or a fragment of a capsular polysaccharide of *Streptococcus pneumoniae* and/or a conjugate of a carrier protein and a capsular polysaccharide of *Streptococcus pneumoniae* or a fragment of a capsular polysaccharide of *Streptococcus pneumoniae*, wherein *Streptococcus pneumoniae* is selected from the group comprising *Streptococcus pneumoniae* type 1, 3, 4, 5, 6A, 6B, 7F, 8, 9N, 9V, 10A, 11A, 12F, 14, 15B, 17F, 18C, 19F, 19A, 20, 22F, 23F and 33F.

* * * * *